(12) United States Patent
Mathews et al.

(10) Patent No.: US 8,536,351 B2
(45) Date of Patent: Sep. 17, 2013

(54) 2-ARYL-5-HETEROCYCLYL-CYCLOHEXANE-1,3,DIONE COMPOUNDS AND THEIR USE AS HERBICIDES

(75) Inventors: Christopher John Mathews, Bracknell (GB); John Finney, Bracknell (GB); Louisa Robinson, Bracknell (GB); Melloney Tyte, Bracknell (GB); Michel Muehlebach, Stein (CH); Jean Wenger, Wallbach (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 658 days.

(21) Appl. No.: 12/530,476

(22) PCT Filed: Mar. 7, 2008

(86) PCT No.: PCT/EP2008/001840
§ 371 (c)(1),
(2), (4) Date: Jan. 4, 2010

(87) PCT Pub. No.: WO2008/110307
PCT Pub. Date: Sep. 18, 2008

(65) Prior Publication Data
US 2010/0113270 A1    May 6, 2010

(30) Foreign Application Priority Data
Mar. 9, 2007  (GB) .................. 0704653.5

(51) Int. Cl.
*C07D 307/02*   (2006.01)
*C07D 409/00*   (2006.01)
*A01N 43/02*    (2006.01)
*A01N 43/08*    (2006.01)

(52) U.S. Cl.
USPC ............. 549/501; 549/508; 549/13; 549/29; 549/80; 504/288; 504/103; 504/294; 504/292; 504/295; 504/293; 504/251; 504/296; 504/140; 504/176

(58) Field of Classification Search
USPC ............. 549/501, 508, 80, 13, 29; 504/288, 504/103, 294, 292, 295, 293, 251, 296, 140, 504/130, 176
See application file for complete search history.

(56) References Cited

U.S. PATENT DOCUMENTS
4,256,659 A * 3/1981 Wheeler .................. 558/371
4,659,372 A   4/1987 Wheeler

FOREIGN PATENT DOCUMENTS
WO     200174770    10/2001

OTHER PUBLICATIONS
Neilands et al, Chem. Abs. DN 60:30746 (1963).*

* cited by examiner

*Primary Examiner* — Andrew D Kosar
*Assistant Examiner* — Raymond Covington
(74) *Attorney, Agent, or Firm* — R. Kody Jones

(57) ABSTRACT

Cyclohexanedione compounds of Formula (I) wherein $R^1$ is methyl, ethyl, n-propyl, iso-propyl, cyclopropyl, halomethyl, haloethyl, halogen, vinyl, ethynyl, methoxy, ethoxy, halomethoxy or haloethoxy, $R^2$ and $R^3$ are, independently hydrogen, halogen, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$haloalkenyl, $C_2$-$C_6$alkynyl, $C_3$-$C_6$alkenyloxy, $C_3$-$C_6$haloalkenyloxy, $C_3$-$C_6$alkynyloxy, $C_3$-$C_6$cycloalkyl, $C_1$-$C_6$alkylthio, $C_1$-$C_6$alkylsulfinyl, $C_1$-$C_6$alkylsulfonyl, $C_1$-$C_6$alkylsulfonyloxy, $C_1$-$C_6$haloalkylsulfonyloxy, cyano, nitro, phenyl, phenyl substituted by $C_1$-$C_4$alkyl, $C_1$-$C_3$Cahaloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, or heteroaryl or heteroaryl substituted by $C_1$-$C_3$Calkyl, d.Cahaloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, $R^4$ is hydrogen, methyl, ethyl, n-propyl, iso-propyl, halomethyl, haloethyl, halogen, vinyl, ethynyl, methoxy, ethoxy, halomethoxy or haloethoxy, X is O, S, S(O) or $S(O)_2$, $R^5$ is hydrogen or methyl, $R^6$ is hydrogen, methyl or ethyl, or forms a double bond, which links the carbon atom, to which $R^6$ is attached, with the adjacent carbon atom of $R^7$ or $R^8$, $R^7$ and $R^8$ are independently of each other $C_1$-$C_5$alkylene, which is unsubstituted or substituted by methyl or ethyl, or $C_2$-$C_5$alkenylene, which is unsubstituted or substituted by methyl or ethyl, and G is hydrogen, an alkali metal, alkaline earth metal, sulfonium, ammonium or a latentiating group, are suitable for use as herbicides.

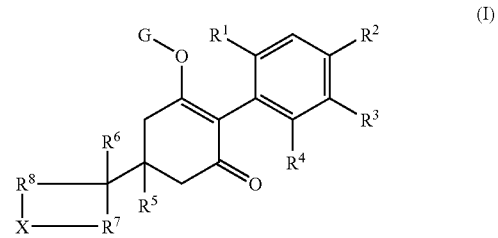

31 Claims, No Drawings

2-ARYL-5-HETEROCYCLYL-CYCLOHEXANE-1,3,DIONE COMPOUNDS AND THEIR USE AS HERBICIDES

This application is a 371 of International Application No. PCT/EP2008/001840 filed Mar. 7, 2008, which claims priority to GB 0704653.5 filed Mar. 9, 2007, the contents of which are incorporated herein by reference.

The present invention relates to novel, herbicidally active cyclic diones, and derivatives thereof, to processes for their preparation, to compositions comprising those compounds, and to their use in controlling weeds, especially in crops of useful plants, or in inhibiting plant growth.

Cyclic diones having herbicidal action are described, for example, in WO 01/74770.

Novel cyclohexanedione compounds, and derivatives thereof, having herbicidal and growth-inhibiting properties have now been found.

The present invention accordingly relates to compounds of Formula (I)

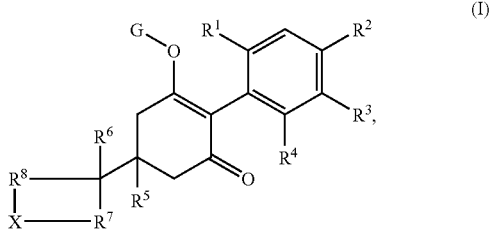

wherein
$R^1$ is methyl, ethyl, n-propyl, iso-propyl, cyclopropyl, halomethyl, haloethyl, halogen, vinyl, ethynyl, methoxy, ethoxy, halomethoxy or haloethoxy,
$R^2$ and $R^3$ are, independently hydrogen, halogen, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$haloalkenyl, $C_2$-$C_6$alkynyl, $C_3$-$C_6$alkenyloxy, $C_3$-$C_6$haloalkenyloxy, $C_3$-$C_6$alkynyloxy, $C_3$-$C_6$cycloalkyl, $C_1$-$C_6$alkylthio, $C_1$-$C_6$alkylsulfinyl, $C_1$-$C_6$alkylsulfonyl, $C_1$-$C_6$alkylsulfonyloxy, $C_1$-$C_6$haloalkylsulfonyloxy, cyano, nitro, phenyl, phenyl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, or heteroaryl or heteroaryl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl,
$R^4$ is hydrogen, methyl, ethyl, n-propyl, iso-propyl, halomethyl, haloethyl, halogen, vinyl, ethynyl, methoxy, ethoxy, halomethoxy or haloethoxy,
X is O, S, S(O) or S(O)$_2$,
$R^5$ is hydrogen or methyl,
$R^6$ is hydrogen, methyl or ethyl, or forms a double bond, which links the carbon atom, to which $R^6$ is attached, with the adjacent carbon atom of $R^7$ or $R^8$,
$R^7$ and $R^8$ are independently of each other $C_1$-$C_5$alkylene, which is unsubstituted or substituted by methyl or ethyl, or $C_2$-$C_5$alkenylene, which is unsubstituted or substituted by methyl or ethyl,
G is hydrogen, an alkali metal, alkaline earth metal, sulfonium, ammonium or a latentiating group.

In the substituent definitions of the compounds of the Formula (I), the alkyl substituents and alkyl moieties of alkoxy, alkylamino etc. having 1 to 6 carbon atoms are preferably methyl, ethyl, propyl, butyl, pentyl and hexyl as well as straight and branched isomers thereof. Higher alkyl groups of up to 18 carbon atoms comprise preferably octyl, nonyl, decyl, undecyl and dodecyl. The alkenyl and alkynyl radicals having 2 to 6 carbon atoms as well as up to 18 carbon atoms can be straight or branched and can contain more than 1 double or triple bond, respectively. Examples are vinyl, allyl, propargyl, butenyl, butynyl, pentenyl and pentynyl Suitable cycloalkyl groups contain 3 to 6 carbon atoms and are for example cyclopropyl, cyclobutyl, cyclopentyl, cyclohexyl and cycloheptyl. Cyclopropyl, cyclobutyl, cyclopentyl and cyclohexyl are preferred. Preferred examples of heteroaryls are thienyl, furyl, pyrrolyl, oxazolyl, thiazolyl, pyrazolyl, imidazolyl, triazolyl, tetrazolyl, pyridyl, pyrimidinyl, pyrazinyl, triazinyl, benzofuryl, benzothienyl, benzothiazolyl, benzoxazolyl, indolyl, quinolinyl and quinoxalinyl groups, and, where appropriate, N-oxides and salts thereof. The group G is hydrogen or an alkali metal, alkaline earth metal, sulfonium (—S($C_1$-$C_6$alkyl$_3$)$^+$), ammonium (—NH$_4^+$ or —N($C_1$-$C_6$alkyl)$_4^+$) or a leaving group. This latentiating group G is selected to allow its removal by one or a combination of biochemical, chemical or physical processes to afford compounds of Formula (I) where G is H before, during or following application to the treated area or plants. Examples of these processes include enzymatic cleavage, chemical hydrolysis and photolysis. Compounds bearing latentiating groups G may offer certain advantages, such as improved penetration of the cuticula of the plants treated, increased tolerance of crops, improved compatibility or stability in formulated mixtures containing other herbicides, herbicide safeners, plant growth regulators, fungicides or insecticides, or reduced leaching in soils. A large number of latentiating groups, which are known in the art, can be used in the new compounds.

In a preferred group of compounds of the formula I, $R^1$ is methyl, ethyl, vinyl, ethynyl, methoxy or halogen. More preferably, $R^1$ is methyl or ethyl.

Preferably, $R^2$ and $R^3$ are independently hydrogen, methyl, ethyl, halogen, optionally substituted phenyl or optionally substituted heteroaryl.

Preferably, $R^4$ is hydrogen, methyl, ethyl, vinyl or ethynyl and, more preferably, $R^4$ is hydrogen, methyl or ethyl.

In another preferred group of compounds of the formula (I) $R^1$, $R^2$ and $R^4$ are independently of each other methyl or ethyl and $R^3$ is hydrogen.

In another preferred group of compounds of the formula (I) $R^1$ is methyl or ethyl, $R^2$ is hydrogen, $R^3$ is phenyl or phenyl substituted by $C_1$-$C_4$alkyl, $C_1$-$C_3$haloalkyl, $C_1$-$C_3$alkoxy, $C_1$-$C_3$haloalkoxy, cyano, nitro or halogen, or heteroaryl or heteroaryl substituted by $C_1$-$C_4$alkyl, $C_1$-$C_3$haloalkyl, $C_1$-$C_3$alkoxy, $C_1$-$C_3$ haloalkoxy, cyano, nitro or halogen.

In another preferred group of compounds of the formula (I) $R^1$ is methyl or ethyl, $R^2$ is phenyl or phenyl substituted by $C_1$-$C_4$alkyl, $C_1$-$C_3$haloalkyl, $C_1$-$C_3$alkoxy, $C_1$-$C_3$haloalkoxy, cyano, nitro or halogen, or heteroaryl or heteroaryl substituted by $C_1$-$C_4$alkyl, $C_1$-$C_3$haloalkyl, $C_1$-$C_3$alkoxy, $C_1$-$C_3$haloalkoxy, cyano, nitro or halogen, $R^3$ is hydrogen and $R^4$ is hydrogen, methyl or ethyl.

Substituent $R^5$ is preferably hydrogen
Substituent $R^6$ is preferably hydrogen
In a preferred group of compounds of the Formula (I), $R^7$ and $R^8$ are independently of each other methylene, ethylene, propylene or propenylene.

More preferably, $R^7$ and $R^8$ are ethylene.
The latentiating group G is preferably selected from the groups G is $C_1$-$C_8$ alkyl, $C_2$-$C_8$ haloalkyl, phenyl$C_1$-$C_8$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl$C_1$-$C_8$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_8$ alkenyl, $C_3$-$C_8$ haloalkenyl, $C_3$-$C_8$ alkynyl, $C(X^a)$—$R^a$, $C(X^b)$—$X^c$—$R^b$, $C(X^d)$—$N(R^c)$—$R^d$, —$SO_2$—$R^e$, —$P(X^e)(R^f)$—$R^g$ or $CH_2$—$X^f$—$R^b$ wherein $X^a$, $X^b$, $X^c$, $X^d$, $X^e$ and $X^f$ are independently of each other oxygen or sulfur;

$R^a$ is H, $C_1$-$C_{18}$alkyl, $C_2$-$C_{18}$alkenyl, $C_2$-$C_{18}$alkynyl, $C_1$-$C_{18}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyl$C_1$-$C_5$oxyalkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_5$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, $R^b$ is $C_1$-$C_{18}$alkyl, $C_3$-$C_{18}$alkenyl, $C_3$-$C_{18}$alkynyl, $C_2$-$C_{10}$haloalkyl, $C_1$-$C_{10}$cyanoalkyl, $C_1$-$C_{10}$nitroalkyl, $C_2$-$C_{10}$-aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_5$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro or $C_3$-$C_7$cycloalkylamino, di-$C_3$-$C_7$cycloalkylamino or $C_3$-$C_7$cycloalkoxy or $R^c$ and $R^d$ may join together to form a 3-7 membered ring, optionally containing one heteroatom selected from O or S $R^e$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$alkoxy, $C_1$-$C_{10}$haloalkoxy, $C_1$-$C_5$alkylamino or $C_2$-$C_8$dialkylamino $R^f$ and $R^g$ are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$haloalkoxy, $C_1$-$C_5$alkylamino or $C_2$-$C_8$dialkylamino, benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro, and $R^h$ is $C_1$-$C_{10}$alkyl, $C_3$-$C_{10}$alkenyl, $C_3$-$C_{10}$alkynyl, $C_1$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), phenoxy$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryloxy$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_5$haloalkenyl, $C_3$-$C_5$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro, or heteroaryl, or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro.

In particular, the latentiating group G is a group —C($X^a$)—$R^a$ or —C($X^b$)—$X^c$—$R^b$, and the meanings of $X^a$, $R^a$, $X^b$, $X^c$ and $R^b$ are as defined above.

It is preferred that G is hydrogen, an alkali metal or alkaline earth metal, where hydrogen is especially preferred.

In a preferred group of compounds of the formula (I), X is O or S.

In another preferred group of compounds of the formula (I), X is S(O) or S(O)$_2$.

The invention relates also to the salts which the compounds of formula I are able to form with amines, alkali metal and alkaline earth metal bases or quaternary ammonium bases. Among the alkali metal and alkaline earth metal hydroxides as salt formers, special mention should be made of the hydroxides of lithium, sodium, potassium, magnesium and calcium, but especially the hydroxides of sodium and potassium. The compounds of formula I according to the invention also include hydrates which may be formed during the salt formation.

Examples of amines suitable for ammonium salt formation include ammonia as well as primary, secondary and tertiary $C_1$-$C_{18}$alkylamines, $C_1$-$C_4$hydroxyalkylamines and $C_2$-$C_4$-alkoxyalkylamines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, isopropylamine and diisopropylamine.

Preferred quaternary ammonium bases suitable for salt formation correspond, for example, to the formula $[N(R_aR_bR_cR_d)]OH$ wherein $R_a$, $R_b$, $R_c$ and $R_d$ are each independently of the others $C_1$-$C_4$alkyl. Further suitable tetraalkylammonium bases with other anions can be obtained, for example, by anion exchange reactions.

Depending on the nature of the substituents G, $R^c$, $R^2$, $R^3$ and $R^4$, compounds of formula I may exist in different isomeric forms. When G is hydrogen, for example, compounds of formula I may exist in different tautomeric forms. This invention covers all such isomers and tautomers and mixtures thereof in all proportions. Also, when substituents contain double bonds, cis- and trans-isomers can exist. These isomers, too, are within the scope of the claimed compounds of the Formula (I).

The compounds of Formula (I), wherein the substituents have the meanings assigned to them above, can be prepared by means of processes known per se, e.g. by treating compounds of Formula A with an alkylating, acylating, phosphorylating or sulfonylating agent.

A compound of Formula (I) wherein G is $C_1$-$C_8$ alkyl, $C_2$-$C_8$ haloalkyl, phenyl$C_1$-$C_8$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsufinyl, $C_1$-$C_3$ alkylsulfonyl, halogen, cyano or by nitro), heteroaryl$C_1$-$C_8$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsufinyl, $C_1$-$C_3$ alkylsulfonyl, halogen, cyano or by nitro), $C_3$-$C_8$ alkenyl, $C_3$-$C_8$ haloalkenyl, $C_3$-$C_8$ alkynyl, $C(X^a)$—$R^a$, $C(X^b)$—$X^c$—$R^b$, $C(X^d)$—$N(R^c)$—$R^d$, —$SO_2$—$R^e$, —$P(X^e)(R^f)$—$R^g$ or $CH_2$—$X^f$—$R^h$ where $X^a$, $X^b$, $X^c$, $X^d$, $X^e$, $X^f$, $R^a$, $R^b$, $R^c$, $R^d$, $R^e$, $R^f$, $R^g$ and $R^h$ are as defined above may be prepared by treating a compound of Formula (A), which is a compound of Formula (I) wherein G is H, with a reagent G-Z, wherein G-Z is alkylating agent such as an alkyl halide (the definition of alkyl halides includes simple $C_1$-$C_8$ alkyl halides such as methyl iodide and ethyl iodide, substituted alkyl halides such as phenyl$C_1$-$C_8$alkyl halides, chloromethyl alkyl ethers, Cl—$CH_2$—$X^f$—$R^h$, wherein $X^f$ is oxygen, and chloromethyl alkyl sulfides Cl—$CH_2$—$X^f$—$R^h$, wherein $X^f$ is sulfur), a $C_1$-$C_8$ alkyl sulfonate, or a di-$C_1$-$C_8$-alkyl sulfate, or with a $C_3$-$C_8$ alkenyl halide, or with a $C_3$-$C_8$ alkynyl halide, or with an acylating agent such as a carboxylic acid, HO—$C(X^a)R^a$, wherein $X^a$ is oxygen, an acid chloride, Cl—$C(X^a)R^a$, wherein $X^a$ is oxygen, or acid anhydride, $[R^aC(X^a)]_2O$, wherein $X^a$ is oxygen, or an isocyanate, $R^cN$=$C$=$O$, or a carbamoyl chloride, Cl—$C(X^d)$—$N(R^c)$—$R^d$ (wherein $X^d$ is oxygen and with the proviso that neither $R^c$ or $R^d$ is hydrogen), or a thiocarbamoyl chloride, Cl—$C(X^d)$—$N(R^c)$—$R^d$ (wherein $X^d$ is sulfur and with the proviso that neither $R^c$ or $R^d$ is hydrogen) or a chloroformate, Cl—$C(X^b)$—$X^c$—$R^b$, (wherein $X^b$ and $X^c$ are oxygen), or a chlorothioformate Cl—$C(X^b)$—$X^c$—$R^h$ (wherein $X^b$ is oxygen and $X^c$ is sulfur), or a chlorodithioformate Cl—$C(X^b)$—$X^c$—$R^b$, (wherein $X^b$ and $X^c$ are sulfur), or an isothiocyanate, $R^cN$=$C$=$S$, or by sequential treatment with carbon disulfide and an alkylating agent, or with a phosphorylating agent such as a phosphoryl chloride, Cl—$P(X^e)(R^f)$—$R^g$ or with a sulfonylating agent such as a sulfonyl chloride Cl—$SO_2$—$R^e$, preferably in the presence of at least one equivalent of base.

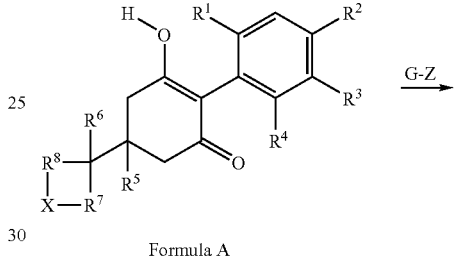

Formula A

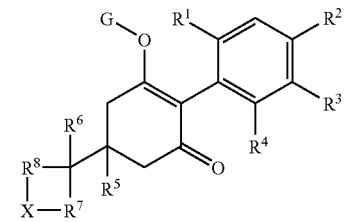

Formula (I)

The O-alkylation of cyclic 1,3-diones is known; suitable methods are described, for example, by T. Wheeler, U.S. Pat. No. 4,436,666. Alternative procedures have been reported by M. Pizzorno and S. Albonico, Chem. Ind. (London), (1972), 425-426; H. Born et al., J. Chem. Soc., (1953), 1779-1782; M. G. Constantino et al., Synth. Commun., (1992), 22 (19), 2859-2864; Y. Tian et al., Synth. Commun., (1997), 27 (9), 1577-1582; S. Chandra Roy et al., Chem. Letters, (2006), 35 (1), 16-17; P. K. Zubaidha et al., Tetrahedron Lett., (2004), 45, 7187-7188.

The O-acylation of cyclic 1,3-diones may be effected by procedures similar to those described, for example, by R. Haines, U.S. Pat. No. 4,175,135, and by T. Wheeler, U.S. Pat. Nos. 4,422,870, 4,659,372 and 4,436,666. Typically diones of formula (A) may be treated with an acylating agent preferably in the presence of at least one equivalent of a suitable base, and optionally in the presence of a suitable solvent. The base may be inorganic, such as an alkali metal carbonate or hydroxide, or a metal hydride, or an organic base such as a tertiary amine or metal alkoxide. Examples of suitable inorganic bases include sodium carbonate, sodium or potassium hydroxide, sodium hydride, and suitable organic bases include trialkylamines, such as trimethylamine and triethylamine, pyridines or other amine bases such as 1,4-diazobicyclo[2.2.2]-octane and 1,8-diazabicyclo[5.4.0]undec-7-ene.

Preferred bases include triethylamine and pyridine. Suitable solvents for this reaction are selected to be compatible with the reagents and include ethers such as tetrahydrofuran and 1,2-dimethoxyethane and halogenated solvents such as dichloromethane and chloroform. Certain bases, such as pyridine and triethylamine, may be employed successfully as both base and solvent. For cases where the acylating agent is a carboxylic acid, acylation is preferably effected in the presence of a known coupling agent such as 2-chloro-1-methylpyridinium iodide, N,N'-dicyclohexylcarbodiimide, 1-(3-dimethylaminopropyl)-3-ethylcarbodiimide and N,N'-carbodiimidazole, and optionally in the presence of a base such as triethylamine or pyridine in a suitable solvent such as tetrahydrofuran, dichloromethane or acetonitrile. Suitable procedures are described, for example, by W. Zhang and G. Pugh, Tetrahedron Lett., (1999), 40 (43), 7595-7598; T. Isobe and T. Ishikawa, J. Org. Chem., (1999), 64 (19), 6984-6988 and K. Nicolaou, T. Montagnon, G. Vassilikogiannakis, C. Mathison, J. Am. Chem. Soc., (2005), 127(24), 8872-8888.

Phosphorylation of cyclic 1,3-diones may be effected using a phosphoryl halide or thiophosphoryl halide and a base by procedures analogous to those described by L. Hodakowski, U.S. Pat. No. 4,409,153.

Sulfonylation of a compound of formula (A) may be achieved using an alkyl or aryl sulfonyl halide, preferably in the presence of at least one equivalent of base, for example by the procedure of C. Kowalski and K. Fields, J. Org. Chem., (1981), 46, 197-201.

Compounds of formula (A), wherein X is S(O) or X is $S(O)_2$ may be prepared from compounds of formula (A) wherein X is S by oxidation, according to known procedures, for example by treatment with hydrogen peroxide, or a peracid such as peracetic acid or meta-chloroperbenzoic acid under known conditions.

A compound of Formula (A) may be prepared by the cyclisation of a compound of Formula (B), wherein R is hydrogen or an alkyl group, preferably in the presence of an acid or base, and optionally in the presence of a suitable solvent, by analogous methods to those described by T. Wheeler, U.S. Pat. No. 4,209,532. The compounds of Formula (B) have been particularly designed as intermediates in the synthesis of the compounds of the Formula (I). A compound of Formula (B) wherein R is hydrogen may be cyclised under acidic conditions, preferably in the presence of a strong acid such as sulfuric acid, polyphosphoric acid or Eaton's reagent, optionally in the presence of a suitable solvent such as acetic acid, toluene or dichloromethane.

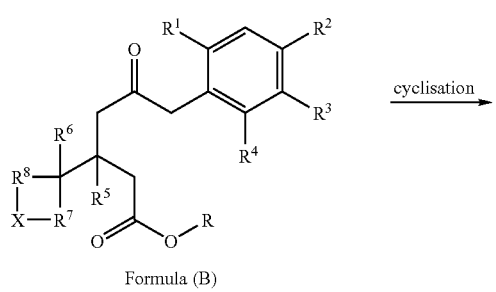

Formula (B)

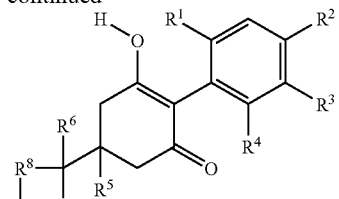

Formula (A)

A compound of Formula (B) wherein R is alkyl (preferably methyl or ethyl), may be cyclised under acidic or basic conditions, preferably in the presence of at least one equivalent of a strong base such as potassium tert-butoxide, lithium diisopropylamide or sodium hydride and in a solvent such as tetrahydrofuran, dimethylsulfoxide or N,N-dimethylformamide.

A compound of Formula (B), wherein R is H, may be prepared by saponification of a compound of Formula (C) wherein R' is alkyl (preferably methyl or ethyl), under standard conditions, followed by acidification of the reaction mixture to effect decarboxylation, by similar processes to those described, for example, by T. Wheeler, U.S. Pat. No. 4,209,532.

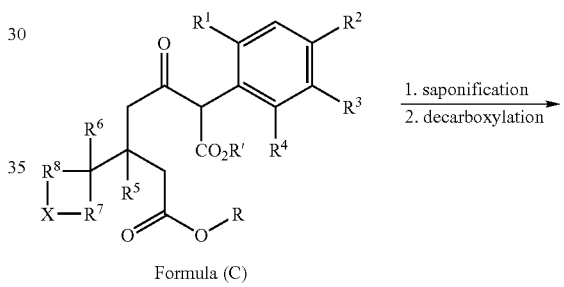

Formula (C)

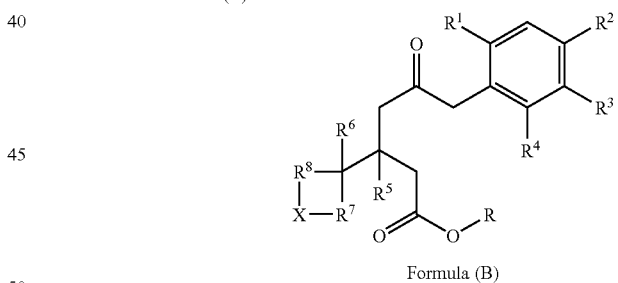

Formula (B)

A compound of Formula (B), wherein R is H, may be esterified to a compound of Formula (B), wherein R is alkyl, under known conditions, for example by heating with an alkyl alcohol, ROH, in the presence of an acid catalyst.

A compound of Formula (C), wherein R is alkyl, may be prepared by treating a compound of Formula (D) with a suitable carboxylic acid chloride of Formula (E) under basic conditions. Suitable bases include potassium tert-butoxide, sodium bis(trimethylsilyl)amide and lithium diisopropylamide and the reaction is preferably conducted in a suitable solvent (such as tetrahydrofuran or toluene) at a temperature of between −80° C. and 30° C. Alternatively, a compound of Formula (C), wherein R is H, may be prepared by treating a compound of Formula (D) with a suitable base (such as potassium tert-butoxide, sodium bis(trimethylsilyl)amide and lithium diisopropylamide) in a suitable solvent (such as tetrahydrofuran or toluene) at a suitable temperature (between −80° C. and 30° C.) and reacting the resulting anion with a suitable anhydride of Formula (F):

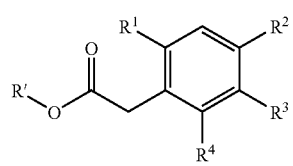

Formula (D)

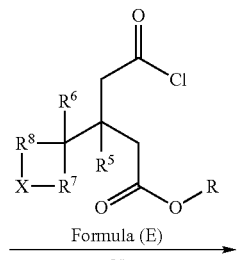

Formula (E)
or

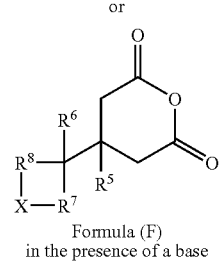

Formula (F)
in the presence of a base

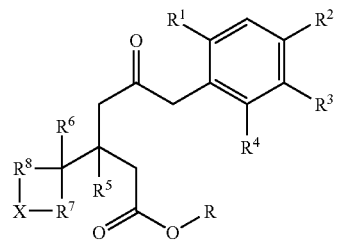

Formula (C)

Compounds of Formula (D) are known compounds, or may be prepared from known compounds by known methods.

A compound of Formula (E) may be prepared from a compound of Formula (F) by treatment with an alkyl alcohol, R—OH, followed by treatment of the resulting acid with a chlorinating reagent such as oxalyl chloride or thionyl chloride under known conditions (see, for example, C. Rouvier. Tetrahedron Lett., (1984), 25 (39), 4371; D. Walba and M. Wand, Tetrahedron Lett., (1982), 23, 4995; J. Cason, Org. Synth. Coll. Vol. III, (1955), 169).

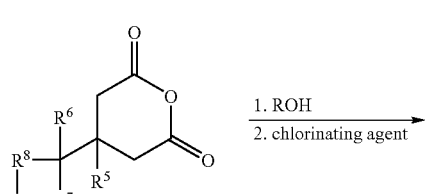

Formula (F)

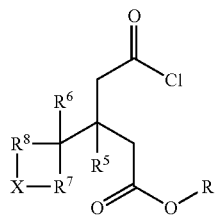

Formula (E)

A compound of Formula (F) may be prepared by treating a compound of Formula (G) with a dehydrating agent such as an acid anhydride (as described, for example by J. Cason, Org. Synth. Coll. Vol. IV, (1963), 630). A preferred acid anhydride is acetic anhydride.

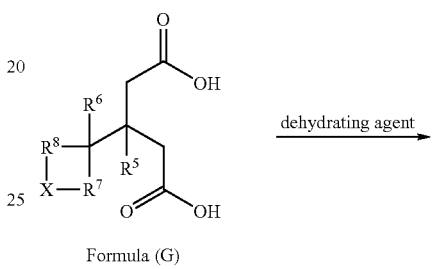

Formula (G)

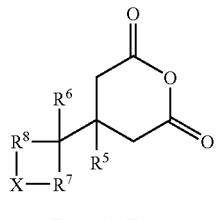

Formula (F)

A compound of Formula (G) may be prepared by saponification of an ester of Formula (H), wherein R″ and R‴ are suitable alkyl groups followed by decarboxylation of resulting acid. Suitable alkyl groups are $C_1$-$C_6$ alkyl, especially methyl or ethyl. Suitable methods for effecting saponification are known, and include, for example, treating an ester of Formula (H) with an aqueous solution of a suitable base such as sodium hydroxide or potassium hydroxide, and acidifying the reaction mixture with an acid such as hydrochloric acid to promote decarboxylation.

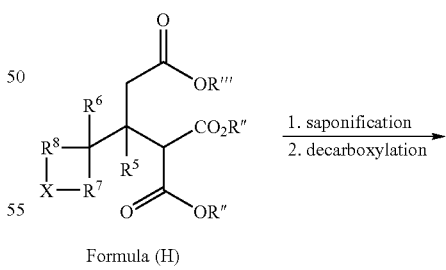

Formula (H)

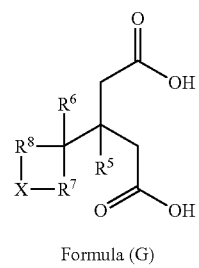

Formula (G)

A compound of Formula (H) may be prepared by reacting a compound of Formula (J) with a dialkyl malonate, such as dimethyl malonate or diethyl malonate, under basic conditions. Preferred bases include sodium alkoxide bases such as sodium methoxide and sodium ethoxide, and the reaction is preferably carried out in a solvent such as methanol, ethanol or toluene.

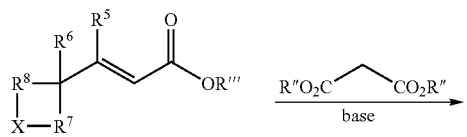

Formula (J)

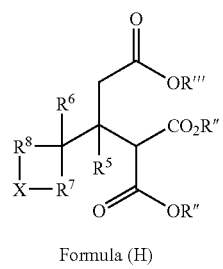

Formula (H)

Compounds of Formula (J) are known compounds, or may be prepared from known compounds by known methods.

A compound of Formula (B) wherein R and $R^5$ are both H may also be prepared via the hydrolysis and decarboxylation of a compound of Formula (K), which in turn may be prepared by addition of a dialkyl malonate (preferably dimethyl malonate or diethyl malonate) to a compound of Formula (L) in the presence of a suitable base, such as sodium methoxide or sodium ethoxide in a suitable solvent such as methanol, ethanol or toluene. A compound of Formula (L) may be prepared by the Knoevenagel condensation of an aldehyde of Formula (M) with a β-ketoester of Formula (N), where R'''' is alkyl, according to known procedures (see, for example, J. March, Advanced Organic Chemistry, $3^{rd}$ Edition, pp 835-841, John Wiley and Sons Inc. 1985). A compound of Formula (N) may be prepared from a compound of Formula (D), wherein R is H, through conversion to the corresponding acid chloride and subsequent reaction to give the β-ketoester of Formula (N) according to procedures described in the literature (see, for example, J. Wemple et al., Synthesis, (1993), 290-292; J. Bowman, J. Chem. Soc., (1950), 322).

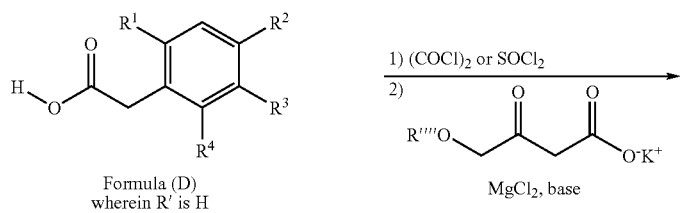

Formula (D)
wherein R' is H

Formula (N)

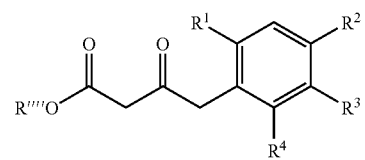

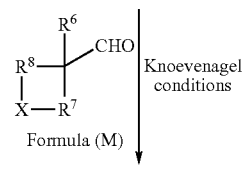

Formula (M)

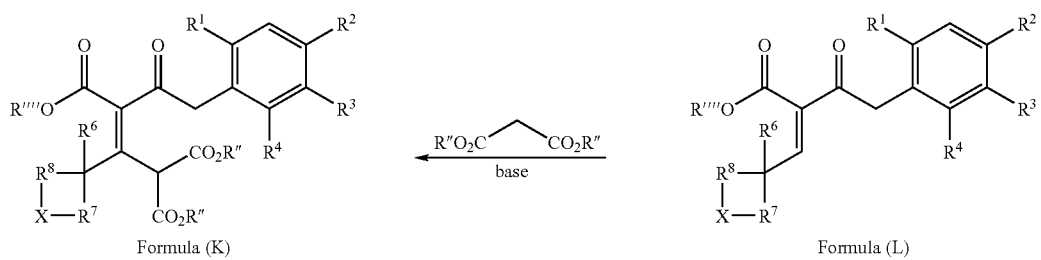

Formula (K)

Formula (L)

1. aqueous base
2. $H_3O^+$
   or NaCl, wet DMSO, Δ

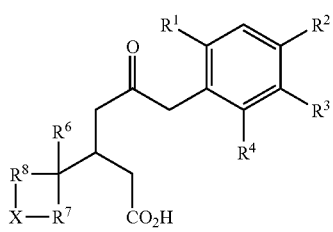

Formula (B) wherein both R and $R^5$ are H

Compounds of Formula (M) are known compounds, or may be prepared from known compounds by known methods.

Additional compounds of Formula (A) may be prepared by reacting a 2-diazocyclohexane-1,3-dione of Formula (O) with a compound of Formula (P) under known conditions. Suitable procedures include the photosensitised decomposition of diazoketones (see, for example, T. Wheeler, J. Org. Chem., (1979), 44, 4906), or by using a suitable metal catalyst such as rhodium acetate, copper chloride or copper triflate in a suitable solvent under known conditions (see, for example, M. Oda et al., Chem. Lett., (1987), 1263). Where compounds of Formula (P) are liquids at room temperature, these reactions may be effected in the absence of any solvent.

Compounds of Formula (P) are known, or may be prepared from known compounds by known methods.

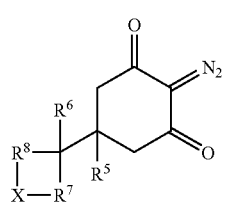

Formula (O)

+

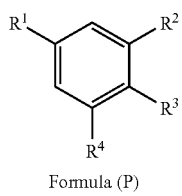

Formula (P)

metal catalyst or hv
solvent

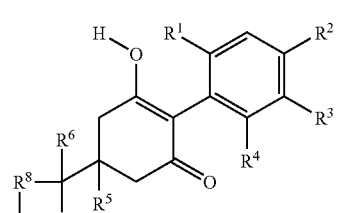

Formula (A)

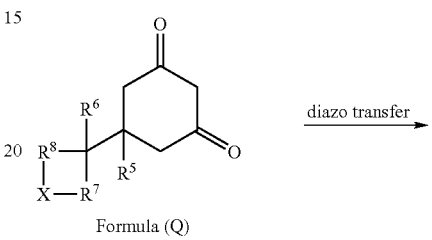

Formula (Q)

diazo transfer

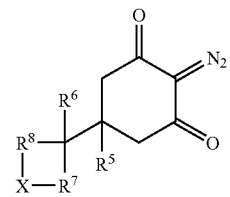

Formula (O)

A compound of Formula (Q) may be prepared via the hydrolysis and decarboxylation of a compound of Formula (R), under known conditions. Preferably R″ is methyl or ethyl.

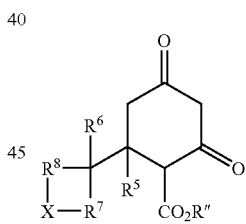

Formula (R)

(1) hydrolysis
(2) decarboxylation

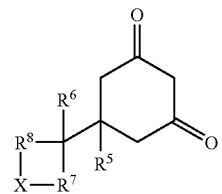

Formula (Q)

A compound of Formula (O) may be prepared through treatment of a compound of Formula (Q) with a diazo transfer reagent such as a tosyl azide or a mesyl azide and a base, as described, for example, by T. Ye and M. McKervey (Chem. Rev., (1994), 94, 1091-1160), by H. Stetter and K. Kiehs (Chem. Ber., (1965), 98, 1181) and by D. Taber et al. (J. Org. Chem., (1986), 51, 4077).

A compound of Formula (R) may be prepared by reacting a compound of Formula (S) with a dialkyl malonate under basic conditions. Preferably the dialkyl malonate is dimethyl malonate or diethyl malonate, the base is a metal alkoxide such as sodium methoxide or sodium ethoxide and the reaction is carried out in a suitable solvent such as methanol, ethanol or toluene.

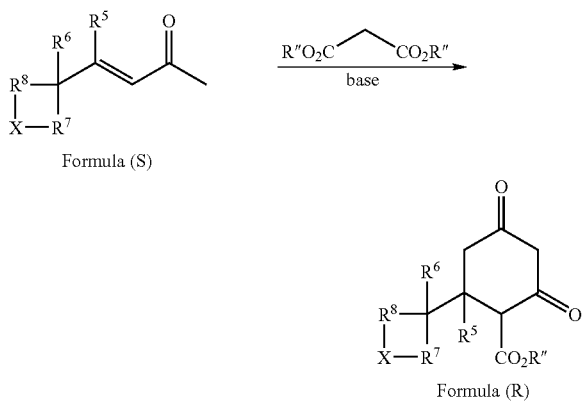

Formula (S)

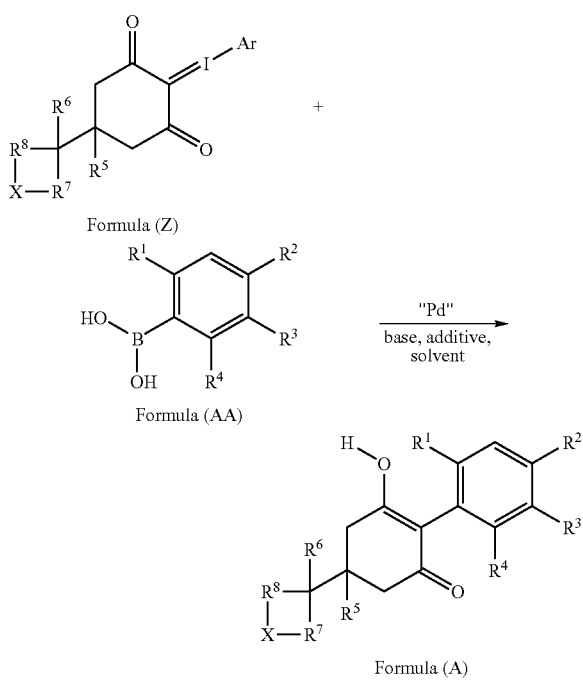

Formula (R)

Compounds of Formula (S) are known, or may be prepared by known methods from known compounds.

Additional compounds of Formula (A) may be prepared by reacting an iodonium ylide of Formula (Z), wherein Ar is an optionally substituted phenyl group, and an aryl boronic acid of Formula (AA) in the presence of a suitable palladium catalyst, a base and in a suitable solvent.

Formula (Z)

Formula (AA)

Formula (A)

Suitable palladium catalysts are generally palladium(II) or palladium(0) complexes, for example palladium(II) dihalides, palladium(II) acetate, palladium(II) sulfate, bis(triphenylphosphine)palladium(II) dichloride, bis(tricyclopentylphosphine)palladium(II) dichloride, bis(tricyclohexylphosphine)palladium(II) dichloride, bis(dibenzylideneacetone)palladium(0) or tetrakis(triphenylphosphine)palladium(0). The palladium catalyst can also be prepared "in situ" from palladium(II) or palladium(0) compounds by complexing with the desired ligands, by, for example, combining the palladium(II) salt to be complexed, for example palladium(II) dichloride (PdCl₂) or palladium(II) acetate (Pd(OAc)₂), together with the desired ligand, for example triphenylphosphine (PPh₃), tricyclopentylphosphine, tricyclohexylphosphine, 2-dicyclohexyl-phosphino-2',6'-dimethoxybiphenyl or 2-dicyclohexylphosphino-2',4',6'-triisopropylbiphenyl and the selected solvent, with a compound of Formula (Z), the arylboronic acid of Formula (AA), and a base. Also suitable are bidendate ligands, for example 1, 1'-bis(diphenylphosphino)ferrocene or 1,2-bis(diphenylphosphino)ethane. By heating the reaction medium, the palladium(II) complex or palladium(0) complex desired for the C—C coupling reaction is thus formed "in situ", and then initiates the C—C coupling reaction.

The palladium catalysts are used in an amount of from 0.001 to 50 mol %, preferably in an amount of from 0.1 to 15 mol %, based on the compound of Formula (Z). The reaction may also be carried out in the presence of other additives, such as tetralkylammonium salts, for example, tetrabutylammonium bromide. Preferably the palladium catalyst is palladium acetate, the base is lithium hydroxide and the solvent is aqueous 1,2-dimethoxyethane.

A compound of Formula (Z) may be prepared from a compound of Formula (Q) by treatment with a hypervalent iodine reagent such as a (diacetoxy)iodobenzene or an iodosylbenzene and a base such as aqueous sodium carbonate, lithium hydroxide or sodium hydroxide in a solvent such as water or an aqueous alcohol such as aqueous ethanol according to the procedures of K. Schank and C. Lick, Synthesis, (1983), 392, R. Moriarty et al, J. Am. Chem. Soc, (1985), 107, 1375, or of Z. Yang et al., Org. Lett., (2002), 4 (19), 3333.

An aryl boronic acid of Formula (AA) may be prepared from an aryl halide of Formula (BB), wherein Hal is bromine or iodine, by known methods (see, for example, W. Thompson and J. Gaudino, J. Org. Chem., (1984), 49, 5237 and R. Hawkins et al., J. Am. Chem. Soc., (1960), 82, 3053). For example, an aryl halide of Formula (BB) may be treated with an alkyl lithium or alkyl magnesium halide in a suitable solvent, preferably diethyl ether or tetrahydrofuran, at a temperature of between –80° C. and 30° C., and the aryl magnesium or aryl lithium reagent obtained may then be reacted with a trialkyl borate (preferably trimethylborate) to give an aryl dialkylboronate which may be hydrolysed to the desired boronic acid of Formula (AA) under acidic conditions.

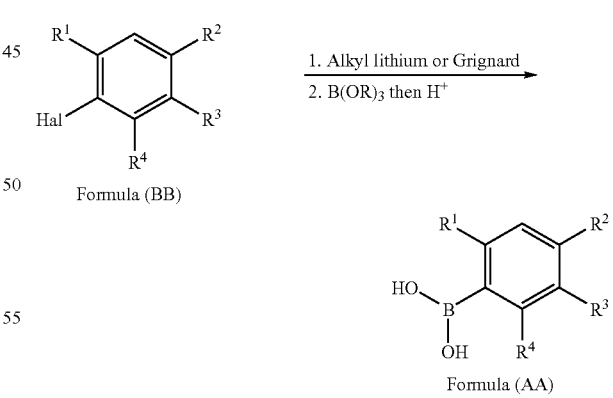

Formula (BB)

Formula (AA)

Alternatively a compound of Formula (BB) may be reacted with bis(pinacolato)diboron under known conditions (see, for example, N. Miyaura et al., J. Org. Chem., (1995), 60, 7508) and the resulting aryl boronate hydrolysed under acidic conditions to give a boronic acid of Formula (AA). Aryl halides of Formula (BB) may be prepared from anilines of Formula (CC) by known methods, for example the Sandmeyer reaction, via the corresponding diazonium salts.

Anilines of Formula (CC) are known compounds, or may be made from known compounds, by known methods.

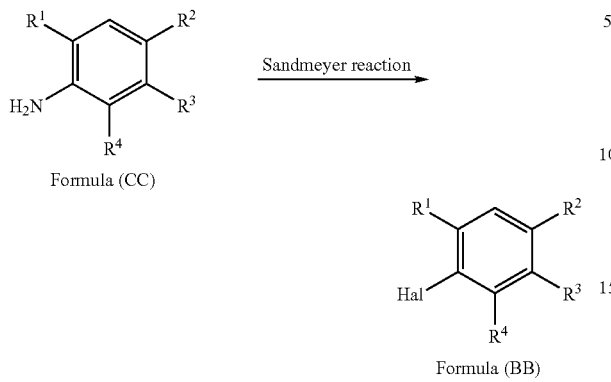

Formula (CC) → Formula (BB) (Sandmeyer reaction)

Additional compounds of Formula (A) wherein $R^2$ is optionally substituted aryl or heteroaryl may be prepared from compounds of Formula (DD) wherein X' is an atom or group suitable for cross-coupling with an aryl- or heteroaryl-boronic acid in the presence of a suitable palladium catalyst and a base under known conditions (see, for example F. Bellina, A. Carpita and R. Rossi, Synthesis, (2004), 15, 2419 and A. Suzuki, Journal of Organometallic Chemistry, (2002), 653, 83). Suitable atoms and groups X' include triflates, and halogens, especially chlorine, bromine and iodine.

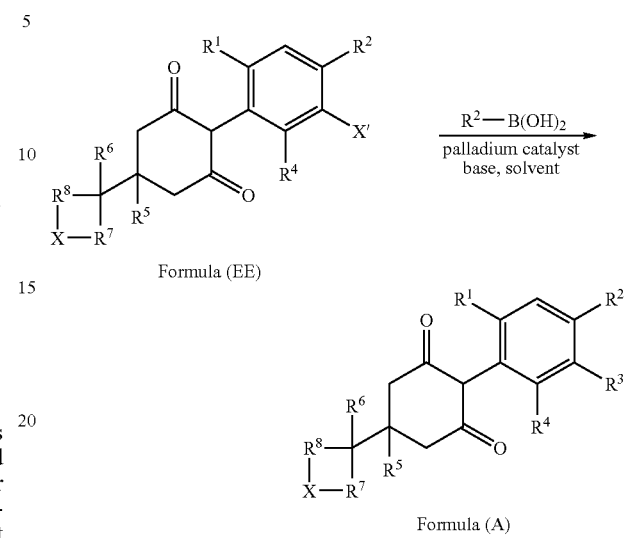

Similarly, a compound of Formula (A) wherein $R^3$ is optionally substituted aryl or heteroaryl may be prepared from a compound of Formula (EE) wherein X' is as defined previously and a suitable aryl- or heteroaryl-boronic acid under similar palladium catalysed conditions.

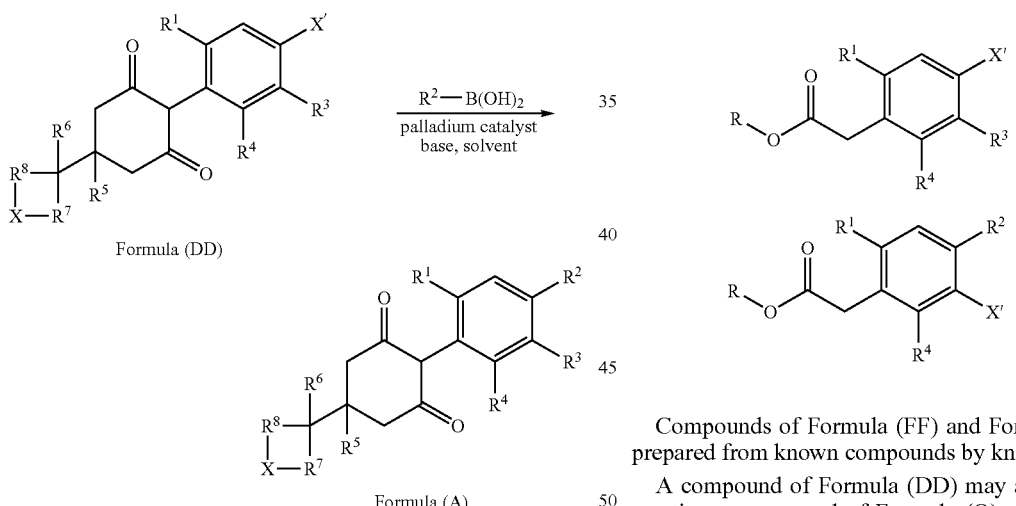

Compounds of Formula (DD) and Formula (EE) may be prepared from Compounds of Formula (FF) and Formula (GG) respectively, by one or more of the procedures described previously.

Compounds of Formula (FF) and Formula (GG) may be prepared from known compounds by known methods.

A compound of Formula (DD) may also be prepared by reacting a compound of Formula (O) with a compound of Formula (HH) under similar conditions to those described above for the conversion of a compound of Formula (O) to a compound of Formula (A).

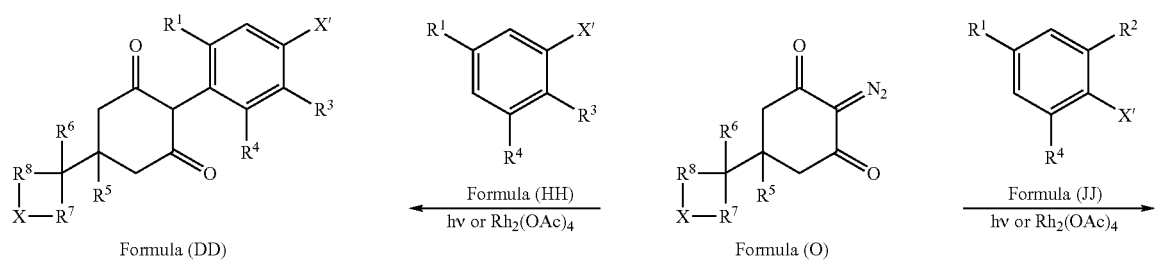

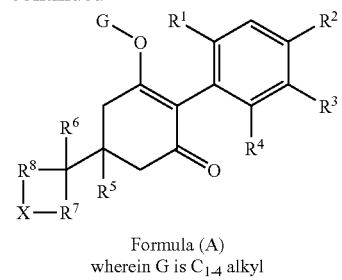

Formula (EE)

Similarly, a compound of Formula (EE) may be prepared from a compound of Formula (O) and a Compound of Formula (JJ) under similar conditions.

Additional compounds of Formula (I) wherein G is $C_{1-4}$ alkyl may be prepared by reacting a compound of Formula (KK), wherein G is $C_{1-4}$ alkyl and Hal is a halogen, preferably bromine or iodine, with an aryl boronic acid of Formula (AA) in the presence of a suitable palladium catalyst and a base and preferably in the presence of a suitable ligand, and in a suitable solvent. Preferably the palladium catalyst is palladium acetate, the base is potassium phosphate, the ligand is 2-dicyclohexylphosphino-2',6'-dimethoxybiphenyl and the solvent is toluene.

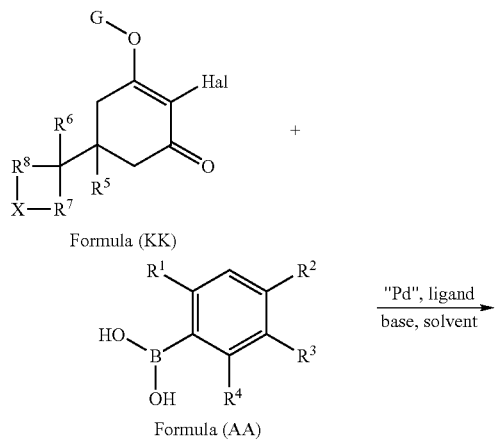

Formula (A)
wherein G is $C_{1-4}$ alkyl

A compound of Formula (KK) may be prepared by halogenating a compound of Formula (Q), followed by alkylation of the resulting halide of Formula (LL) with a $C_{1-4}$ alkyl halide or tri-$C_{1-4}$-alkylorthoformate under known conditions, for example by the procedures of R. Shepherd and A. White, J. Chem. Soc. Perkin Trans. 1 (1987), 2153, and Y.-L. Lin et al., Bioorg. Med. Chem. 10 (2002), 685. Alternatively, a compound of Formula (KK) may be prepared by alkylating a compound of Formula (Q) with a $C_{1-4}$ alkyl halide or a tri-$C_{1-4}$-alkylorthoformate, and halogenating the resulting enone of Formula (MM) under known conditions.

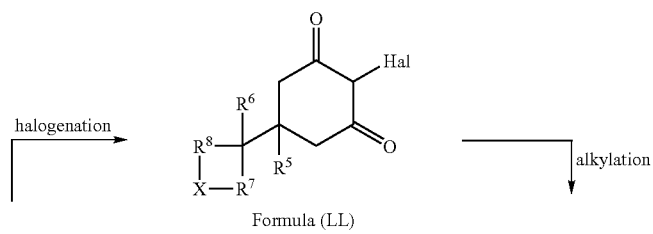

Formula (LL)

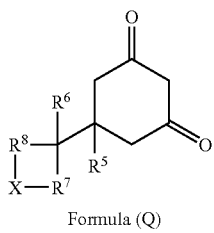

Formula (Q)

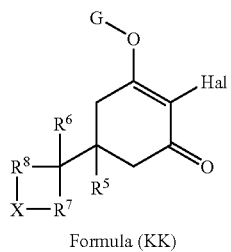

Formula (KK)

alkylation

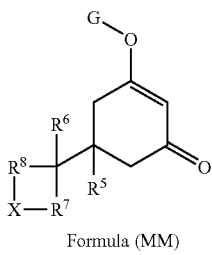

Formula (MM)

halogenation

A compound of Formula (I) wherein G is H may be prepared from a compound of Formula (I) wherein G is $C_{1-4}$ alkyl by hydrolysis, preferably in the presence of an acid catalyst such as hydrochloric acid and optionally in the presence of a suitable solvent such as tetrahydrofuran. Additional compounds of formula (A) may be prepared by reacting a compound of formula (Q) with an organolead reagent of formula (NN) under conditions described, for example, by J. Pinhey, Pure and Appl. Chem., (1996), Vol. 68 (4), 819, and by M. Moloney et al., Tetrahedron Lett., (2002), 43, 3407-3409.

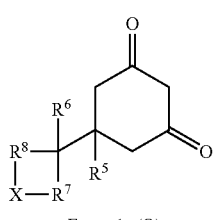

Formula (Q)

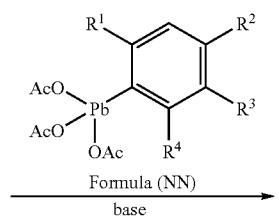

Formula (NN)
base

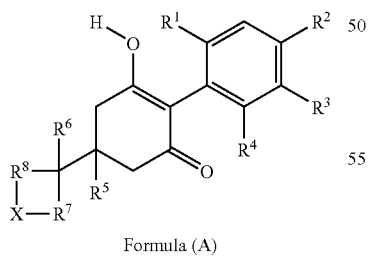

Formula (A)

The organolead reagent of formula (NN) may be prepared from a boronic acid of formula (Z) a stannane of formula (OO), wherein R is $C_1$-$C_4$ alkyl, or by direct plumbation of a compound of formula (PP) with lead tetraacetate according to known procedures.

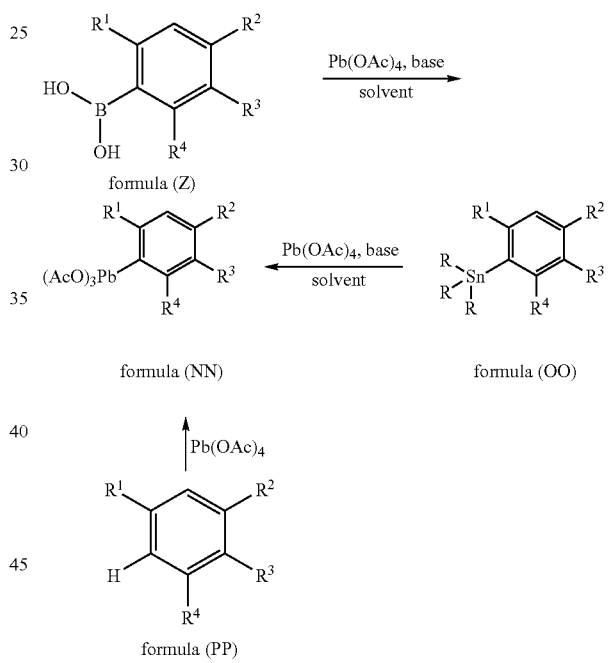

formula (Z)

formula (NN)

formula (OO)

formula (PP)

Further compounds of formula (A) may be prepared by reacting a compound of formula (Q) with a suitable triarylbismuth compound under conditions described, for example, by A. Yu. Fedorov et al., Russ. Chem. Bull. Int. Ed., (2005), 54 (11), 2602, and by P. Koech and M. Krische, J. Am. Chem. Soc., (2004), 126 (17), 5350 and references therein.

The compounds of Formula (I) according to the invention can be used as herbicides in unmodified form, as obtained in the synthesis, but they are generally formulated into herbicidal compositions in a variety of ways using formulation adjuvants, such as carriers, solvents and surface-active substances. The formulations can be in various physical forms, for example in the form of dusting powders, gels, wettable powders, water-dispersible granules, water-dispersible tablets, effervescent compressed tablets, emulsifiable concentrates, microemulsifiable concentrates, oil-in-water emulsions, oil flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known, for example, from the Manual on Development and Use of FAO Specifications for Plant Protection Products, 5th Edition, 1999. Such formulations can either be used directly or are diluted prior to use. Diluted formulations can be prepared, for example, with water, liquid fertilisers, micronutrients, biological organisms, oil or solvents.

The formulations can be prepared, for example, by mixing the active ingredient with formulation adjuvants in order to obtain compositions in the form of finely divided solids, granules, solutions, dispersions or emulsions. The active ingredients can also be formulated with other adjuvants, for example finely divided solids, mineral oils, vegetable oils, modified vegetable oils, organic solvents, water, surface-active substances or combinations thereof. The active ingredients can also be contained in very fine microcapsules consisting of a polymer. Microcapsules contain the active ingredients in a porous carrier. This enables the active ingredients to be released into their surroundings in controlled amounts (e.g. slow release). Microcapsules usually have a diameter of from 0.1 to 500 microns. They contain active ingredients in an amount of about from 25 to 95% by weight of the capsule weight. The active ingredients can be present in the form of a monolithic solid, in the form of fine particles in solid or liquid dispersion or in the form of a suitable solution. The encapsulating membranes comprise, for example, natural and synthetic gums, cellulose, styrene-butadiene copolymers, polyacrylonitrile, polyacrylate, polyester, polyamides, polyureas, polyurethane or chemically modified polymers and starch xanthates or other polymers that are known to the person skilled in the art in this connection. Alternatively it is possible for very fine microcapsules to be formed wherein the active ingredient is present in the form of finely divided particles in a solid matrix of a base substance, but in that case the microcapsule is not encapsulated.

The formulation adjuvants suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylenes carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethyl hexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol (PEG 400), propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and higher molecular weight alcohols, such as amyl alcohol, tetrahydrofurfuryl alcohol, hexanol, octanol, ethylene glycol, propylene glycol, glycerol, N-methyl-2-pyrrolidone and the like. Water is generally the carrier of choice for the dilution of the concentrates. Suitable solid carriers are, for example, talc, titanium dioxide, pyrophyllite clay, silica, attapulgite clay, kieselguhr, limestone, calcium carbonate, bentonite, calcium montomorillonite, cottonseed husks, wheatmeal, soybean flour, pumice, wood flour, ground walnut shells, lignin and similar materials, as described, for example, in CFR 180.1001. (c) & (d).

A large number of surface-active substances can advantageously be used both in solid and in liquid formulations, especially in those formulations which can be diluted with a carrier prior to use. Surface-active substances may be anionic, cationic, non-ionic or polymeric and they may be used as emulsifying, wetting or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol-alkylene oxide addition products, such as nonylphenol ethoxylate; alcohol-alkylene oxide addition products, such as tridecyl alcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride, polyethylene glycol esters of fatty acids, such as polyethylene glycol stearate; block copolymers of ethylene oxide and propylene oxide; and salts of mono- and di-alkyl phosphate esters; and also further substances described e.g. in "McCutcheon's Detergents and Emulsifiers Annual", MC Publishing Corp., Ridgewood, N.J., 1981.

Further adjuvants which can usually be used in pesticidal formulations include crystallisation inhibitors, viscosity-modifying substances, suspending agents, dyes, anti-oxidants, foaming agents, light absorbers, mixing aids, anti-foams, complexing agents, neutralising or pH-modifying substances and buffers, corrosion-inhibitors, fragrances, wetting agents, absorption improvers, micronutrients, plasticisers, glidants, lubricants, dispersants, thickeners, anti-freezes, microbiocides, and also liquid and solid fertilisers.

The formulations may also comprise additional active substances, for example further herbicides, herbicide safeners, plant growth regulators, fungicides or insecticides.

The compositions according to the invention can additionally include an additive comprising an oil of vegetable or animal origin, a mineral oil, alkyl esters of such oils or mixtures of such oils and oil derivatives. The amount of oil additive used in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsified vegetable oil, such as AMIGO® (Rhône-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being important. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000.

The application and action of the oil additives can be further improved by combining them with surface-active substances, such as non-ionic, anionic or cationic surfactants. Examples of suitable anionic, non-ionic and cationic surfactants are listed on pages 7 and 8 of WO 97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant AG). Also preferred are silicone surfactants, especially polyalkyl-oxide-modified heptamethyl-trisiloxanes, which are commercially available e.g. as Silwet L-77®, and also perfluorinated surfactants. The concentration of surface-active substances in relation to the total additive is generally from 1 to 30% by weight. Examples of oil additives that consist of mixtures of oils or mineral oils or derivatives thereof with surfactants are Edenor ME SU®, Turbocharge® (Syngenta AG, CH) and Actipron® (BP Oil UK Limited, GB).

The said surface-active substances may also be used in the formulations alone, that is to say without oil additives.

Furthermore, the addition of an organic solvent to the oil additive/surfactant mixture can contribute to a further enhancement of action. Suitable solvents are, for example, Solvesso® (ESSO) and Aromatic Solvent® (Exxon Corporation). The concentration of such solvents can be from 10 to 80% by weight of the total weight. Such oil additives, which may be in admixture with solvents, are described, for example, in U.S. Pat. No. 4,834,908. A commercially available oil additive disclosed therein is known by the name MERGE® (BASF Corporation). A further oil additive that is preferred according to the invention is SCORE® (Syngenta Crop Protection Canada.)

In addition to the oil additives listed above, in order to enhance the activity of the compositions according to the invention it is also possible for formulations of alkylpyrrolidones, (e.g. Agrimax®) to be added to the spray mixture. Formulations of synthetic latices, such as, for example, polyacrylamide, polyvinyl compounds or poly-1-p-menthene (e.g. Bond®, Courier® or Emerald®) can also be used. Solutions that contain propionic acid, for example Eurokem Pen-e-trate®, can also be mixed into the spray mixture as activity-enhancing agents.

The herbicidal formulations generally contain from 0.1 to 99% by weight, especially from 0.1 to 95% by weight, of a compound of formula I and from 1 to 99.9% by weight of a formulation adjuvant, which preferably includes from 0 to 25% by weight of a surface-active substance. Whereas commercial products will preferably be formulated as concentrates, the end user will normally employ dilute formulations.

The rate of application of the compounds of formula I may vary within wide limits and depends upon the nature of the soil, the method of application (pre- or post-emergence; seed dressing; application to the seed furrow; no tillage application etc.), the crop plant, the weed or grass to be controlled, the prevailing climatic conditions, and other factors governed by the method of application, the time of application and the target crop. The compounds of formula I according to the invention are generally applied at a rate of 1 to 4000 g/ha, especially from 5 to 1000 g/ha. Preferred formulations have especially the following compositions:

(%=percent by weight):

Emulsifiable Concentrates:

| active ingredient: | 1 to 95%, preferably 60 to 90% |
| surface-active agent: | 1 to 30%, preferably 5 to 20% |
| liquid carrier: | 1 to 80%, preferably 1 to 35% |

Dusts:

| active ingredient: | 0.1 to 10%, preferably 0.1 to 5% |
| solid carrier: | 99.9 to 90%, preferably 99.9 to 99% |

Suspension Concentrates:

| active ingredient: | 5 to 75%, preferably 10 to 50% |
| water: | 94 to 24%, preferably 88 to 30% |
| surface-active agent: | 1 to 40%, preferably 2 to 30% |

Wettable Powders:

| active ingredient: | 0.5 to 90%, preferably 1 to 80% |
| surface-active agent: | 0.5 to 20%, preferably 1 to 15% |
| solid carrier: | 5 to 95%, preferably 15 to 90% |

Granules:

| active ingredient: | 0.1 to 30%, preferably 0.1 to 15% |
| solid carrier: | 99.5 to 70%, preferably 97 to 85% |

The following Examples further illustrate, but do not limit, the invention.

| F1. Emulsifiable concentrates | a) | b) | c) | d) |
|---|---|---|---|---|
| active ingredient | 5% | 10% | 25% | 50% |
| calcium dodecylbenzene-sulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP | — | — | 10% | 20% |
| arom. hydrocarbon mixture $C_9$-$C_{12}$ | 85% | 78% | 55% | 16% |

Emulsions of any desired concentration can be prepared from such concentrates by dilution with water.

| F2. Solutions | a) | b) | c) | d) |
|---|---|---|---|---|
| active ingredient | 5% | 10% | 50% | 90% |
| 1-methoxy-3-(3-methoxy-propoxy)-propane | — | 20% | 20% | — |
| polyethylene glycol MW 400 | 20% | 10% | — | — |
| NMP | — | — | 30% | 10% |
| arom. hydrocarbon mixture $C_9$-$C_{12}$ | 75% | 60% | — | — |

The solutions are suitable for application in the form of microdrops.

| F3. Wettable powders | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly disperse silicic acid | 1% | 3% | 5% | 10% |
| kaolin | 88% | 62% | 35% | — |

The active ingredient is thoroughly mixed with the adjuvants and the mixture is thoroughly ground in a suitable mill, yielding wettable powders which can be diluted with water to give suspensions of any desired concentration.

| F4. Coated granules | a) | b) | c) |
|---|---|---|---|
| active ingredient | 0.1% | 5% | 15% |
| highly disperse silicic acid | 0.9% | 2% | 2% |
| inorg. carrier (diameter 0.1-1 mm) e.g. $CaCO_3$ or $SiO_2$ | 99.0% | 93% | 83% |

The active ingredient is dissolved in methylene chloride, the solution is sprayed onto the carrier and the solvent is subsequently evaporated off in vacuo.

| F5. Coated granules | a) | b) | c) |
|---|---|---|---|
| active ingredient | 0.1% | 5% | 15% |
| polyethylene glycol MW 200 | 1.0% | 2% | 3% |
| highly disperse silicic acid | 0.9% | 1% | 2% |
| inorg. carrier (diameter 0.1-1 mm) e.g. $CaCO_3$ or $SiO_2$ | 98.0% | 92% | 80% |

The finely ground active ingredient is applied uniformly, in a mixer, to the carrier moistened with polyethylene glycol. Non-dusty coated granules are obtained in this manner.

| F6. Extruder granules | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants and the mixture is moistened with water. The resulting mixture is extruded and then dried in a stream of air.

| F7. Dusts | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F8. Suspension concentrates | a) | b) | c) | d) |
|---|---|---|---|---|
| active ingredient | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, yielding a suspension concentrate from which suspensions of any desired concentration can be prepared by dilution with water.

The invention relates also to a method for the selective control of grasses and weeds in crops of useful plants, which comprises treating the useful plants or the area under cultivation or the locus thereof with a compound of formula I.

Crops of useful plants in which the compositions according to the invention can be used include especially cereals, cotton, soybeans, sugar beet, sugar cane, plantation crops, rape, maize and rice, and for non-selective weed control. The term "crops" is to be understood as also including crops that have been rendered tolerant to herbicides or classes of herbicides (for example ALS, GS, EPSPS, PPO, ACCase and HPPD inhibitors) as a result of conventional methods of breeding or genetic engineering. An example of a crop that has been rendered tolerant e.g. to imidazolinones, such as imazamox, by conventional methods of breeding is Clearfield® summer rape (Canola). Examples of crops that have been rendered tolerant to herbicides by genetic engineering methods include e.g. glyphosate- and glufosinate-resistant maize varieties commercially available under the trade names RoundupReady® and LibertyLink®. The weeds to be controlled may be both monocotyledonous and dicotyledonous weeds, such as, for example, *Stellaria, Nasturtium, Agrostis, Digitaria, Avena, Setaria, Sinapis, Lolium, Solanum, Echinochloa, Scirpus, Monochoria, Sagittaria, Bromus, Alopecurus, Sorghum, Rottboellia, Cyperus, Abutilon, Sida, Xanthium, Amaranthus, Chenopodium, Ipomoea, Chrysanthemum, Galium, Viola* and *Veronica*.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt-176 maize hybrids of NK® (Syngenta Seeds). The Bt toxin is a protein that is formed naturally by *Bacillus thuringiensis* soil bacteria. Examples of toxins and transgenic plants able to synthesise such toxins are described in EP-A-451 878, EP-A-374 753, WO 93/07278, WO 95/34656, WO 03/052073 and EP-A-427 529. Examples of transgenic plants that contain one or more genes which code for an insecticidal resistance and express one or more toxins are KnockOut® (maize), Yield Gard® (maize), NuCOTIN33B®(cotton), Bollgard® (cotton), NewLeaf® (potatoes), NatureGard® and Protexcta®. Plant crops and their seed material can be resistant to herbicides and at the same time also to insect feeding ("stacked" transgenic events). Seed can, for example, have the ability to express an insecticidally active Cry3 protein and at the same time be glyphosate-tolerant. The term "crops" is to be understood as also including crops obtained as a result of conventional methods of breeding or genetic engineering which contain so-called output traits (e.g. improved flavour, storage stability, nutritional content).

Areas under cultivation are to be understood as including land where the crop plants are already growing as well as land intended for the cultivation of those crop plants.

The compounds of Formula (I) according to the invention can also be used in combination with one or more other herbicides. In particular, the following mixtures of the compound of Formula (I) are important. Preferably, the compound of the Formula (I) is a compound listed in Tables 1 to 35 below:

compound of Formula (I)+acetochlor, compound of Formula (I)+acifluorfen, compound of Formula (I)+acifluorfen-sodium, compound of Formula (I)+aclonifen, compound of Formula (I)+acrolein, compound of Formula (I)+alachlor, compound of Formula (I)+alloxydim, compound of Formula (I)+allyl alcohol, compound of Formula (I)+ametryn, compound of Formula (I)+amicarbazone, compound of Formula (I)+amidosulfuron, compound of Formula (I)+aminopyralid, compound of Formula (I)+amitrole, compound of Formula (I)+ammonium sulfamate, compound of Formula (I)+anilofos, compound of Formula (I)+asulam, compound of Formula (I)+atraton, compound of Formula (I)+atrazine, compound of Formula (I)+azimsulfuron, compound of Formula (I)+BCPC, compound of Formula (I)+beflubutamid, compound of Formula (I)+benazolin, compound of Formula (I)+benfluralin, compound of Formula (I)+benfuresate, compound of Formula (I)+bensulfuron, compound of Formula (I)+bensulfuron-methyl, compound of Formula (I)+bensulide, compound of Formula (I)+bentazone, compound of Formula (I)+benzfendizone, compound of Formula (I)+benzobicyclon, compound of Formula (I)+benzofenap, compound of Formula (I)+bifenox, compound of Formula (I)+bilanafos, compound of Formula (I)+bispyribac, compound of Formula (I)+bispyribac-sodium, compound of Formula (I)+borax, compound of Formula (I)+bromacil, compound of Formula (I)+bromobutide, compound of Formula (I)+bromoxynil, compound of Formula (I)+butachlor, compound of Formula (I)+butafenacil, compound of Formula (I)+butamifos, compound of Formula (I)+butralin, compound of Formula (I)+butroxydim, compound of Formula (I)+butylate, compound of Formula (I)+cacodylic acid, compound of Formula (I)+calcium chlorate, compound of Formula (I)+cafenstrole, compound of Formula (I)+carbetamide, compound of Formula (I)+carfentrazone, compound of Formula (I)+carfentrazone-ethyl, compound of Formula (I)+CDEA, compound of Formula (I)+CEPC, compound of Formula (I)+chlorflurenol, compound of Formula (I)+chlorflurenol-methyl, compound of Formula (I)+chloridazon, compound of Formula (I)+chlorimuron, compound of Formula (I)+chlorimuron-ethyl, compound of Formula (I)+chloroacetic acid, compound of Formula (I)+chlorotoluron, compound of Formula (I)+chlorpropham, compound of Formula (I)+chlorsulfuron, compound of Formula (I)+chlorthal, compound of Formula (I)+chlorthal-dimethyl, compound of Formula (I)+cinidon-ethyl, compound of Formula (I)+cinmethylin, compound of Formula (I)+cinosulfuron, compound of Formula (I)+cisanilide, compound of Formula (I)+clethodim, compound of Formula (I)+clodinafop, compound of Formula (I)+clodinafop-propargyl, compound of Formula (I)+clomazone, compound of Formula (I)+clomeprop, compound of Formula (I)+clopyralid, compound of Formula (I)+cloransulam, compound of Formula (I)+cloransulam-methyl, compound of Formula (I)+CMA, compound of Formula (I)+4-CPB, compound of Formula (I)+CPMF, compound of Formula (I)+4-CPP, compound of Formula (I)+CPPC, compound of Formula (I)+cresol, compound of Formula (I)+cumyluron, compound of Formula (I)+cyanamide, compound of Formula (I)+cyanazine, compound of Formula (I)+cycloate, compound of Formula (I)+cyclosulfamuron, compound of Formula (I)+cycloxydim, compound of Formula (I)+cyhalofop, compound of Formula (I)+cyhalofop-butyl, compound of Formula (I)+2,4-D, compound of Formula (I)+3,4-DA, compound of Formula (I)+daimuron, compound of Formula (I)+dalapon, compound of Formula (I)+dazomet, compound of Formula (I)+2,4-DB, compound of Formula (I)+3,4-DB, compound of Formula (I)+2,4-DEB, compound of Formula (I)+desmedipham, compound of Formula (I)+dicamba, compound of Formula (I)+dichlobenil, compound of Formula (I)+ortho-dichlorobenzene, compound of Formula (I)+para-dichlorobenzene, compound of Formula (I)+dichlorprop, compound of Formula (I)+dichlorprop-P, compound of Formula (I)+diclofop, compound of Formula (I)+diclofop-methyl, compound of Formula (I)+diclosulam, compound of Formula (I)+difenzoquat, compound of Formula (I)+difenzoquat metilsulfate, compound of Formula (I)+diflufenican, compound of Formula (I)+diflufenzopyr, compound of Formula (I)+dimefuron, compound of Formula (I)+dimepiperate, compound of Formula (I)+dimethachlor, compound of Formula (I)+dimethametryn, compound of Formula (I)+dimethenamid, compound of Formula (I)+dimethenamid-P, compound of Formula (I)+dimethipin, compound of Formula (I)+dimethylarsinic acid, compound of Formula (I)+dinitramine, compound of Formula (I)+dinoterb, compound of Formula (I)+diphenamid, compound of Formula (I)+diquat, compound of Formula (I)+diquat dibromide, compound of Formula (I)+dithiopyr, compound of Formula (I)+diuron, compound of Formula (I)+DNOC, compound of Formula (I)+3,4-DP, compound of Formula (I)+DSMA, compound of Formula (I)+EBEP, compound of Formula (I)+endothal, compound of Formula (I)+EPTC, compound of Formula (I)+esprocarb, compound of Formula (I)+ethalfluralin, compound of Formula (I)+ethametsulfuron, compound of Formula (I)+ethametsulfuron-methyl, compound of Formula (I)+ethofumesate, compound of Formula (I)+ethoxyfen, compound of Formula (I)+ethoxysulfuron, compound of Formula (I)+etobenzanid, compound of Formula (I)+fenoxaprop-P, compound of Formula (I)+fenoxaprop-P-ethyl, compound of Formula (I)+fentrazamide, compound of Formula (I)+ferrous sulfate, compound of Formula (I)+flamprop-M, compound of Formula (I)+flazasulfuron, compound of Formula (I)+florasulam, compound of Formula (I)+fluazifop, compound of Formula (I)+fluazifop-butyl, compound of Formula (I)+fluazifop-P, compound of Formula (I)+fluazifop-P-butyl, compound of Formula (I)+flucarbazone, compound of Formula (I)+flucarbazone-sodium, compound of Formula (I)+flucetosulfuron, compound of Formula (I)+fluchloralin, compound of Formula (I)+flufenacet, compound of Formula (I)+flufenpyr, compound of Formula (I)+flufenpyr-ethyl, compound of Formula (I)+flumetsulam, compound of Formula (I)+flumiclorac, compound of Formula (I)+flumiclorac-pentyl, compound of Formula (I)+flumioxazin, compound of Formula (I)+fluometuron, compound of Formula (I)+fluoroglycofen, compound of Formula (I)+fluoroglycofen-ethyl, compound of Formula (I)+flupropanate, compound of Formula (I)+flupyrsulfuron, compound of Formula (I)+flupyrsulfuron-methyl-sodium, compound of Formula (I)+flurenol, compound of Formula (I)+fluridone, compound of Formula (I)+fluorochloridone, compound of Formula (I)+fluoroxypyr, compound of Formula (I)+flurtamone, compound of Formula (I)+fluthiacet, compound of Formula (I)+fluthiacet-methyl, compound of Formula (I)+fomesafen, compound of Formula (I)+foramsulfuron, compound of Formula (I)+fosamine, compound of Formula (I)+glufosinate, compound of Formula (I)+glufosinate-ammonium, compound of Formula (I)+glyphosate, compound of Formula (I)+halosulfuron, compound of Formula (I)+halosulfuron-methyl, compound of Formula (I)+haloxyfop, compound of Formula (I)+haloxyfop-P, compound of Formula (I)+HC-252, compound of Formula (I)+hexazinone, compound of Formula (I)+imazamethabenz, compound of Formula (I)+imazamethabenz-methyl, compound of Formula (I)+imazamox, compound of Formula (I)+imazapic, compound of Formula (I)+imazapyr, compound of Formula (I)+imazaquin, compound of Formula (I)+imazethapyr, compound of Formula (I)+imazosulfuron, compound of Formula (I)+indanofan, compound of Formula (I)+iodomethane, compound of Formula (I)+iodosulfuron, compound of Formula (I)+iodosulfuron-methyl-sodium, compound of Formula (I)+ioxynil, compound of Formula (I)+isoproturon, compound of Formula (I)+isouron, compound of Formula (I)+isoxaben, compound of Formula (I)+isoxachlortole, compound of Formula (I)+isoxaflutole, compound of Formula (I)+karbutilate, compound of Formula (I)+lactofen, compound of Formula (I)+lenacil, compound of Formula (I)+linuron, compound of Formula (I)+MAA, compound of Formula (I)+MAMA, compound of Formula (I)+MCPA, compound of Formula (I)+MCPA-thioethyl, compound of Formula (I)+MCPB, compound of Formula (I)+mecoprop, compound of Formula (I)+mecoprop-P, compound of Formula (I)+mefenacet, compound of Formula (I)+mefluidide, compound of Formula (I)+mesosulfuron, compound of Formula (I)+mesosulfuron-methyl, compound of Formula (I)+mesotrione, compound of Formula (I)+metam, compound of Formula (I)+metamifop, compound of Formula (I)+metamitron, compound of Formula (I)+metazachlor, compound of Formula (I)+methabenzthiazuron, compound of Formula (I)+methylarsonic acid, compound of Formula (I)+methyldymron, compound of Formula (I)+methyl isothiocyanate, compound of Formula (I)+metobenzuron, compound of Formula (I)+metolachlor, compound of Formula (I)+S-metolachlor, compound of Formula (I)+metosulam, compound of Formula (I)+metoxuron, compound of Formula (I)+metribuzin, compound of Formula (I)+metsulfuron, compound of Formula (I)+metsulfuron-methyl, compound of Formula (I)+MK-616, compound of Formula (I)+molinate, compound of Formula (I)+monolinuron, compound of Formula (I)+MSMA, compound of Formula (I)+naproanilide, compound of Formula (I)+napropamide, compound of Formula (I)+naptalam, compound of Formula (I)+neburon, compound of Formula (I)+nicosulfuron, compound of Formula (I)+nonanoic acid, compound of Formula (I)+norflurazon, compound of Formula (I)+oleic acid (fatty acids), compound of Formula (I)+orbencarb, compound of Formula (I)+orthosulfamuron, compound of Formula (I)+oryzalin, compound of Formula (I)+oxadiargyl, compound of Formula (I)+oxadiazon, compound of Formula (I)+oxasulfuron, compound of Formula (I)+oxaziclomefone, compound of Formula (I)+oxyfluorfen, compound of Formula (I)+paraquat, compound of Formula (I)+paraquat dichloride, compound of Formula (I)+pebulate, compound of Formula (I)+pendimethalin, compound of Formula (I)+penoxsulam, compound of Formula (I)+pentachlorophenol, compound of Formula (I)+pentanochlor, compound of Formula (I)+pentoxazone, compound of Formula (I)+pethoxamid, compound of Formula (I)+petrolium oils, compound of Formula (I)+phenmedipham, compound of Formula (I)+phenmedipham-ethyl, compound of Formula (I)+picloram, compound of Formula (I)+picolinafen, compound of Formula (I)+pinoxaden, compound of Formula (I)+piperophos, compound of Formula (I)+potassium arsenite, compound of Formula (I)+potassium azide, compound of Formula (I)+pretilachlor, compound of Formula (I)+primisulfuron, compound of Formula (I)+primisulfuron-methyl, compound of Formula (I)+prodiamine, compound of Formula (I)+profluazol, compound of Formula (I)+profoxydim, compound of Formula (I)+prometon, compound of Formula (I)+prometryn, compound of Formula (I)+propachlor, compound of Formula (I)+propanil, compound of Formula (I)+propaquizafop, compound of Formula (I)+propazine, compound of Formula (I)+propham, compound of Formula (I)+propisochlor, compound of Formula (I)+propoxycarbazone, compound of Formula (I)+propoxycarbazone-sodium, compound of Formula (I)+propyzamide, compound of Formula (I)+prosulfocarb, compound of Formula (I)+prosulfuron, compound of Formula (I)+pyraclonil, compound of Formula (I)+pyraflufen, compound of Formula (I)+pyraflufen-ethyl, compound of Formula (I)+pyrazolynate, compound of Formula (I)+pyrazosulfuron, compound of Formula (I)+pyrazosulfuron-ethyl, compound of Formula (I)+pyrazoxyfen, compound of Formula (I)+pyribenzoxim, compound of Formula (I)+pyributicarb, compound of Formula (I)+pyridafol, compound of Formula (I)+pyridate, compound of Formula (I)+pyriftalid, compound of Formula (I)+pyriminobac, compound of Formula (I)+pyriminobac-methyl, compound of Formula (I)+pyrimisulfan, compound of Formula (I)+pyrithiobac, compound of Formula (I)+pyrithiobac-sodium, compound of Formula (I)+quinclorac, compound of Formula (I)+quinmerac, compound of Formula (I)+quinoclamine, compound of Formula (I)+quizalofop, compound of Formula (I)+quizalofop-P, compound of Formula (I)+rimsulfuron, compound of Formula (I)+sethoxydim, compound of Formula (I)+siduron, compound of Formula (I)+simazine, compound of Formula (I)+simetryn, compound of Formula (I)+SMA, compound of Formula (I)+sodium arsenite, compound of Formula (I)+sodium azide, compound of Formula (I)+sodium chlorate, compound of Formula (I)+sulcotrione, compound of Formula (I)+sulfentrazone, compound of Formula (I)+sulfometuron, compound of Formula (I)+sulfometuron-methyl, compound of Formula (I)+sulfosate, compound of Formula (I)+sulfosulfuron, compound of Formula (I)+sulfuric acid, compound of Formula (I)+tar oils, compound of Formula (I)+2,3,6-TBA, compound of Formula (I)+TCA, compound of Formula (I)+TCA-sodium, compound of Formula (I)+tebuthiuron, compound of Formula (I)+tepraloxydim, compound of Formula (I)+terbacil, compound of Formula (I)+terbumeton, compound of Formula (I)+terbuthylazine, compound of Formula (I)+terbutryn, compound of Formula (I)+thenylchlor, compound of Formula (I)+thiazopyr, compound of Formula (I)+thifensulfuron, compound of Formula (I)+thifensulfuron-methyl, compound of Formula (I)+thiobencarb, compound of Formula (I)+tiocarbazil, compound of Formula (I)+topramezone, compound of Formula (I)+tralkoxydim, compound of Formula (I)+tri-allate, compound of Formula (I)+triasulfuron, compound of Formula (I)+triaziflam, compound of Formula (I)+tribenuron, compound of Formula (I)+tribenuron-methyl, compound of Formula (I)+tricamba, compound of Formula (I)+triclopyr, compound of Formula (I)+trietazine, compound of Formula (I)+trifloxysulfuron, compound of Formula (I)+trifloxysulfuron-sodium, compound of Formula (I)+trifluralin, compound of Formula (I)+triflusulfuron, compound of Formula (I)+triflusulfuron-methyl, compound of Formula (I)+trihydroxytriazine, compound of Formula (I)+tritosulfuron, compound of Formula (I)+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6), compound of Formula (I)+4-[(4,5-dihydro-3-methoxy-4-methyl-5-oxo)-1H-1,2,4-triazol-1-ylcarbonylsulfamoyl]-5-methylthiophene-3-carboxylic acid (BAY636), compound of Formula (I)+BAY747 (CAS RN 335104-84-2), compound of Formula (I)+topramezone (CAS RN 210631-68-8), compound of Formula (I)+4-hydroxy-3-[[2-[(2-methoxyethoxy)methyl]-6-(trifluoromethyl)-3-pyridinyl]carbonyl]-bicyclo[3.2.1]oct-3-en-2-one (CAS RN 352010-68-5), and compound of Formula (I)+4-hydroxy-3-[[2-(3-methoxypropyl)-6-(difluoromethyl)-3-pyridinyl]carbonyl]-bicyclo[3.2.1]oct-3-en-2-one.

The mixing partners of the compound of Formula (I) may also be in the form of esters or salts, as mentioned e.g. in The Pesticide Manual, 12th Edition (BCPC), 2000.

The mixing ratio of the compound of Formula (I) to the mixing partner is preferably from 1:100 to 1000:1.

The mixtures can advantageously be used in the above-mentioned formulations (in which case "active ingredient" relates to the respective mixture of compound of Formula (I) with the mixing partner).

The compounds of Formula (I) according to the invention can also be used in combination with safeners. Preferably, in these mixtures, the compound of the Formula (I) is one of those compounds listed in Tables 1 to 35 below. The following mixtures with safeners, especially, come into consideration:
compound of Formula (I)+cloquintocet-mexyl, compound of Formula (I)+cloquintocet acid and salts thereof, compound of Formula (I)+fenchlorazole-ethyl, compound of Formula (I)+fenchlorazole acid and salts thereof, compound of Formula (I)+mefenpyr-diethyl, compound of Formula (I)+mefenpyr diacid, compound of Formula (I)+isoxadifen-ethyl, compound of Formula (I)+isoxadifen acid, compound of Formula (I)+furilazole, compound of Formula (I)+furilazole R isomer, compound of Formula (I)+benoxacor, compound of Formula (I)+dichlormid, compound of Formula (I)+AD-67, compound of Formula (I)+oxabetrinil, compound of Formula (I)+cyometrinil, compound of Formula (I)+cyometrinil Z-isomer, compound of Formula (I)+fenclorim, compound of Formula (I)+cyprosulfamide, compound of Formula (I)+naphthalic anhydride, compound of Formula (I)+flurazole, compound of formula (I)+N-(2-methoxybenzoyl)-4-[(methylaminocarbonyl)amino]benzenesulfonamide, compound of Formula (I)+CL 304,415, compound of Formula (I)+dicyclonon, compound of Formula (I)+fluxofenim, compound of Formula (I)+DKA-24, compound of Formula (I)+R-29148 and compound of Formula (I)+PPG-1292. A safening effect can also be observed for the mixtures compound of the Formula (I)+dymron, compound of the Formula (I)+MCPA, compound of the Formula (I)+mecopropand compound of the Formula (I)+mecoprop-P.

The above-mentioned safeners and herbicides are described, for example, in the Pesticide Manual, Twelfth Edition, British Crop Protection Council, 2000. R-29148 is described, for example by P. B. Goldsbrough et al., Plant Physiology, (2002), Vol. 130 pp. 1497-1505 and references therein, PPG-1292 is known from WO09211761, and N-(2-methoxybenzoyl)-4-[(methylaminocarbonyl)amino]benzenesulfonamide is known from EP365484.

The compounds of Formula (I) according to the invention can also be used in combination with the co-herbicides and safeners mentioned above to form a three-way mixture containing a compound of the Formula (I), a co-herbicide and a safener.

The following Examples illustrate the invention further but do not limit the invention.

PREPARATION EXAMPLES

Example 1

Preparation of 2-(2,6-diethyl-4-methylphenyl)-5-(tetrahydropyran-4-yl)cyclohexane-1,3-dione Compound T2 in Table T1

Step 1

Methoxymethyltriphenylphosphonium chloride (81.8 g) is suspended in dry THF (200 ml) and stirred under nitrogen at 0° C. A 1 molar solution of lithium bis(trimethylsilyl)amide in THF (239 ml) is transferred to a dropping funnel by cannular under nitrogen and added over 20 minutes. The resulting red-brown solution is stirred at 0-20° C. for 1 hour. The mixture is then cooled to −25° C. and tetrahydro-4H-pyran-4-one (20 ml) is added over 10 minutes. The cooling bath is removed and the mixture is allowed to reach room temperature, then stirred for 22 hours. The reaction mixture is poured into water (400 ml) and extracted into ether (2×400 ml). The organic extracts are combined, washed with water (2×400 ml) and brine (400 ml), dried over anhydrous magnesium sulphate, filtered and the filtrate is concentrated in vacuo. The residue is treated with 800 ml ether:hexane (1:1), stirred for 15 mins, then cooled in an ice bath for 10 mins and filtered under vacuum to remove the precipitated triphenylphosphine oxide. The filtrate is concentrated, treated again with 400 ml ether:hexane (1:1), stirred for 15 minutes, then cooled in an ice bath and additional precipitate is removed by filtration. The filtrate is concentrated giving 25.371 g of a brown oil. The crude material is purified by vacuum distillation to afford 4-(methoxymethylene)tetrahydropyran (b.p. 66° C./20 mmHg).

Step 2

A mixture of 4-(methoxymethylene)tetrahydropyran (17.18 g, 134 mmol) and toluene-4-sulphonic acid hydrate (35.76 g, 188 mmol) in a mixture of water (90 ml) and THF (90 ml) is stirred at room temperature for 4½ hours. The mixture is treated with a saturated aqueous solution of NaHCO$_3$ (300 ml) and stirred until effervescence ceased. The mixture is transferred to a separating funnel, brine (100 ml) was added, and the reaction is extracted into dichloromethane (4×150 ml). The organic extracts are combined, dried over anhydrous magnesium sulphate, filtered and the filtrate concentrated in vacuo to afford tetrahydropyran-4-carboxaldehyde.

Step 3

To a solution of tetrahydropyran-4-carboxaldehyde (12.0 g, 105 mmol) in dichloromethane (300 ml) is added triphenylphosphoranylidene-2-propanone (33.43 g, 105 mmol) in one portion. The reaction mixture is heated to reflux for 16 hours. The reaction mixture is cooled and concentrated in vacuo. Hexane (300 ml) is added to the residue, and the mixture is stirred and then filtered under vacuum. The solid is suspended in hexane (100 ml), stirred and then filtered and the remaining solid discarded. The filtrates are combined and concentrated in vacuo giving a yellow oil. The oil is dissolved in dichloromethane (250 ml), triphenylphosphoranylidene-2-propanone (9.55 g, 30 mmol) is added and the mixture was heated at reflux for a further 7 days.

The reaction mixture is concentrated in vacuo, and hexane (300 ml) added. The mixture is stirred for a few minutes, filtered and the filtrate evaporated in vacuo. Purification by column chromatography on silica gel eluting with a mixture of ethyl acetate and hexane, on silica gel gives 4-(tetrahydropyran-4-yl)-3-buten-2-one.

Step 4

Diethylmalonate (8.86 ml, 58 mmol) is added dropwise over 3 minutes to a chilled (ice-bath) solution of sodium (1.48 g, 64 mmol) in ethanol (80 ml). Once the addition is complete the cooling bath is removed and reaction is stirred for 25 minutes at room temperature, then the reaction mixture is cooled again in an ice-bath. A solution of 4-(tetrahydropyran-4-yl)-3-buten-2-one (7.50 g, 49 mmol) in ethanol (45 ml) is added to the reaction mixture via a dropping funnel over 15 minutes. Once the addition is complete, the cooling bath is removed and the yellow solution is stirred at room temperature for 19 hours. The reaction mixture is acidified to pH 3 by dropwise addition of 2M aqueous hydrochloric acid, water added to dissolve the precipitate and the reaction mixture is extracted into dichloromethane. The organic extracts are dried over anhydrous magnesium sulphate, filtered and the filtrate concentrated in vacuo. The residue is taken up in isopropanol (50 ml) and a 2M aqueous solution of sodium hydroxide (140 ml) added. The reaction mixture is stirred at room temperature for 20 hours. The reaction mixture is concentrated in vacuo to remove isopropanol, then heated to 70° C. A solution of 2M aqueous hydrochloric acid is added carefully until the reaction mixture reaches pH 2. The reaction mixture is heated for 2½ hours at 75° C., then cooled to room temperature and the product is extracted into ethyl acetate. The organic extracts are combined, dried over anhydrous magnesium sulphate, filtered and the filtrate concentrated in vacuo to give 5-(tetrahydropyran-4-yl)cyclohexane-1,3-dione.

Step 5

A solution of 5-(tetrahydropyran-4-yl)cyclohexane-1,3-dione (1.50 g, 7.64 mmol) and sodium carbonate (0.81 g, 7.64 mol) in water (20 ml) is added dropwise to a suspension of iodobenzene diacetate (2.46 g, 7.64 mmol) and sodium carbonate (0.81 g, 7.64 mmol) in water (25 ml) and the mixture is stirred at room temperature for 3½ hours. The iodonium ylide (2.186 g) is collected by filtration.

Step 6

A portion of the ylide (0.70 g, 1.76 mmol) prepared in step 5, 2,6-diethyl-4-methylphenylboronic acid (0.372 g, 1.93 mmol), palladium acetate (0.02 g, 0.09 mmol), tetrabutylammonium bromide (0.583 g, 1.76 mmol) and lithium hydroxide monohydrate (0.222 g, 5.28 mmol) are added to a mixture of 1,2-dimethoxyethane (20 ml) and water (5 ml) and the mixture is heated at 50° C. for 5¾ hours. The mixture is cooled to room temperature, filtered through diatomaceous earth to remove the catalyst, and the filtrate is partitioned between ethyl acetate and water. The organic extracts are combined, dried over anhydrous magnesium sulphate, filtered and the filtrate is evaporated in vacuo. The residue is further purified by column chromatography on silica gel, eluting with a mixture of ethyl acetate and hexane to give 2-(2,6-diethyl-4-methylphenyl)-5-(tetrahydropyran-4-yl)cyclohexane-1,3-dione.

$^1$H NMR data (CDCl$_3$, ppm): $\delta_H$ 6.98 (s, 2H), 5.54 (br s, 1H), 4.04 (d, 2H), 3.40 (t, 2H), 2.71-2.64 (m, 2H), 2.47-2.23 (m, 9H), 2.11-2.00 (m, 1H), 1.72-1.69 (m, 2H), 1.60 (m, 1H), 1.50-1.35 (m, 2H), 1.08 (m, 6H)

Example 2

Preparation of 2-(2,6-diethyl-4-methylphenyl)-5-(tetrahydrofuran-3-yl)cyclohexane-1,3-dione Compound T4 in Table T1

Step 1

Dimethyl (2-oxopropyl)phosphonate (32.06 g, 193 mmol) is added to a chilled (ice-bath) solution of potassium hydroxide (10.83 g, 193 mmol) in water (30 ml) and ethanol (170 ml) and the mixture is stirred. Tetrahydrofuran-3-carboxaldehyde (50% wt. % solution in water, 25 ml, 138 mmol) is added dropwise and the reaction mixture is stirred at 5° C. for 10 minutes. The cooling bath is removed and the mixture is stirred at room temperature for 7 hours. Most of the solvent is removed in vacuo, water (100 ml) and diethyl ether (200 ml) are added, the mixture is poured into a separating funnel and the organic phase collected. The aqueous phase is extracted three times with diethyl ether, and the organic extracts are combined, dried over anhydrous magnesium sulphate, filtered and the filtrate is evaporated in vacuo. The residue is further purified by column chromatography on silica gel, eluting with a mixture of ethyl acetate and hexane to give 4-(tetrahydrofuran-3-yl)-3-buten-2-one as a pale yellow liquid.

Step 2

Diethyl malonate (6.50 ml, 43 mmol) is added dropwise to a cooled (ice-bath) solution of sodium (1.07 g, 46 mmol) in anhydrous ethanol (60 ml) and once the addition is complete the cooling bath is removed and the reaction mixture is stirred at room temperature for 25 minutes. The mixture is cooled in an ice bath and a solution of 4-(tetrahydrofuran-3-yl)-3-buten-2-one (5.0 g, 36 mmol) in ethanol (30 ml) is added dropwise. Once the addition is complete the cooling bath is removed and the reaction mixture is stirred at room temperature for 19 hours. The reaction mixture is acidified to pH 3 by dropwise addition of 2M aqueous hydrochloric acid, water added to dissolve any precipitate formed and the reaction mixture is extracted into dichloromethane. The organic extracts are dried over anhydrous magnesium sulphate, filtered and the filtrate is concentrated in vacuo to afford a yellow oil which is taken up in isopropanol (35 ml) and a 2M aqueous solution of sodium hydroxide (100 ml) is added. The reaction mixture is stirred at room temperature for 20 hours. The reaction mixture is concentrated in vacuo to remove isopropanol then heated to 70° C. A solution of 2M aqueous hydrochloric acid is added carefully until the reaction mixture reached pH 1. The reaction mixture is heated for 1½ hours at 70° C., then cooled to room temperature, diluted with water and the product is extracted into ethyl acetate. The organic extracts are combined, dried over anhydrous magnesium sulphate, filtered and the filtrate is concentrated in vacuo to give 5-(tetrahydrofuran-3-yl)cyclohexane-1,3-dione as a yellow solid.

Step 3

A solution of 5-(tetrahydrofuran-3-yl)cyclohexane-1,3-dione (1.82 g, 10 mmol) and sodium carbonate (1.06 g, 10 mol) in water (25 ml) is added dropwise to a suspension of iodobenzene diacetate (3.22 g. 10 mmol) and sodium carbonate (1.06 g, 10 mmol) in water (35 ml) and stirred at room temperature for 3½ hours. The mixture is partitioned between brine and dichloromethane and the organic extract is dried over anhydrous magnesium sulphate, filtered and the filtrate evaporated to give a yellow foam. The residue is taken up in diethyl ether and the ether evaporated to give the desired iodonium ylide as a yellow solid.

Step 4

A portion of the ylide (0.85 g, 2.21 mmol), 2,6-diethyl-4-methylphenylboronic acid (0.467 g, 2.43 mmol), palladium acetate (0.025 g, 0.11 mmol), tetrabutylammonium bromide (0.734 g, 2.21 mmol) and lithium hydroxide monohydrate (0.278 g, 6.63 mmol) are added to a mixture of 1,2-dimethoxyethane (24 ml) and water (6 ml) and the mixture is heated at 50° C. for 5¾ hours. The mixture is cooled to room temperature, filtered through diatomaceous earth to remove the catalyst, and the filtrate is partitioned between ethyl acetate and water. The organic extracts are combined, dried over anhydrous magnesium sulphate, filtered and the filtrate is evaporated in vacuo. The residue is further purified by column chromatography on silica gel, eluting with a mixture of ethyl acetate and hexane to give 2-(2,6-diethyl-4-methylphenyl)-5-(tetrahydrofuran-3-yl)cyclohexane-1,3-dione.

$^1$H NMR data (CDCl$_3$, ppm): $\delta_H$ 6.94 (s, 2H), 3.93-3.89 (t, 1H), 3.87-3.83 (m, 1H), 3.76-3.70 (q, 1H), 3.44-3.39 (t, 1H), 2.64-2.62 (m, 1H), 2.53-2.48 (m, 1H), 2.28 (s, 3H), 2.34-2.24 (m, 6H), 2.21-2.12 (m, 1H), 2.11-1.99 (m, 2H), 1.65-1.55 (m, 1H), 1.05-1.01 (m, 6H)

Example 3

Preparation of 2-(3,5-dimethylbiphen-4-yl)-5-(tetrahydropyran-4-yl)cyclohexane-1,3-dione Compound T26 in Table T1

To a mixture of 5-(tetrahydropyran-4-yl)cyclohexane-1,3-dione (196 mg; 1 mmol) and 4-dimethylaminopyridine (610 mg; 5 mmol) is added dry chloroform (4 ml) under an atmosphere of nitrogen, and the mixture is stirred at room temperature until all the solids are dissolved. To this solution is then added dry toluene (2 ml) and a solution of 3,5-dimethylbiphen-4-yllead triacetate (1.2 mmol) in chloroform. The reaction mixture is heated under reflux for 1 hour. The reaction mixture is cooled to room temperature, acidified to pH 1 with 2N aqueous hydrochloric acid, filtered and the filtrate is extracted with dichloromethane (2×40 ml). The organic extracts are combined, dried over anhydrous magnesium sulfate, filtered and the filtrate is evaporated in vacuo. The residue is purified by column chromatography on silica gel to give 2-(3,5-dimethylbiphen-4-yl)-5-(tetrahydropyran-4-yl)cyclohexane-1,3-dione.

$^1$H NMR data (CDCl$_3$, ppm): $\delta_H$ 7.58 (d, 2H), 7.43 (dd, 2H); 7.34 (d, 1H), 7.33 (s, 2H), 5.92 (br s, 1H), 4.03 (m, 2H), 3.39 (m, 2H), 2.69 (m, 2H), 2.44 (dd, 1H), 2.26 (dd, 1H), 2.17 (s, 3H), 2.13 (s, 3H), 2.09 (m, 1H), 1.70 (m, 2H), 1.56 (m, 1H), 1.43 (m, 2H)

Compounds in Table T1 below are prepared by similar methods using appropriate starting materials.

TABLE T1

| Compound Number | Structure | $^1$H NMR—CDCl$_3$ unless stated |
|---|---|---|
| T1 | 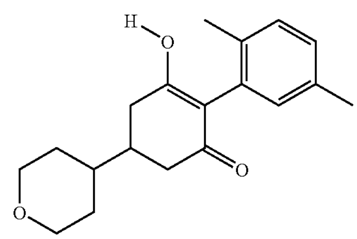 [SMILES: Cc1ccc(C)c(C2=C(O)CC(C3CCOCC3)CC2=O)c1] | δ 7.17 (dd, 1H), 7.08 (d, 1H), 6.86 (s, 1H), 5.30 (br s, 1H), 4.03 (dd, 2H), 3.39 (t, 2H), 2.68-2.62 (m, 2H), 2.35-2.26 (m, 5H), 2.08-1.99 (m, 4H), 1.68 (d, 2H), 1.59-1.51 (m, 1H), 1.45-1.34 (m, 2H) |
| T2 | 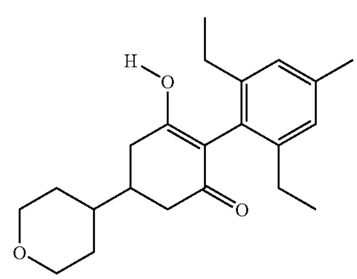 [SMILES: CCc1cc(C)cc(CC)c1C1=C(O)CC(C2CCOCC2)CC1=O] | δ 6.98 (s, 2H), 5.54 (br s, 1H), 4.04 (d, 2H), 3.40 (t, 2H), 2.71-2.64 (m, 2H), 2.47-2.23 (m, 9H), 2.11-2.00 (m, 1H), 1.72-1.69 (m, 2H), 1.60 (m, 1H), 1.50-1.35 (m, 2H), 1.08 (m, 6H) |

TABLE T1-continued

| Compound Number | Structure | ¹H NMR—CDCl₃ unless stated |
|---|---|---|
| T3 | 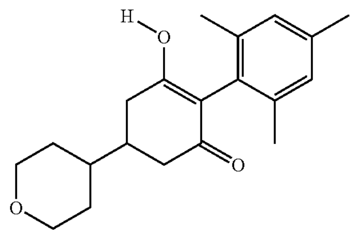 [SMILES: Cc1cc(C)c(C2=C(O)CC(C3CCOCC3)CC2=O)c(C)c1] | δ 6.94 (s, 2H), 5.55 (s, 1H), 4.04 (d, 2H), 3.40 (t, 2H), 2.70-2.63 (m, 2H), 2.46-2.39 (m, 1H), 2.28 (s, 3H), 2.25-2.21 (m, 1H), 2.07 (s, 3H), 2.03 (s, 3H), 2.11-2.01 (m, 1H), 1.70 (d, 2H), 1.62-1.56 (m, 1H), 1.48-1.34 (m, 2H) |
| T4 | 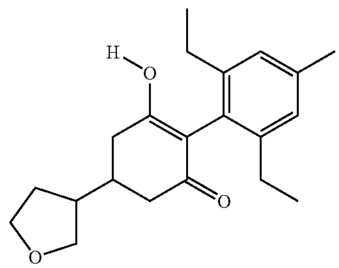 [SMILES: CCc1cc(C)cc(CC)c1C1=C(O)CC(C2CCOC2)CC1=O] | δ 6.94 (s, 2H), 3.93-3.89 (t, 1H), 3.87-3.83 (m, 1H), 3.76-3.70 (q, 1H), 3.44-3.39 (t, 1H), 2.64-2.62 (m, 1H), 2.53-2.48 (m, 1H), 2.28 (s, 3H), 2.34-2.24 (m, 6H), 2.21-2.12 (m, 1H), 2.11-1.99 (m, 2H), 1.65-1.55 (m, 1H), 1.05-1.01 (m, 6H) |
| T5 | 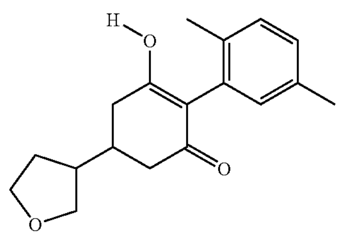 [SMILES: Cc1ccc(C)c(C2=C(O)CC(C3CCOC3)CC2=O)c1] | δ 7.18 (d, 1H), 7.09 (d, 1H), 6.86 (s, 1H), 5.79 (br d, 1H), 4.01-3.96 (m, 1H), 3.95-3.89 (m, 1H), 3.82-3.76 (m, 1H), 3.52-3.43 (m, 1H), 2.73-2.62 (m, 1H), 2.59-2.39 (m, 3H), 2.29 (s, 3H), 2.34-2.04 (m, 6H), 1.70-1.58 (m, 1H) |
| T6 | 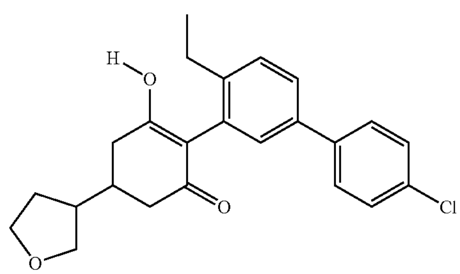 [SMILES: CCc1ccc(-c2ccc(Cl)cc2)cc1C1=C(O)CC(C2CCOC2)CC1=O] | δ 7.55-7.37 (m, 6H), 7.22 (m, 1H), 5.75 (br d, 1H), 4.02-3.97 (m, 1H), 3.95-3.90 (m, 1H), 3.83-3.77 (m, 1H), 3.55-3.45 (m, 1H), 2.74-2.68 (m, 1H), 2.62-2.09 (m, 7H), 1.72-1.58 (m, 2H), 1.16-1.11 (m, 3H) |
| T7 | 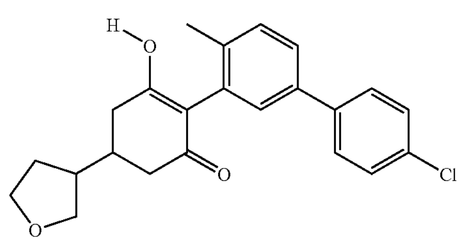 [SMILES: Cc1ccc(-c2ccc(Cl)cc2)cc1C1=C(O)CC(C2CCOC2)CC1=O] | δ 7.48 (d, 3H), 7.37 (d, 3H), 7.24 (m, 1H), 5.89 (br s, 1H), 3.99 (m, 1H), 3.92 (t, 1H), 3.79 (q, 1H), 3.49 (m, 1H), 2.73-2.66 (m, 1H), 2.61-2.43 (m, 2H), 2.36-2.11 (m, 7H), 1.71-1.58 (m, 1H) |
| T8 | 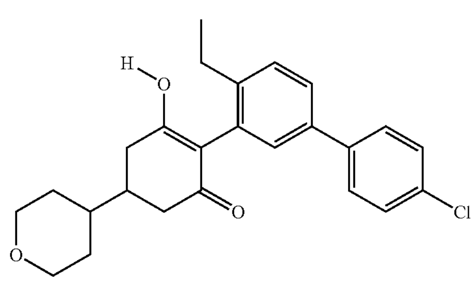 [SMILES: CCc1ccc(-c2ccc(Cl)cc2)cc1C1=C(O)CC(C2CCOCC2)CC1=O] | δ 7.51-7.46 (m, 3H), 7.38-7.35 (m, 3H), 7.20-7.19 (m, 1H), 6.36 (br s, 1H), 3.98 (dd, 2H), 3.35 (m, 2H), 2.63 (m, 2H), 2.44-2.13 (br m, 4H), 2.08-2.00 (m, 1H), 1.65-1.62 (m, 2H), 1.56-1.47 (m, 1H), 1.40-1.31 (m, 2H), 1.11 (q, 3H) |

TABLE T1-continued

| Compound Number | Structure | ¹H NMR—CDCl₃ unless stated |
|---|---|---|
| T9 | 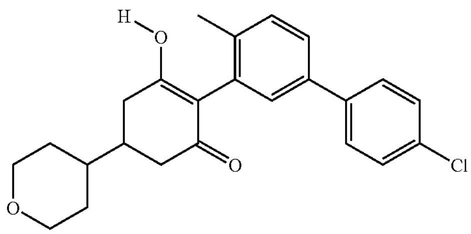 [SMILES: Cc1ccc(-c2ccc(Cl)cc2)cc1C1=C(O)CC(C2CCOCC2)CC1=O] | δ 7.48-7.45 (m, 3H), 7.38-7.33 (m, 3H), 7.24-7.23 (m, 1H), 6.14 (br s, 1H), 4.01 (dd, 2H), 3.37 (t, 2H), 2.64 (m, 2H), 2.41 (m, 1H), 2.13 (m, 1H), 2.12 (d, 3H), 2.08-2.04 (m, 1H), 1.67-1.64 (m, 2H), 1.56-1.49 (m, 1H), 1.39 (m, 2H) |
| T10 | 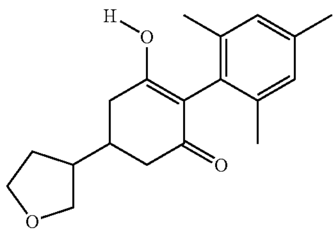 [SMILES: Cc1cc(C)c(C2=C(O)CC(C3CCOC3)CC2=O)c(C)c1] | δ 6.94 (s, 2H), 5.55 (dd, 1H), 4.01-3.96 (m, 1H), 3.95-3.89 (m, 1H), 3.83-3.76 (m, 1H), 3.49 (m, 1H), 2.73-2.67 (m, 1H), 2.61-2.41 (m, 2H), 2.27 (s, 3H), 2.34-2.08 (m, 4H), 2.05 (s, 3H), 2.02 (s, 3H), 1.71-1.61 (m, 1H) |
| T11 | 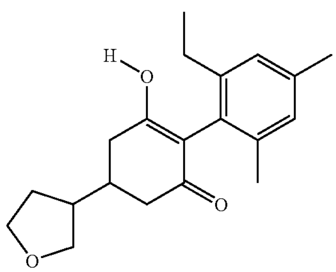 [SMILES: CCc1cc(C)cc(C)c1C1=C(O)CC(C2CCOC2)CC1=O] | δ 6.97 (m, 2H), 5.59 (d, 1H), 4.02-3.98 (1H, m), 3.84-3.77 (1H, m), 3.55-3.46 (m, 1H), 2.73-2.68 (m, 1H), 2.61-2.44 (m, 2H), 2.30 (s, 3H), 2.41-2.10 (m, 5H), 2.05-2.02 (m, 4H), 1.74-1.62 (m, 1H), 1.10-1.05 (m, 3H) |
| T12 | 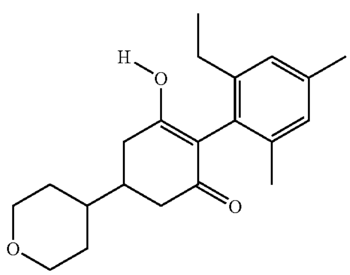 [SMILES: CCc1cc(C)cc(C)c1C1=C(O)CC(C2CCOCC2)CC1=O] | δ 6.97 (s, 2H), 5.57 (s, 1H), 4.04 (d, 2H), 3.40 (t, 2H), 2.69-2.64 (m, 2H), 2.30 (s, 3H), 2.49-2.20 (m, 4H), 2.11-2.02 (m, 4H), 1.72-1.68 (m, 2H), 1.60 (m, 1H), 1.48-1.36 (m, 2H), 1.10-1.05 (m, 3H) |
| T13 | 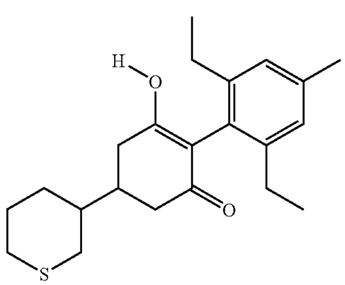 [SMILES: CCc1cc(C)cc(CC)c1C1=C(O)CC(C2CCCSC2)CC1=O] | δ 7.00 (2 s, 2H), 2.67 (m, 4H), 2.55 (m, 2H), 2,45 (m, 2H), 2,35 (m, 7H), 2.17 (m, 2H), 1.95 (m, 1H), 1.75 (m, 2H), 1.55 (m, 1H), 1.05 (2 t, 6H) |
| T14 | 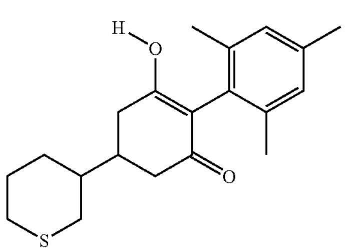 [SMILES: Cc1cc(C)c(C2=C(O)CC(C3CCCSC3)CC2=O)c(C)c1] | δ 6.94 (s, 2H), 5.55 (bs, 1H), 2.65 (m, 2H), 2.58 (m, 3H), 2.47 (m, 2H), 2.28 (s, 3H), 2.20 (m, 2H), 2.1 (m, 1H), 2.06 (2 t, 6H), 1.92 (m, 1H), 1.76 (m, 2H), 1.25 (m, 1H) |

TABLE T1-continued

| Compound Number | Structure | ¹H NMR—CDCl₃ unless stated |
|---|---|---|
| T15 | 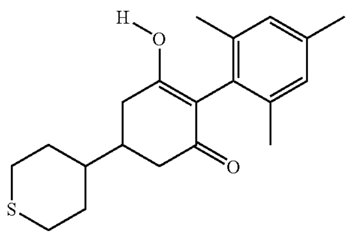 [SMILES: Cc1cc(C)c(C2=C(O)CC(C3CCSCC3)CC2=O)c(C)c1] | δ 6.94 (s, 2H), 5.50 (s, 1H), 2.69 (m, 4H), 2.58 (m, 2H), 2.48 (m, 1H), 2.29 (m, 1H), 2.28 (s, 3H), 2.10 (m, 3H), 2.06 (s, 3H), 2.02 (s, 3H), 1.49 (m, 2H), 1.43 (m, 1H) |
| T16 | 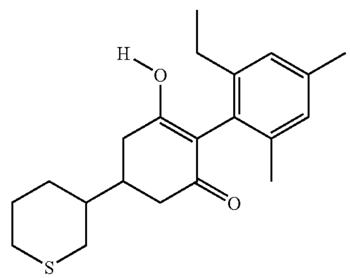 [SMILES: CCc1cc(C)cc(C)c1C1=C(O)CC(C2CCCSC2)CC1=O] | δ 6.96 (2 s, 2H), 5.60 (br s, 1H), 2.64 (m, 5H), 2.58 (m, 2H), 2.48 (m, 2H), 2.30 (s, 3H), 2.20 (m, 4H), 2.06 (s, 2H), 1.94 (m, 1H), 1.74 (m, 2H), 1.24 (m, 1H), 1.08 (2 t, 3H) |
| T17 | 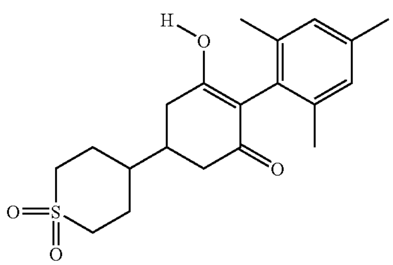 [SMILES: Cc1cc(C)c(C2=C(O)CC(C3CCS(=O)(=O)CC3)CC2=O)c(C)c1] | δ 6.90 (s, 2H), 5.60 (s, 1H), 3.15 (m, 2H), 3.00 (m, 2H), 2.70 (m, 2H), 2.50 (m, 1H), 2.30 (m, 1H), 2.25 (s, 3H), 2.20 (m, 3H), 2.00 (m, 8H), 1.6 (m, 1H) |
| T18 | 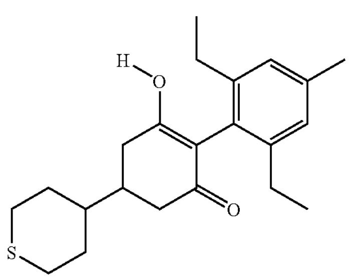 [SMILES: CCc1cc(C)cc(CC)c1C1=C(O)CC(C2CCSCC2)CC1=O] | δ 6.98 (s, 2H), 5.48 (br s, 1H), 2.69 (m, 4H), 2.59 (m, 2H), 2.47 (m, 2H), 2.33 (m, 7H), 2.12 (m, 3H), 1.53 (m, 2H), 1.43 (m, 1H), 1.08 (t, 6H) |
| T19 | 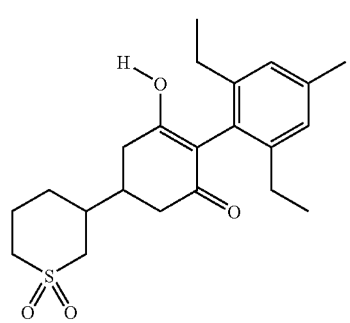 [SMILES: CCc1cc(C)cc(CC)c1C1=C(O)CC(C2CCCS(=O)(=O)C2)CC1=O] | δ 6.99 (s, 2H), 5.67 (s, 1H), 3.12 (m, 2H), 2.92-2.76 (m, 2H), 2.62 (m, 3H), 2.37 (m, 2H), 2.33 (s, 3H), 2.27 (m, 8H), 2.08 (m, 1H), 1.08 (2 t, 6H) |

TABLE T1-continued

| Compound Number | Structure | ¹H NMR—CDCl₃ unless stated |
|---|---|---|
| T20 | 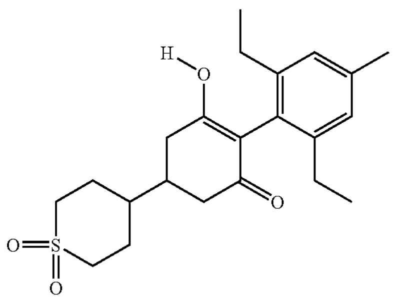 [SMILES: CCc1cc(C)cc(CC)c1C1=C(O)CC(C2CCS(=O)(=O)CC2)CC1=O] | δ 6.99 (s, 2H), 5.57 (s, 1H), 3.12 (m, 4H), 2.64 (m, 2H), 2.50 (m, 1H), 2.33 (m, 7H), 2.21 (m, 4H), 2.05 (m, 2H), 1.62 (m, 1H), 1.07 (2 t, 6H) |
| T21 | 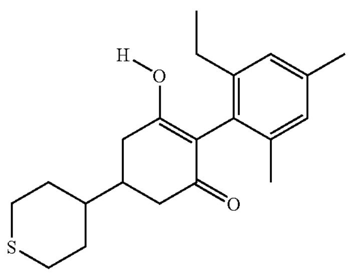 [SMILES: CCc1cc(C)cc(C)c1C1=C(O)CC(C2CCSCC2)CC1=O] | δ 6.96 (s, 1H), 6.95 (s, 1H), 5.53 (s, 1H), 2.61 (m, 4H), 2.59 (m, 2H), 2.50-2.25 (m, 5H), 2.30 (s, 3H), 2.10 (m, 3H), 2.04 (m, 2H), 1.53 (m, 2H), 1.42 (m, 1H), 1.08 (2 t, 3H) |
| T22 | 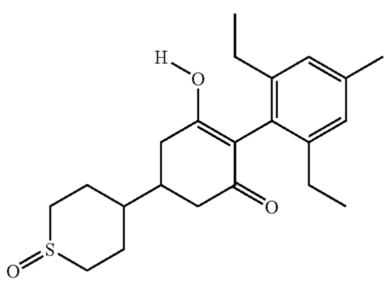 [SMILES: CCc1cc(C)cc(CC)c1C1=C(O)CC(C2CCS(=O)CC2)CC1=O] | δ 6.99 (s, 2H) 5.95 (2 × s, 1H), 3.39 (m, 1H), 3.08 (m, 1H), 2.66 (m, 3H), 2.38 (m, 2H), 2.35-2.13 (m, 12H), 1.84 (m, 1H), 1.58 (m, 1H), 1.08 (m, 6H) |
| T23 | 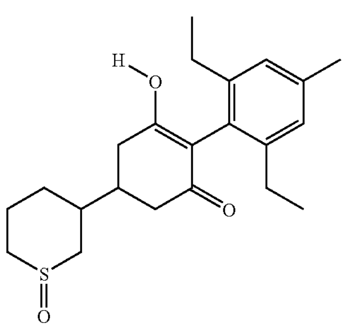 [SMILES: CCc1cc(C)cc(CC)c1C1=C(O)CC(C2CCCS(=O)C2)CC1=O] | δ 6.99 (s, 2H) 5.74 (3 s, 1H) 3.47 (2 × s, 1H) 3.13-2.99 (m, 1H) 2.72-2.57 (m, 3H) 2.57-2 39 (m, 3H) 2.39-2.29 (m, 9H) 2.29-2.17 (m, 1H) 2.02-1.87 (m, 1H) 1.86-1.74 (m, 1H) 1.40-1.17 (m, 1H) 1.10 (m, 6H) |
| T24 | 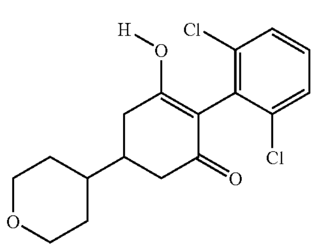 [SMILES: O=C1CC(C2CCOCC2)CC(O)=C1c1c(Cl)cccc1Cl] | δ 9.52 (br s, 1H), 7.34 (m, 2H), 7.18 (m, 1H), 4.05 (m, 2H), 3.40 (m, 2H), 2.67 (br, s, 2H), 2.35 (m, 1H), 2.06 (m, 1H), 1.70 (m, 2H), 1.60 (m, 1H), 1.41 (m, 2H) |

TABLE T1-continued

| Compound Number | Structure | ¹H NMR—CDCl₃ unless stated |
|---|---|---|
| T25 | 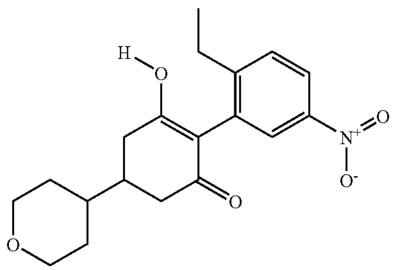 [SMILES: CCc1ccc([N+](=O)[O-])cc1C1=C(O)CC(C2CCOCC2)CC1=O] | δ 8.13 (dd, 1H), 7.88 (dd, 1H), 7.44 (dd, 1H), 6.89 (br d, 1H), 4.02 (dd, 2H), 3.39 (dt, 2H), 2.64 (dt, 2H), 2.48 (dq, 2H), 2.32 (m, 2H), 2.05 (m, 1H), 1.66 (d, 2H), 1.56 (m, 1H), 1.40 (m, 2H), 1.12 (q, 3H) |
| T26 | 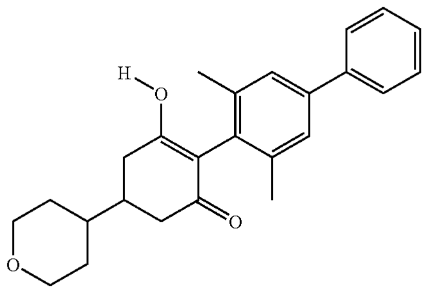 [SMILES: Cc1cc(-c2ccccc2)cc(C)c1C1=C(O)CC(C2CCOCC2)CC1=O] | δ 7.58 (d, 2H), 7.43 (dd, 2H), 7.34 (d, 1H), 7.33 (s, 2H), 5.92 (br s, 1H), 4.03 (m, 2H), 3.39 (m, 2H), 2.69 (m, 2H), 2.44 (dd, 1H); 2.26 (dd, 1H), 2.17 (s, 3H), 2.13 (s, 3H), 2.09 (m, 1H), 1.70 (m, 2H), 1.56 (m, 1H), 1.43 (m, 2H) |

The compounds of the following Tables 1 to 35 can be obtained in an analogous manner.

The spelling C.C used in the following tables indicates the presence of a triple bond between these 2 carbon atoms. For example, C.CH denotes an acetylene group.

TABLE 1

This table covers 290 compounds of the following type:

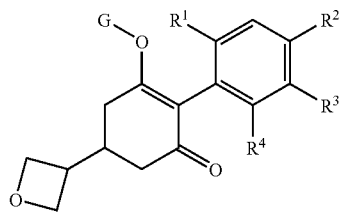

| Compound Number | R¹ | R² | R³ | R⁴ |
|---|---|---|---|---|
| 1.001 | CH₃ | H | H | H |
| 1.002 | CH₃ | CH₃ | H | H |
| 1.003 | CH₃ | H | CH₃ | H |
| 1.004 | CH₃ | H | H | CH₃ |
| 1.005 | CH₃ | CH₃ | CH₃ | H |
| 1.006 | CH₃ | CH₃ | H | CH₃ |
| 1.007 | CH₃ | CH₃ | CH₃ | CH₃ |
| 1.007 | CH₃ | Cl | H | H |
| 1.008 | CH₃ | Cl | H | CH₃ |
| 1.009 | CH₃ | Cl | H | OCH₃ |
| 1.010 | CH₃ | H | Cl | H |
| 1.011 | CH₃ | H | H | Cl |
| 1.012 | CH₃ | CH₃ | Cl | H |
| 1.013 | CH₃ | CH₃ | H | Cl |
| 1.014 | CH₃ | H | Cl | CH₃ |
| 1.015 | CH₃ | CH₃ | Cl | CH₃ |
| 1.016 | CH₃ | Br | H | H |
| 1.017 | CH₃ | Br | H | CH₃ |
| 1.018 | CH₃ | Br | H | OCH₃ |
| 1.019 | CH₃ | H | Br | H |
| 1.020 | CH₃ | H | H | Br |

TABLE 1-continued

This table covers 290 compounds of the following type:

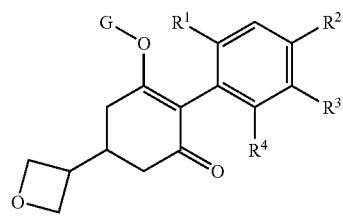

| Compound Number | R¹ | R² | R³ | R⁴ |
|---|---|---|---|---|
| 1.021 | CH₃ | CH₃ | Br | H |
| 1.022 | CH₃ | CH₃ | H | Br |
| 1.023 | CH₃ | H | Br | CH₃ |
| 1.024 | CH₃ | CH₃ | Br | CH₃ |
| 1.025 | CH₃ | CH₃O | H | H |
| 1.026 | CH₃ | CH₃O | H | CH₃ |
| 1.027 | CH₃ | CH₃O | H | Cl |
| 1.028 | CH₃ | CH₃O | H | Br |
| 1.029 | CH₃ | CH₃CH₂O | H | H |
| 1.030 | CH₃ | CH₃CH₂O | H | CH₃ |
| 1.031 | CH₃ | CH₃CH₂O | H | Cl |
| 1.032 | CH₃ | CH₃CH₂O | H | Br |
| 1.033 | CH₃ | H | CH₃O | H |
| 1.034 | CH₃ | H | H | CH₃O |
| 1.035 | CH₃ | CH₃ | CH₃O | H |
| 1.036 | CH₃ | CH₃ | H | CH₃O |
| 1.037 | CH₃ | H | CH₃O | CH₃ |
| 1.038 | CH₃ | CH₃ | CH₃O | CH₃ |
| 1.039 | CH₃ | —CH=CH₂ | H | CH₃ |
| 1.040 | CH₃ | CH₃ | H | —CH=CH₂ |
| 1.041 | CH₃ | —C•CH | H | CH₃ |
| 1.042 | CH₃ | CH₃ | H | —C•CH |
| 1.043 | CH₃ | —CH=CH₂ | H | —CH=CH₂ |
| 1.044 | CH₃ | CH₂CH₃ | H | CH₃ |
| 1.045 | CH₃ | phenyl | H | CH₃ |
| 1.046 | CH₃ | 2-fluorophenyl | H | CH₃ |
| 1.047 | CH₃ | 2-chlorophenyl | H | CH₃ |
| 1.048 | CH₃ | 2-trifluoromethylphenyl | H | CH₃ |
| 1.049 | CH₃ | 2-nitrophenyl | H | CH₃ |
| 1.050 | CH₃ | 2-methylphenyl | H | CH₃ |
| 1051 | CH₃ | 2-methanesulfonylphenyl | H | CH₃ |
| 1.052 | CH₃ | 2-cyanophenyl | H | CH₃ |
| 1.053 | CH₃ | 3-fluorophenyl | H | CH₃ |
| 1.054 | CH₃ | 3-chlorophenyl | H | CH₃ |
| 1.055 | CH₃ | 3-trifluoromethylphenyl | H | CH₃ |
| 1.056 | CH₃ | 3-nitrophenyl | H | CH₃ |
| 1.057 | CH₃ | 3-methylphenyl | H | CH₃ |
| 1.058 | CH₃ | 3-methanesulfonylphenyl | H | CH₃ |
| 1.059 | CH₃ | 3-cyanophenyl | H | CH₃ |
| 1.060 | CH₃ | 4-fluorophenyl | H | CH₃ |
| 1.061 | CH₃ | 4-chlorophenyl | H | CH₃ |
| 1.062 | CH₃ | 4-trifluoromethylphenyl | H | CH₃ |
| 1.063 | CH₃ | 4-nitrophenyl | H | CH₃ |
| 1.064 | CH₃ | 4-methylphenyl | H | CH₃ |
| 1.065 | CH₃ | 4-methanesulfonylphenyl | H | CH₃ |
| 1.066 | CH₃ | 4-cyanophenyl | H | CH₃ |
| 1.067 | CH₃ | H | phenyl | H |
| 1.068 | CH₃ | H | 2-fluorophenyl | H |
| 1.069 | CH₃ | H | 2-chlorophenyl | H |
| 1.070 | CH₃ | H | 2-trifluoromethylphenyl | H |
| 1.071 | CH₃ | H | 2-nitrophenyl | H |
| 1.072 | CH₃ | H | 2-methylphenyl | H |
| 1.073 | CH₃ | H | 2-methylsulfonylphenyl | H |
| 1.074 | CH₃ | H | 2-cyanophenyl | H |
| 1.075 | CH₃ | H | 3-fluorophenyl | H |
| 1.076 | CH₃ | H | 3-chlorophenyl | H |
| 1.077 | CH₃ | H | 3-trifluoromethylphenyl | H |
| 1.078 | CH₃ | H | 3-nitrophenyl | H |
| 1.080 | CH₃ | H | 3-methylphenyl | H |
| 1.081 | CH₃ | H | 3-methylsulfonylphenyl | H |
| 1.082 | CH₃ | H | 3-cyanophenyl | H |
| 1.083 | CH₃ | H | 4-fluorophenyl | H |
| 1.084 | CH₃ | H | 4-chlorophenyl | H |
| 1.085 | CH₃ | H | 4-trifluoromethylphenyl | H |

TABLE 1-continued

This table covers 290 compounds of the following type:

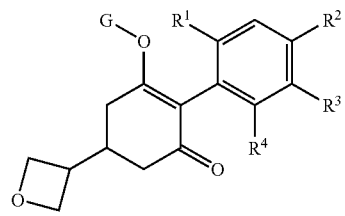

| Compound Number | $R^1$ | $R^2$ | $R^3$ | $R^4$ |
|---|---|---|---|---|
| 1.086 | CH$_3$ | H | 4-nitrophenyl | H |
| 1.087 | CH$_3$ | H | 4-methylphenyl | H |
| 1.088 | CH$_3$ | H | 4-methylsulfonylphenyl | H |
| 1.089 | CH$_3$ | H | 4-cyanophenyl | H |
| 1.090 | CH$_3$ | H | 4-difluoromethyl | H |
| 1.091 | CH$_3$ | H | 2-fluoro-4-chlorophenyl | H |
| 1.092 | CH$_3$ | H | 2,4-dichlorophenyl | H |
| 1.093 | CH$_3$ | H | 2-methyl-4-chlorophenyl | H |
| 1.094 | CH$_3$ | H | 2-methoxy-4-chlorophenyl | H |
| 1.095 | CH$_3$ | H | 2-cyano-4-chlorophenyl | H |
| 1.096 | CH$_3$ | H | 3-fluoro-4-chlorophenyl | H |
| 1.097 | CH$_3$ | H | 2-chloropyridin-5-yl | H |
| 1.098 | CH$_3$ | H | 2,6-dichloropyridin-3-yl | H |
| 1.099 | CH$_2$CH$_3$ | H | H | H |
| 1.100 | CH$_2$CH$_3$ | CH$_3$ | H | H |
| 1.101 | CH$_2$CH$_3$ | H | CH$_3$ | H |
| 1.102 | CH$_2$CH$_3$ | H | H | CH$_3$ |
| 1.103 | CH$_2$CH$_3$ | CH$_3$ | CH$_3$ | H |
| 1.104 | CH$_2$CH$_3$ | CH$_3$ | H | CH$_3$ |
| 1.105 | CH$_2$CH$_3$ | CH$_3$ | CH$_3$ | CH$_3$ |
| 1.106 | CH$_2$CH$_3$ | Cl | H | H |
| 1.107 | CH$_2$CH$_3$ | Cl | H | CH$_3$ |
| 1.108 | CH$_2$CH$_3$ | Cl | H | OCH$_3$ |
| 1.109 | CH$_2$CH$_3$ | H | Cl | H |
| 1.110 | CH$_2$CH$_3$ | H | H | Cl |
| 1.111 | CH$_2$CH$_3$ | CH$_3$ | Cl | H |
| 1.112 | CH$_2$CH$_3$ | CH$_3$ | H | Cl |
| 1.113 | CH$_2$CH$_3$ | H | Cl | CH$_3$ |
| 1.114 | CH$_2$CH$_3$ | CH$_3$ | Cl | CH$_3$ |
| 1.115 | CH$_2$CH$_3$ | Br | H | H |
| 1.116 | CH$_2$CH$_3$ | Br | H | CH$_3$ |
| 1.117 | CH$_2$CH$_3$ | Br | H | OCH$_3$ |
| 1.118 | CH$_2$CH$_3$ | H | Br | H |
| 1.119 | CH$_2$CH$_3$ | H | H | Br |
| 1.120 | CH$_2$CH$_3$ | CH$_3$ | Br | H |
| 1.121 | CH$_2$CH$_3$ | CH$_3$ | H | Br |
| 1.122 | CH$_2$CH$_3$ | H | Br | CH$_3$ |
| 1.123 | CH$_2$CH$_3$ | CH$_3$ | Br | CH$_3$ |
| 1.124 | CH$_2$CH$_3$ | CH$_3$O | H | H |
| 1.125 | CH$_2$CH$_3$ | CH$_3$O | H | CH$_3$ |
| 1.126 | CH$_2$CH$_3$ | CH$_3$O | H | Cl |
| 1.127 | CH$_2$CH$_3$ | CH$_3$O | H | Br |
| 1.128 | CH$_2$CH$_3$ | CH$_3$CH$_2$O | H | H |
| 1.129 | CH$_2$CH$_3$ | CH$_3$CH$_2$O | H | CH$_3$ |
| 1.130 | CH$_2$CH$_3$ | CH$_3$CH$_2$O | H | Cl |
| 1.131 | CH$_2$CH$_3$ | CH$_3$CH$_2$O | H | Br |
| 1.132 | CH$_2$CH$_3$ | H | CH$_3$O | H |
| 1.133 | CH$_2$CH$_3$ | H | H | CH$_3$O |
| 1.134 | CH$_2$CH$_3$ | CH$_3$ | CH$_3$O | H |
| 1.135 | CH$_2$CH$_3$ | CH$_3$ | H | CH$_3$O |
| 1.136 | CH$_2$CH$_3$ | H | CH$_3$O | CH$_3$ |
| 1.137 | CH$_2$CH$_3$ | CH$_3$ | CH$_3$O | CH$_3$ |
| 1.138 | CH$_2$CH$_3$ | —CH=CH$_2$ | H | CH$_3$ |
| 1.139 | CH$_2$CH$_3$ | CH$_3$ | H | —CH=CH$_2$ |
| 1.140 | CH$_2$CH$_3$ | —C•CH | H | CH$_3$ |
| 1.141 | CH$_2$CH$_3$ | CH$_3$ | H | —C•CH |
| 1.142 | CH$_2$CH$_3$ | —CH=CH$_2$ | H | —CH=CH$_2$ |
| 1.143 | CH$_2$CH$_3$ | CH$_2$CH$_3$ | H | CH$_3$ |
| 1.144 | CH$_2$CH$_3$ | phenyl | H | CH$_3$ |
| 1.145 | CH$_2$CH$_3$ | 2-fluorophenyl | H | CH$_3$ |
| 1.146 | CH$_2$CH$_3$ | 2-chlorophenyl | H | CH$_3$ |
| 1.147 | CH$_2$CH$_3$ | 2-trifluoromethylphenyl | H | CH$_3$ |
| 1.148 | CH$_2$CH$_3$ | 2-nitrophenyl | H | CH$_3$ |
| 1.149 | CH$_2$CH$_3$ | 2-methylphenyl | H | CH$_3$ |

TABLE 1-continued

This table covers 290 compounds of the following type:

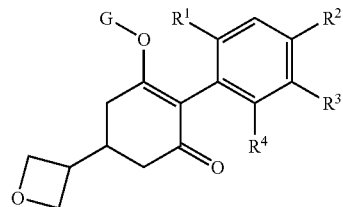

| Compound Number | $R^1$ | $R^2$ | $R^3$ | $R^4$ |
|---|---|---|---|---|
| 1.150 | $CH_2CH_3$ | 2-methylsulfonylphenyl | H | $CH_3$ |
| 1.151 | $CH_2CH_3$ | 2-cyanophenyl | H | $CH_3$ |
| 1.152 | $CH_2CH_3$ | 3-fluorophenyl | H | $CH_3$ |
| 1.153 | $CH_2CH_3$ | 3-chlorophenyl | H | $CH_3$ |
| 1.154 | $CH_2CH_3$ | 3-trifluoromethylphenyl | H | $CH_3$ |
| 1.155 | $CH_2CH_3$ | 3-nitrophenyl | H | $CH_3$ |
| 1.156 | $CH_2CH_3$ | 3-methylphenyl | H | $CH_3$ |
| 1.157 | $CH_2CH_3$ | 3-methylsulfonylphenyl | H | $CH_3$ |
| 1.158 | $CH_2CH_3$ | 3-cyanophenyl | H | $CH_3$ |
| 1.159 | $CH_2CH_3$ | 4-fluorophenyl | H | $CH_3$ |
| 1.160 | $CH_2CH_3$ | 4-chlorophenyl | H | $CH_3$ |
| 1.161 | $CH_2CH_3$ | 4-trifluoromethylphenyl | H | $CH_3$ |
| 1.162 | $CH_2CH_3$ | 4-nitrophenyl | H | $CH_3$ |
| 1.163 | $CH_2CH_3$ | 4-methylphenyl | H | $CH_3$ |
| 1.164 | $CH_2CH_3$ | 4-methylsuifonylphenyl | H | $CH_3$ |
| 1.165 | $CH_2CH_3$ | 4-cyanophenyl | H | $CH_3$ |
| 1.166 | $CH_2CH_3$ | H | phenyl | H |
| 1.167 | $CH_2CH_3$ | H | 2-fluorophenyl | H |
| 1.168 | $CH_2CH_3$ | H | 2-chlorophenyl | H |
| 1.169 | $CH_2CH_3$ | H | 2-trifluoromethylphenyl | H |
| 1.170 | $CH_2CH_3$ | H | 2-nitrophenyl | H |
| 1.1.71 | $CH_2CH_3$ | H | 2-methylphenyl | H |
| 1.172 | $CH_2CH_3$ | H | 2-methylsuifonylphenyl | H |
| 1.173 | $CH_2CH_3$ | H | 2-cyanophenyl | H |
| 1.174 | $CH_2CH_3$ | H | 3-fluorophenyl | H |
| 1.175 | $CH_2CH_3$ | H | 3-chlorophenyl | H |
| 1.176 | $CH_2CH_3$ | H | 3-trifluoromethylphenyl | H |
| 1.177 | $CH_2CH_3$ | H | 3-nitrophenyl | H |
| 1.178 | $CH_2CH_3$ | H | 3-methylphenyl | H |
| 1.179 | $CH_2CH_3$ | H | 3-methylsulfonylphenyl | H |
| 1.180 | $CH_2CH_3$ | H | 3-cyanophenyl | H |
| 1.181 | $CH_2CH_3$ | H | 4-fluorophenyl | H |
| 1.182 | $CH_2CH_3$ | H | 4-chlorophenyl | H |
| 1.183 | $CH_2CH_3$ | H | 4-trifluoromethylphenyl | H |
| 1.184 | $CH_2CH_3$ | H | 4-nitrophenyl | H |
| 1.185 | $CH_2CH_3$ | H | 4-methylphenyl | H |
| 1.186 | $CH_2CH_3$ | H | 4-methylsulfonylphenyl | H |
| 1.187 | $CH_2CH_3$ | H | 4-cyanophenyl | H |
| 1.188 | $CH_2CH_3$ | H | 4-difluoromethyl | H |
| 1.189 | $CH_2CH_3$ | H | 2-fluoro-4-chlorophenyl | H |
| 1.190 | $CH_2CH_3$ | H | 2,4-dichlorophenyl | H |
| 1.191 | $CH_2CH_3$ | H | 2-methyl-4-chlorophenyl | H |
| 1.192 | $CH_2CH_3$ | H | 2-methoxy-4-chlorophenyl | H |
| 1.193 | $CH_2CH_3$ | H | 2-cyano-4-chlorophenyl | H |
| 1.194 | $CH_2CH_3$ | H | 3-fluoro-4-chlorophenyl | H |
| 1.195 | $CH_2CH_3$ | H | 2-chloropyridin-5-yl | H |
| 1.196 | $CH_2CH_3$ | H | 2,6-dichloropyridin-3-yl | H |
| 1.197 | $CH_2CH_3$ | $CH_3$ | H | $CH_2CH_3$ |
| 1.198 | $CH_2CH_3$ | $CH_2CH_3$ | H | $CH_2CH_3$ |
| 1.199 | $CH_2CH_3$ | Cl | H | $CH_2CH_3$ |
| 1.200 | $CH_2CH_3$ | Br | H | $CH_2CH_3$ |
| 1.201 | $CH_2CH_3$ | $NO_2$ | H | $CH_2CH_3$ |
| 1.202 | $CH_2CH_3$ | $CH_3O$ | H | $CH_2CH_3$ |
| 1.203 | $CH_2CH_3$ | $CH_3S$ | H | $CH_2CH_3$ |
| 1.204 | $CH_2CH_3$ | $CH_3SO_2$ | H | $CH_2CH_3$ |
| 1.205 | $CH_2CH_3$ | $CH_2$=CH | H | $CH_2CH_3$ |
| 1.206 | $CH_2CH_3$ | —C•CH | H | $CH_2CH_3$ |
| 1.207 | $CH_2CH_3$ | phenyl | H | $CH_2CH_3$ |
| 1.208 | $CH_2CH_3$ | 2-fluorophenyl | H | $CH_2CH_3$ |
| 1.209 | $CH_2CH_3$ | 2-chlorophenyl | H | $CH_2CH_3$ |
| 1.210 | $CH_2CH_3$ | 2-trifluoromethylphenyl | H | $CH_2CH_3$ |
| 1.211 | $CH_2CH_3$ | 2-nitrophenyl | H | $CH_2CH_3$ |
| 1.212 | $CH_2CH_3$ | 2-methylphenyl | H | $CH_2CH_3$ |
| 1.213 | $CH_2CH_3$ | 2-methylsuifonylphenyl | H | $CH_2CH_3$ |

TABLE 1-continued

This table covers 290 compounds of the following type:

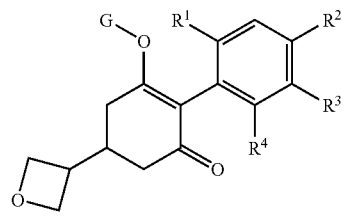

| Compound Number | R¹ | R² | R³ | R⁴ |
|---|---|---|---|---|
| 1.214 | CH₂CH₃ | 2-cyanophenyl | H | CH₂CH₃ |
| 1.215 | CH₂CH₃ | 3-fluorophenyl | H | CH₂CH₃ |
| 1.216 | CH₂CH₃ | 3-chlorophenyl | H | CH₂CH₃ |
| 1.217 | CH₂CH₃ | 3-trifluoromethylphenyl | H | CH₂CH₃ |
| 1.218 | CH₂CH₃ | 3-nitrophenyl | H | CH₂CH₃ |
| 1.219 | CH₂CH₃ | 3-methylphenyl | H | CH₂CH₃ |
| 1.220 | CH₂CH₃ | 3-methylsulfonylphenyl | H | CH₂CH₃ |
| 1.221 | CH₂CH₃ | 3-cyanophenyl | H | CH₂CH₃ |
| 1.222 | CH₂CH₃ | 4-fluorophenyl | H | CH₂CH₃ |
| 1.223 | CH₂CH₃ | 4-chlorophenyl | H | CH₂CH₃ |
| 1.224 | CH₂CH₃ | 4-trifluoromethylphenyl | H | CH₂CH₃ |
| 1.225 | CH₂CH₃ | 4-nitrophenyl | H | CH₂CH₃ |
| 1.226 | CH₂CH₃ | 4-methylphenyl | H | CH₂CH₃ |
| 1.227 | CH₂CH₃ | 4-methylsulfonylphenyl | H | CH₂CH₃ |
| 1.228 | CH₂CH₃ | 4-cyanophenyl | H | CH₂CH₃ |
| 1.229 | OCH₃ | H | phenyl | H |
| 1.230 | OCH₃ | H | 2-fluorophenyl | H |
| 1.231 | OCH₃ | H | 2-chlorophenyl | H |
| 1.232 | OCH₃ | H | 2-trifluoromethylphenyl | H |
| 1.233 | OCH₃ | H | 2-nitrophenyl | H |
| 1.234 | OCH₃ | H | 2-methylphenyl | H |
| 1.235 | OCH₃ | H | 2-methylsulfonylphenyl | H |
| 1.236 | OCH₃ | H | 2-cyanophenyl | H |
| 1.237 | OCH₃ | H | 3-fluorophenyl | H |
| 1.238 | OCH₃ | H | 3-chlorophenyl | H |
| 1.239 | OCH₃ | H | 3-trifluoromethylphenyl | H |
| 1.240 | OCH₃ | H | 3-nitrophenyl | H |
| 1.241 | OCH₃ | H | 3-methylphenyl | H |
| 1.242 | OCH₃ | H | 3-methylsulfonylphenyl | H |
| 1.243 | OCH₃ | H | 3-cyanophenyl | H |
| 1.244 | OCH₃ | H | 4-fluorophenyl | H |
| 1.245 | OCH₃ | H | 4-chlorophenyl | H |
| 1.246 | OCH₃ | H | 4-trifluoromethylphenyl | H |
| 1.247 | OCH₃ | H | 4-nitrophenyl | H |
| 1.248 | OCH₃ | H | 4-methylphenyl | H |
| 1.249 | OCH₃ | H | 4-methylsulfonylphenyl | H |
| 1.250 | OCH₃ | H | 4-cyanophenyl | H |
| 1.251 | OCH₃ | H | 4-difluoromethyl | H |
| 1.252 | OCH₃ | H | 2-fluoro-4-chlorophenyl | H |
| 1.253 | OCH₃ | H | 2,4-dichlorophenyl | H |
| 1.254 | OCH₃ | H | 2-methyl-4-chlorophenyl | H |
| 1.255 | OCH₃ | H | 2-methoxy-4-chlorophenyl | H |
| 1.256 | OCH₃ | H | 2-cyano-4-chlorophenyl | H |
| 1.257 | OCH₃ | H | 3-fluoro-4-chlorophenyl | H |
| 1.258 | OCH₃ | H | 2-chloropyridin-5-yl | H |
| 1.259 | OCH₃ | H | 2,6-dichloropyridin-3-yl | H |
| 1.260 | Cl | H | phenyl | H |
| 1.261 | Cl | H | 2-fluorophenyl | H |
| 1.262 | Cl | H | 2-chlorophenyl | H |
| 1 263 | Cl | H | 2-trifluoromethylphenyl | H |
| 1 264 | Cl | H | 2-nitrophenyl | H |
| 1 265 | Cl | H | 2-methylphenyl | H |
| 1 266 | Cl | H | 2-methylsulfonylphenyl | H |
| 1 267 | Cl | H | 2-cyanophenyl | H |
| 1.268 | Cl | H | 3-fluorophenyl | H |
| 1.269 | Cl | H | 3-chlorophenyl | H |
| 1.270 | Cl | H | 3-trifluoromethylphenyl | H |
| 1.271 | Cl | H | 3-nitrophenyl | H |
| 1.272 | Cl | H | 3-methylphenyl | H |
| 1.273 | Cl | H | 3-methylsulfonylphenyl | H |
| 1.274 | Cl | H | 3-cyanophenyl | H |
| 1.275 | Cl | H | 4-fluorophenyl | H |
| 1.276 | Cl | H | 4-chlorophenyl | H |
| 1.277 | Cl | H | 4-trifluoromethylphenyl | H |

TABLE 1-continued

This table covers 290 compounds of the following type:

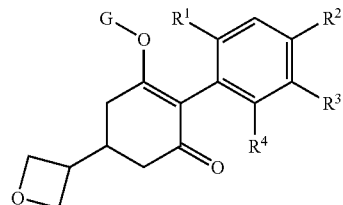

| Compound Number | R¹ | R² | R³ | R⁴ |
|---|---|---|---|---|
| 1.278 | Cl | H | 4-nitrophenyl | H |
| 1.279 | Cl | H | 4-methylphenyl | H |
| 1.280 | Cl | H | 4-methylsulfonylphenyl | H |
| 1.281 | Cl | H | 4-cyanophenyl | H |
| 1.282 | Cl | H | 4-difluoromethyl | H |
| 1.283 | Cl | H | 2-fluoro-4-chlorophenyl | H |
| 1.284 | Cl | H | 2,4-dichlorophenyl | H |
| 1.285 | Cl | H | 2-methyl-4-chlorophenyl | H |
| 1.286 | Cl | H | 2-methoxy-4-chlorophenyl | H |
| 1.287 | Cl | H | 2-cyano-4-chlorophenyl | H |
| 1.288 | Cl | H | 3-fluoro-4-chlorophenyl | H |
| 1.289 | Cl | H | 2-chloropyridin-5-yl | H |
| 1.290 | Cl | H | 2,6-dichloropyridin-3-yl | H |

Wherein G is hydrogen and R¹, R², R³ and R⁴ are defined in Table 1

TABLE 2

This table covers 290 compounds of the following type:

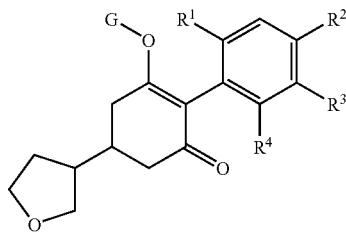

Wherein G is hydrogen and R¹, R², R³ and R⁴ are defined in Table 1

TABLE 3

This table covers 290 compounds of the following type:

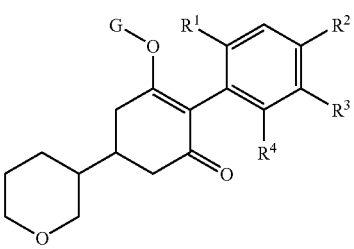

Wherein G is hydrogen and R¹, R², R³ and R⁴ are defined in Table 1

TABLE 4

This table covers 290 compounds of the following type:

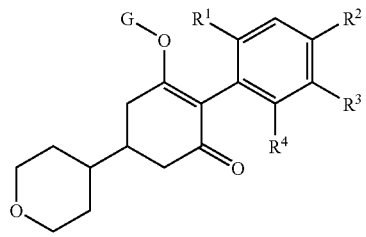

Wherein G is hydrogen and R¹, R², R³ and R⁴ are defined in Table 1

TABLE 5

This table covers 290 compounds of the following type:

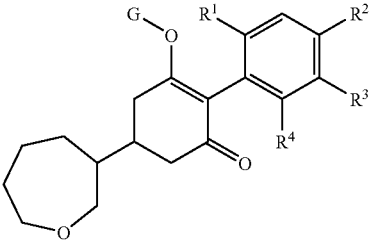

Wherein G is hydrogen and R¹, R², R³ and R⁴ are defined in Table 1

TABLE 6

This table covers 290 compounds of the following type:

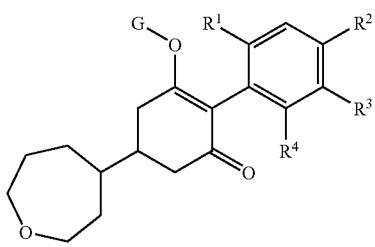

Wherein G is hydrogen and $R^1$, $R^2$, $R^3$ and $R^4$ are defined in Table 1

TABLE 7

This table covers 290 compounds of the following type:

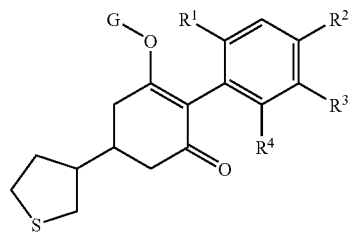

Wherein G is hydrogen and $R^1$, $R^2$, $R^3$ and $R^4$ are defined in Table 1

TABLE 8

This table covers 290 compounds of the following type:

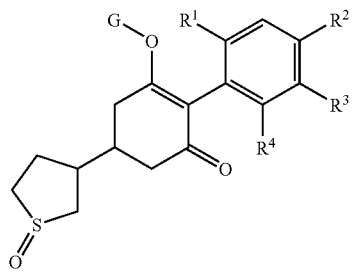

Wherein G is hydrogen and $R^1$, $R^2$, $R^3$ and $R^4$ are defined in Table 1

TABLE 9

This table covers 290 compounds of the following type:

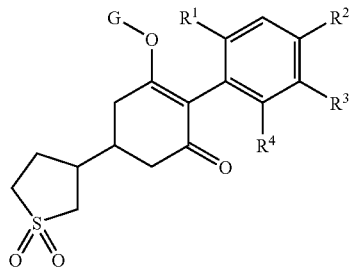

Wherein G is hydrogen and $R^1$, $R^2$, $R^3$ and $R^4$ are defined in Table 1

TABLE 10

This table covers 290 compounds of the following type:

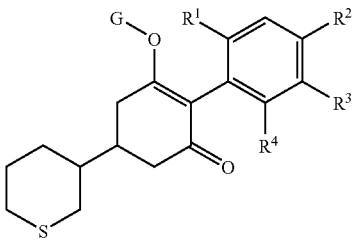

Wherein G is hydrogen and $R^1$, $R^2$, $R^3$ and $R^4$ are defined in Table 1

TABLE 11

This table covers 290 compounds of the following type:

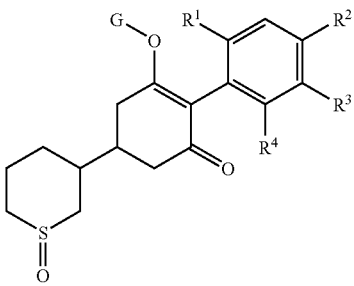

Wherein G is hydrogen and $R^1$, $R^2$, $R^3$ and $R^4$ are defined in Table 1

TABLE 12

This table covers 290 compounds of the following type:

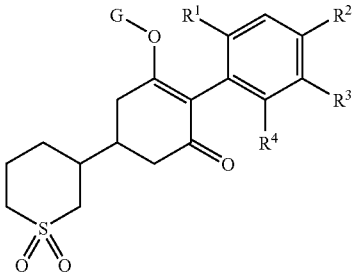

Wherein G is hydrogen and $R^1$, $R^2$, $R^3$ and $R^4$ are defined in Table 1

TABLE 13

This table covers 290 compounds of the following type:

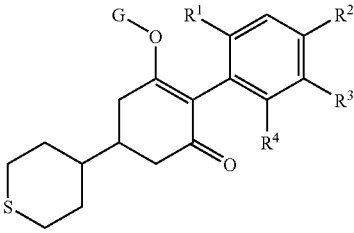

Wherein G is hydrogen and $R^1$, $R^2$, $R^3$ and $R^4$ are defined in Table 1

TABLE 14

This table covers 290 compounds of the following type:

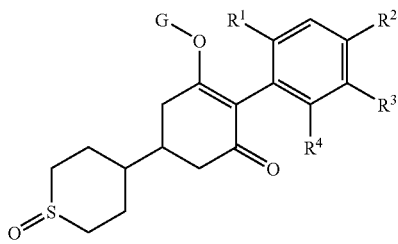

Wherein G is hydrogen and R¹, R², R³ and R⁴ are defined in Table 1

TABLE 15

This table covers 290 compounds of the following type:

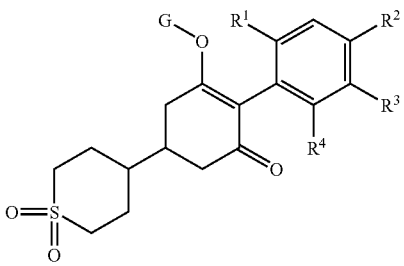

Wherein G is hydrogen and R¹, R², R³ and R⁴ are defined in Table 1

TABLE 16

This table covers 290 compounds of the following type:

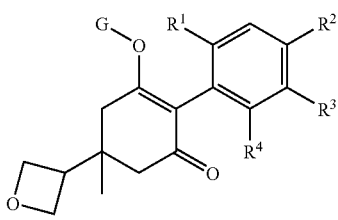

Wherein G is hydrogen and R¹, R², R³ and R⁴ are defined in Table 1

TABLE 17

This table covers 290 compounds of the following type:

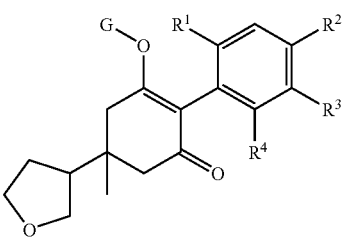

Wherein G is hydrogen and R¹, R², R³ and R⁴ are defined in Table 1

TABLE 18

This table covers 290 compounds of the following type:

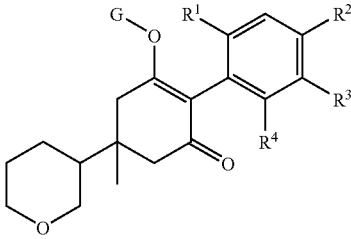

Wherein G is hydrogen and R¹, R², R³ and R⁴ are defined in Table 1

TABLE 19

This table covers 290 compounds of the following type:

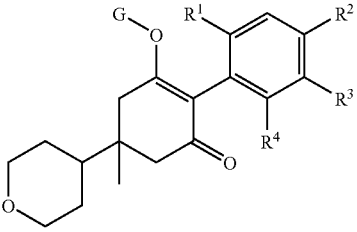

Wherein G is hydrogen and R¹, R², R³ and R⁴ are defined in Table 1

TABLE 20

This table covers 290 compounds of the following type:

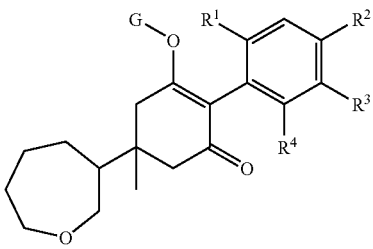

Wherein G is hydrogen and R¹, R², R³ and R⁴ are defined in Table 1

TABLE 21

This table covers 290 compounds of the following type:

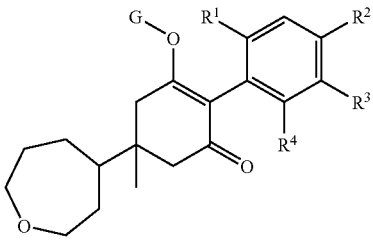

Wherein G is hydrogen and R¹, R², R³ and R⁴ are defined in Table 1

TABLE 22

This table covers 290 compounds of the following type:

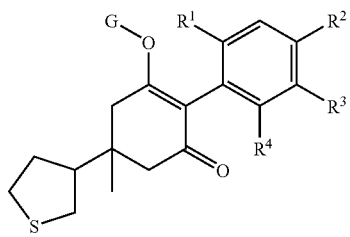

Wherein G is hydrogen and R¹, R², R³ and R⁴ are defined in Table 1

TABLE 23

This table covers 290 compounds of the following type:

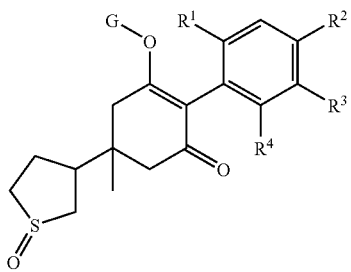

Wherein G is hydrogen and R¹, R², R³ and R⁴ are defined in Table 1

TABLE 24

This table covers 290 compounds of the following type:

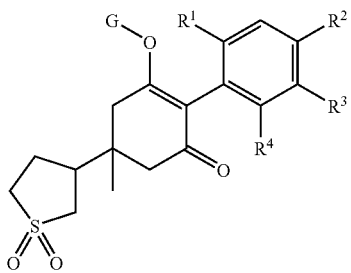

Wherein G is hydrogen and R¹, R², R³ and R⁴ are defined in Table 1

TABLE 25

This table covers 290 compounds of the following type:

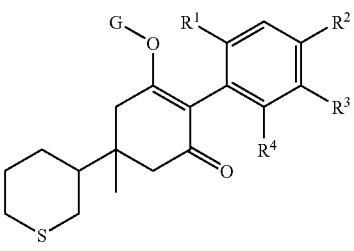

Wherein G is hydrogen and R¹, R², R³ and R⁴ are defined in Table 1

TABLE 26

This table covers 290 compounds of the following type:

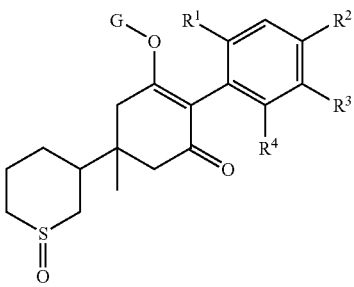

Wherein G is hydrogen and R¹, R², R³ and R⁴ are defined in Table 1

TABLE 27

This table covers 290 compounds of the following type:

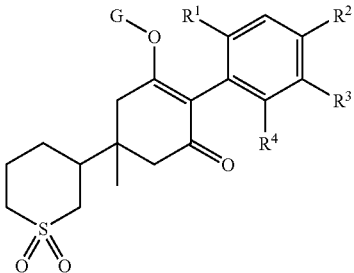

Wherein G is hydrogen and R¹, R², R³ and R⁴ are defined in Table 1

TABLE 28

This table covers 290 compounds of the following type:

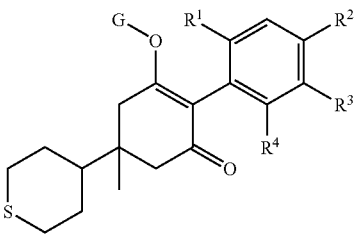

Wherein G is hydrogen and R¹, R², R³ and R⁴ are defined in Table 1

TABLE 29

This table covers 290 compounds of the following type:

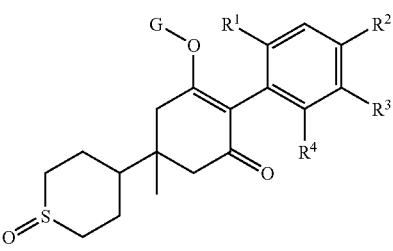

Wherein G is hydrogen and R¹, R², R³ and R⁴ are defined in Table 1

TABLE 30

This table covers 290 compounds of the following type:

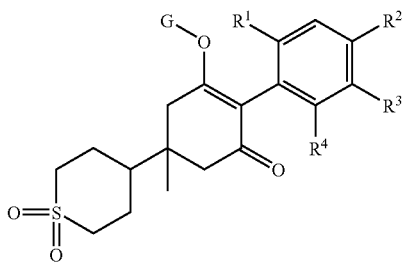

Wherein G is hydrogen and R¹, R², R³ and R⁴ are defined in Table 1

TABLE 31

This table covers 290 compounds of the following type:

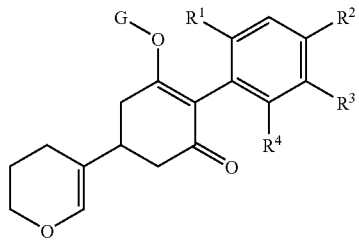

Wherein G is hydrogen and R¹, R², R³ and R⁴ are defined in Table 1

TABLE 32

This table covers 290 compounds of the following type:

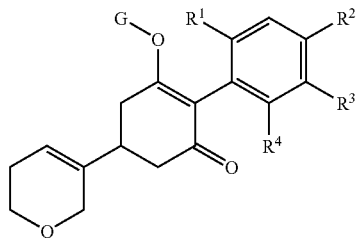

Wherein G is hydrogen and R¹, R², R³ and R⁴ are defined in Table 1

TABLE 33

This table covers 290 compounds of the following type:

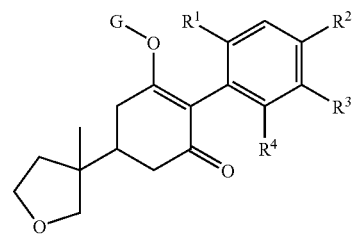

Wherein G is hydrogen and R¹, R², R³ and R⁴ are defined in Table 1

TABLE 34

This table covers 290 compounds of the following type:

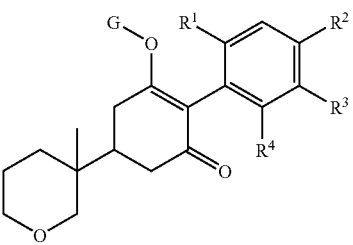

Wherein G is hydrogen and R¹, R², R³ and R⁴ are defined in Table 1

TABLE 35

This table covers 290 compounds of the following type:

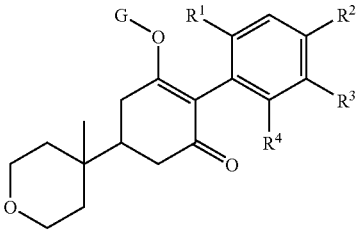

Wherein G is hydrogen and R¹, R², R³ and R⁴ are defined in Table 1.

Example 4

Preparation of 3-oxo-5-(tetrahydrofuran-3-yl)-2-(2,4,6-trimethylphenyl)cyclohex-1-enyl acetate Compound P1 in Table T2

A solution of triethylamine (0.11 ml, 0.79 mmol) in dichloromethane (2 ml) is added dropwise to a chilled (ice-bath) solution of 2-(2,4,6-trimethylphenyl)-5-(tetrahydrofuran-3-yl)cyclohexane-1,3-dione (prepared by a method analogous to that described in Example 2) and acetyl chloride (0.056 ml, 0.79 mmol) in dichloromethane (4.5 ml). Once the addition is complete the cooling bath is removed and the reaction mixture is stirred at room temperature overnight. The reaction mixture is diluted with dichloromethane (35 ml) and washed with saturated aqueous sodium bicarbonate solution (20 ml). The organic phase is dried over anhydrous magnesium sulphate, filtered and the filtrate is evaporated in vacuo. The residue is purified by column chromatography on silica gel, eluting with a mixture of ethyl acetate and hexane to give 3-oxo-5-(tetrahydrofuran-3-yl)-2-(2,4,6-trimethylphenyl)cyclohex-1-enyl acetate.

$^1$H NMR data (CDCl$_3$, ppm): $\delta_H$ 6.83 (s, 2H), 4.00-3.89 (m, 2H), 3.79 (m, 1H), 3.49 (m, 1H), 2.78-2.54 (m, 3H), 1.65 (m, 1H), 2.40 (m, 1H), 2.32-2.21 (m, 2H), 2.24 (s, 3H), 2.10 (m, 1H), 2.02 (s, 3H), 1.98 (s, 3H), 1.86 (d, 3H).

Compounds in Table T2 below are prepared by similar methods using appropriate starting materials.

TABLE T2

| Compound Number | Structure | ¹H NMR - CDCl₃ unless stated |
|---|---|---|
| P1 | 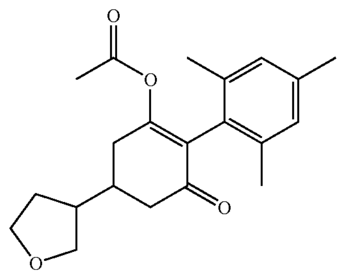 [SMILES: CC(=O)OC1=C(c2c(C)cc(C)cc2C)C(=O)CC(C2CCOC2)C1] | δ 6.83 (s, 2H), 4.00-3.89 (m, 2H), 3.79 (m, 1H), 3.49 (m, 1H), 2.78-2.54 (m, 3H), 1.65 (m, 1H), 2.40 (m, 1H), 2.32-2.21 (m, 2H), 2.24 (s, 3H), 2.10 (m, 1H), 2.02 (s, 3H), 1.98 (s, 3H), 1.86 (d, 3H) |
| P2 | 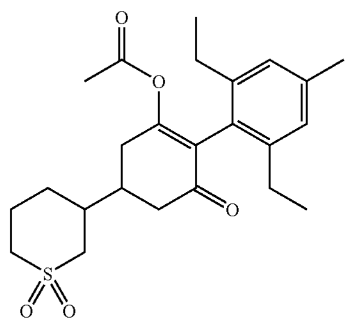 [SMILES: CCc1cc(C)cc(CC)c1C1=C(OC(C)=O)CC(C2CCCS(=O)(=O)C2)CC1=O] | δ 6.90 (s, 2H), 3.14 (m, 2H), 3.03 (m, 2H), 2.77 (m, 1H), 2.66 (m, 2H), 2.44 (m, 2H), 2.34-2.25 (m, 8H), 2.18 (m, 1H), 2.05 (m, 2H), 1.89 (s, 3H), 1.64 (m, 1H), 1.10 (2 × t, 6H) |
| P3 | 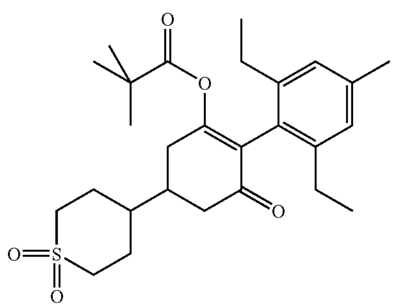 [SMILES: CCc1cc(C)cc(CC)c1C1=C(OC(=O)C(C)(C)C)CC(C2CCS(=O)(=O)CC2)CC1=O] | δ 6.88 (s, 2H), 3.15 (m, 2H), 3.04-2.96 (m, 2H), 2.81-2.61 (m, 3H), 2.49-2.39 (m, 1H), 2.35-2.26 (m, 8H), 2.23 (m, 2H), 2.05 (m, 2H), 1.69 (m, 1H), 1.10 (2 × t, 6H), 0.88 (s, 9H) |

Experimental Procedures to Key Intermediates

Example 1A

Preparation of 2,6-diethyl-4-methylphenylboronic acid

To a solution at −78° C. of 25 g (110 mmol) of 2,6-diethyl-4-methylbromobenzene (preparation described in WO 2000078712) in 240 ml of tetrahydrofuran is added a ~1.6 M solution of butyllithium in hexanes (75 ml, 120 mmol) dropwise over 10 minutes. The mixture is stirred for 10 minutes at −78° C., then trimethylborate (24.6 ml, 22.9 g; 220 mmol) is added at once and stirring is continued at −78° C. for 30 minutes. The cooling bath is removed and the solution is allowed to warm up to room temperature over 1 hour and quenched with 2N aqueous hydrochloric acid (140 ml).

The organic layer is separated, and the aqueous phase is extracted three times with diethyl ether:hexane 1:1. The organic extracts are combined, dried over anhydrous sodium sulfate, filtered and the filtrate concentrated in vacuo. The oily residue is taken up in hexane under stirring, and the white solid is collected by filtration to give 2,6-diethyl-4-methylphenylboronic acid. The filtrate is concentrated and purified by column chromatography on silica gel give a further quantity of desired product. A combined yield of 16.6 g (78%) of 2,6-diethyl-4-methylphenylboronic acid is obtained.

Example 1B

Preparation of 5-(4-chlorophenyl)-2-methylphenylboronic acid

Step 1

4-Chlorophenylboronic acid (20.2 g, 0.13 mol) and tetrakis (triphenylphosphine)palladium (0) (3.7 g, 0.003 mol) are added to a solution of 5-bromo-2-methylaniline (20 g, 0.1 mol) in 1,2-dimethoxyethane (200 ml). After stirring the reaction mixture for 15 minutes at 20° C., a solution of 20% aqueous sodium carbonate (300 ml) is added to the mixture, and the resulting mixture is refluxed for 24 hours. The reaction mixture is cooled to room temperature, diluted with water (600 ml) and extracted using ethyl acetate. The combined organic extracts are dried over anhydrous sodium sulfate, filtered and the filtrate evaporated in vacuo. The residue is further purified by column chromatography on silica gel, eluting with 7% ethyl acetate in hexane to give 5-(4-chlorophenyl)-2-methylaniline (21.0 g).

Step 2

Hydrobromic acid (48% wt. in water, 120 ml) is added dropwise to a suspension of 5-(4-chlorophenyl)-2-methylaniline (21 g, 0.09 mol) in water (80 ml), and the mixture stirred until the solid is dissolved. The mixture is cooled to −5° C. and a solution of sodium nitrite (10.12 g, 0.14 mol) in water (50 ml) is added dropwise, maintaining the temperature at 0-5° C. The reaction mixture is stirred for 1 hour, then added to a pre-cooled solution of cuprous bromide (17.9 g, 0.12 mol) in hydrobromic acid (48% wt. in water, 120 ml) at 0° C. The reaction mixture is stirred and allowed to warm to room temperature overnight. The mixture is extracted with ethyl acetate, and the organic extracts are combined, dried over anhydrous sodium sulfate, filtered and the filtrate concentrated in vacuo. The residue is further purified by column chromatography on silica gel, eluting with 2% ethyl acetate in hexane to give 5-(4-chlorophenyl)-2-methyl-1-bromobenzene (15.0 g).

Step 3

5-(4-chlorophenyl)-2-methyl-1-bromobenzene (5.0 g, 0.02 mol) is dissolved in THF (125 ml), and the temperature is brought to −78° C. n-Butyllithium (1.33 molar solution in hexanes, 17.3 ml,) is added dropwise over 30 minutes, maintaining the temperature at around −78° C. The reaction mixture is stirred for one and half hours at −78° C., then trimethylborate (2.58 g, 0.024 mol) is added dropwise and the reaction mixture stirred for three and half hours, allowing it to warm to 0° C. A solution of 2N aqueous hydrochloric acid (50 ml) is then added dropwise, and once the addition is complete the mixture is stirred for 2 hours. The mixture is concentrated in vacuo to remove most of the tetrahydrofuran, then diluted with water (~80 ml) and extracted with diethyl ether. The organic extracts are combined, dried over anhydrous sodium sulfate, filtered and the filtrate evaporated in vacuo. The residue is further purified by flash column chromatography on silica gel, eluting with 7% ethyl acetate in hexane to give 5-(4-chlorophenyl)-2-methylphenylboronic acid (2.5 g).

Example 1C

Preparation of
5-(4-chlorophenyl)-2-ethylphenylboronic acid

Step 1

Ammonium nitrate (39.6 g, 0.49 mol) is added portionwise to a chilled (ice-bath) solution of 4-ethylaniline (20 g, 0.16 mol) in concentrated sulfuric acid (100 ml, maintaining the temperature 10° to 0° C. by external cooling. The reaction mixture is stirred for two hours, then poured onto crushed ice, and the precipitate is collected by filtration. The solid is taken up in water, the solution made neutral by addition of dilute aqueous sodium hydroxide solution and the extracted with ethyl acetate. The organic extracts are combined, dried over anhydrous sodium sulfate, filtered and the filtrate evaporated in vacuo to give 4-ethyl-3-nitroaniline (20 g).

Step 2

Hydrobromic acid (48% wt. in water, 240 ml) is added dropwise to a suspension of 4-ethyl-3-nitroaniline (20 g, 0.12 mol) in water (80 ml), and the mixture stirred until the solid is dissolved. The mixture is cooled to −5° C. and a solution of sodium nitrite (19.8 g, 0.28 mol) in water (100 ml) is added dropwise, maintaining the temperature at 0-5° C. Once the addition is complete, the cooling bath is removed and the reaction mixture is stirred for one hour at room temperature. The mixture is added dropwise to a pre-cooled solution of cuprous bromide (22.4 g, 0.16 mol) in hydrobromic acid (48% wt. in water) at 0° C. The reaction mixture is stirred and allowed to warm to room temperature over three hours. The mixture is extracted with diethyl ether, and the organic extracts are combined, dried over anhydrous sodium sulfate, filtered and the filtrate concentrated in vacuo. The residue is further purified by column chromatography on silica gel, eluting with hexane to give 4-bromo-1-ethyl-2-nitrobenzene (18 g).

Step 3

A solution of ammonium chloride (12.5 g, 0.2 mol) in water (30 ml) is added to a mixture of zinc dust (35.7 g, 0.5 mol) and 4-bromo-1-ethyl-2-nitrobenzene (18 g, 0.07 mol) in methanol (720 ml) and water (180 ml). The reaction mixture is refluxed for one hour, then cooled to room temperature and filtered through a plug of diatomaceous earth. The filtrate is concentrated in vacuo, then diluted with water and extracted with ethyl acetate. The combined organic extracts are washed with water and brine, dried over anhydrous sodium sulfate, filtered and the filtrate concentrated in vacuo to yield 5-bromo-2-ethylaniline (14 g), used without further purification in the next step.

Step 4

4-Chlorophenylboronic acid (13.2 g, 0.08 mol) and tetrakis (triphenylphosphine) palladium (0) (2.4 g, 0.002 mol) are added to a solution of 5-bromo-2-ethylaniline (14.1 g, 0.07 mol) in 1,2-dimethoxyethane (140 ml). After stirring the reaction mixture for 15 minutes at 20° C., a solution of 20% aqueous sodium carbonate (300 ml) is added to the mixture, and the resulting mixture is refluxed for 24 hours. The reaction mixture is cooled to room temperature, diluted with water and extracted using ethyl acetate. The combined organic extracts are dried over anhydrous sodium sulfate, filtered and the filtrate evaporated in vacuo. The residue is further purified by column chromatography on silica gel, eluting with 5% ethyl acetate in hexane to give 5-(4-chlorophenyl)-2-ethylaniline (14.3 g).

Step 5

Hydrobromic acid (48% wt. in water, 85 ml) is added dropwise to a suspension of 5-(4-chlorophenyl)-2-ethylaniline (14.3 g, 0.062 mol) in water (57 ml), and the mixture stirred. The mixture is cooled to −5° C. and a solution of sodium nitrite (5.07 g, 0.072 mol) in water (25 ml) is added dropwise, maintaining the temperature at 0-5° C. The reaction mixture is stirred for 1 hour, then added to a pre-cooled solution of cuprous bromide (9 g, 0.062 mol) in hydrobromic acid (48% wt. in water, 64 ml) at 0° C. The reaction mixture is stirred and allowed to warm to room temperature overnight. The mixture is diluted with water, extracted with diethyl ether, and the organic extracts are combined, dried over anhydrous sodium sulfate, filtered and the filtrate concentrated in vacuo. The residue is further purified by column chromatography on silica gel, eluting with 2% ethyl acetate in hexane to give 5-(4-chlorophenyl)-2-ethyl-1-bromobenzene (10 g).

Step 6

5-(4-chlorophenyl)-2-ethyl-1-bromobenzene (10 g, 0.03 mol) is dissolved in THF (250 ml), and the temperature is brought to −78° C. n-Butyllithium (1.33 molar solution in hexanes, 34.6 ml,) is added dropwise over 30 minutes, maintaining the temperature at around −78° C. The reaction mixture is stirred for one and half hours, then trimethylborate (4.9 g, 0.05 mol) is added dropwise and the reaction mixture stirred for two hours. A solution of 2N aqueous hydrochloric acid (100 ml) is added dropwise, and once the addition is complete the mixture is stirred for two hours. The mixture is concentrated to remove most of the tetrahydrofuran, then diluted with water and extracted with diethyl ether. The organic extracts are washed with water and brine, combined, dried over anhydrous sodium sulfate, filtered and the filtrate evaporated in vacuo. The residue is further purified by flash column chromatography on silica gel, eluting with 7% ethyl acetate in hexane to give 5-(4-chloro-phenyl)-2-methylphenylboronic acid (5.4 g).

Example 1D

Preparation of 3,5-dimethylbiphenylboronic acid tert-Butyllithium (1.7 M solution in hexanes, 36.2 ml, 62.6 mmol) is added dropwise to a solution of 3,5-dimethylbiphenyl (7.27 g; 28 mmol) in dry tetrahydrofuran (150 ml) at −78° C. and stirred under an atmosphere of nitrogen for 30 minutes. Trimethyl borate (9.54 ml; 84 mmol) is added and the resulting mixture is stirred at −78° C. for 30 min and then allowed to warm to room temperature. The reaction mixture is acidified with aqueous hydrochloric acid and extracted with ether (2×150 ml). The organic layers are combined, dried over anhydrous magnesium sulfate, filtered and the filtrate evaporated in vacuo to give a yellow solid. The crude product is triturated with iso-hexane and filtered to give 3,5-dimethylbiphenylboronic acid (5.89 g) as a white powder.

Example 1E

Preparation of 3,5-dimethylbiphen-4-yllead triacetate

To a solution of lead tetraacetate (4.3 g, 9.7 mmol) in dry chloroform (15 ml) at 40° C. is added 3,5-dimethylbiphen-4-ylboronic acid (2.0 g; 8.8 mmol) in one portion under an atmosphere of nitrogen. The mixture is stirred at 40° C. for 4 hours, and then is cooled to room temperature. The precipitate is removed by filtration, and the filtrate is then passed through a plug of potassium carbonate supported on diatomaceous earth to remove acetic acid. The filtrate is evaporated in vacuo to afford 3,5-dimethylbiphen-4-yllead triacetate (3.37 g) as a brown oil.

Biological Examples

Monocotyledonous and dicotyledonous test plants were sown in standard soil in pots. After cultivation for one day (pre-emergence) or after 10 days cultivation (post-emergence) under controlled conditions in a glasshouse, the plants were sprayed with an aqueous spray solution derived from the formulation of the technical active ingredient in 0.6 ml acetone and 45 ml formulation solution containing 10.6% Emulsogen EL (Registry number 61791-12-6), 42.2% N-methyl pyrrolidone, 42.2% dipropylene glycol monomethyl ether (Registry number 34590-94-8) and 0.2% X-77 (Registry number 11097-66-8). The test plants were then grown in a greenhouse under optimum conditions until, 14 or 15 days later for post-emergence and 19, 20 or 21 days for pre-emergence, the test was evaluated (100=total damage to plant; 0=no damage to plant).

Test Plants:
 Alopecurus myosuroides (ALOMY), Avena fatua (AVEFA), Lolium perenne (LOLPE), Setaria faberi (SETFA), Digitaria sanguinalis (DIGSA), Echinochloa crus-galli (ECHCG)

Pre-Emergence Activity

| Compound Number | Rate g/ha | ALOMY | AVEFA | LOLPE | SETFA | DIGSA | ECHCG |
|---|---|---|---|---|---|---|---|
| T2 | 500 | 100 | 100 | 100 | 100 | 100 | 90 |
| T3 | 500 | 90 | 90 | 100 | 60 | 100 | 100 |
| T4 | 500 | 100 | 70 | 100 | 100 | 90 | 100 |
| T6 | 500 | 90 | 20 | 100 | 100 | 100 | 100 |
| T7 | 500 | 70 | 30 | 100 | 100 | 100 | 100 |
| T8 | 500 | 100 | 60 | 80 | 100 | 100 | 100 |
| T9 | 500 | 60 | 60 | 100 | 100 | 80 | 100 |
| T10 | 500 | 90 | 50 | — | 70 | 80 | 80 |
| T11 | 500 | 80 | 70 | 80 | 100 | 100 | 100 |
| T12 | 500 | 90 | 90 | 100 | 100 | 100 | 100 |
| T13 | 500 | 90 | 80 | 100 | 100 | 100 | 100 |
| T14 | 500 | 60 | 20 | 70 | 90 | 90 | 70 |
| T15 | 500 | 60 | 60 | 80 | 90 | 70 | 20 |
| T16 | 500 | 0 | 100 | 100 | 100 | 100 | 100 |
| T17 | 500 | 20 | 70 | 0 | 50 | 60 | 60 |
| T18 | 500 | 100 | 100 | 100 | 100 | 100 | 100 |
| T19 | 500 | 100 | 90 | 100 | 100 | 100 | 100 |
| T20 | 500 | 100 | 100 | 100 | 100 | 100 | 100 |
| T21 | 500 | 40 | 70 | 40 | 100 | 100 | 100 |
| T22 | 500 | 90 | 90 | 90 | — | — | 70 |
| T23 | 500 | 100 | 100 | 100 | 70 | 100 | 50 |
| P1 | 500 | 60 | 20 | 70 | 0 | 60 | 30 |
| P2 | 500 | 90 | 100 | 80 | 100 | 100 | 100 |
| P3 | 500 | 90 | 80 | 90 | 90 | 100 | 100 |

Post-Emergence Activity

| Compound Number | Rate g/ha | ALOMY | AVEFA | LOLPE | SETFA | DIGSA | ECHCG |
|---|---|---|---|---|---|---|---|
| T2 | 500 | 90 | 100 | 90 | 90 | 100 | 100 |
| T3 | 500 | 100 | 90 | 100 | 90 | 80 | 100 |
| T4 | 500 | 100 | 100 | 100 | 100 | 100 | 80 |

-continued

| Compound Number | Rate g/ha | ALOMY | AVEFA | LOLPE | SETFA | DIGSA | ECHCG |
|---|---|---|---|---|---|---|---|
| T6 | 500 | 100 | 90 | 100 | 100 | 100 | 100 |
| T7 | 500 | 90 | 90 | 80 | 100 | 100 | 100 |
| T8 | 500 | 80 | 70 | 100 | 90 | 90 | 90 |
| T9 | 500 | 80 | 70 | 100 | 80 | 90 | 100 |
| T10 | 500 | 80 | 60 | 80 | 80 | 90 | 90 |
| T11 | 500 | 90 | 90 | 90 | 100 | 100 | 100 |
| T12 | 500 | 90 | 90 | 90 | 100 | 100 | 100 |
| T13 | 500 | 100 | 100 | 100 | 100 | 90 | 90 |
| T14 | 500 | 70 | 30 | 60 | 90 | 90 | 80 |
| T15 | 500 | 60 | 20 | 60 | 90 | 80 | 70 |
| T16 | 500 | 100 | 80 | 90 | 100 | 100 | 90 |
| T17 | 500 | 20 | 20 | 0 | 90 | 90 | 90 |
| T18 | 500 | 90 | 100 | 70 | 100 | 100 | 70 |
| T19 | 500 | 80 | 90 | 80 | 100 | 100 | 100 |
| T20 | 500 | 80 | 70 | 60 | 90 | 100 | 100 |
| T21 | 500 | 80 | 70 | 70 | 90 | 80 | 100 |
| T22 | 500 | 90 | 90 | 80 | 100 | 100 | 80 |
| T23 | 125 | 90 | 90 | 50 | 70 | 80 | 80 |
| P1 | 500 | 80 | 20 | 80 | 70 | 80 | 70 |
| P2 | 125 | 10 | 20 | 0 | 20 | 90 | 20 |
| P3 | 125 | 70 | 30 | 0 | 60 | 70 | 60 |

What is claimed is:

1. A compound of Formula (I)

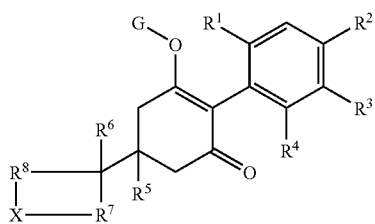

Formula (I)

wherein $R^1$ is methyl, ethyl, n-propyl, iso-propyl, cyclopropyl, halomethyl, haloethyl, halogen, vinyl, ethynyl, methoxy, ethoxy, halomethoxy or haloethoxy, $R^2$ and $R^3$ are, independently hydrogen, halogen, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$haloalkenyl, $C_2$-$C_6$alkynyl, $C_3$-$C_6$alkenyloxy, $C_3$-$C_6$haloalkenyloxy, $C_3$-$C_6$alkynyloxy, $C_3$-$C_6$cycloalkyl, $C_1$-$C_6$alkylthio, $C_1$-$C_6$alkylsulfinyl, $C_1$-$C_6$alkylsulfonyl, $C_1$-$C_6$alkylsulfonyloxy, $C_1$-$C_6$haloalkylsulfonyloxy, cyano, nitro, phenyl, phenyl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, or heteroaryl or heteroaryl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, $R^4$ is hydrogen, methyl, ethyl, n-propyl, iso-propyl, halomethyl, haloethyl, halogen, vinyl, ethynyl, methoxy, ethoxy, halomethoxy or haloethoxy, X is O, S, S(O) or S(O)$_2$, $R^5$ is hydrogen or methyl, $R^6$ is hydrogen, methyl or ethyl, or forms a double bond, which links the carbon atom, to which $R^6$ is attached, with the adjacent carbon atom of $R^7$ or $R^8$, $R^7$ and $R^8$ are independently of each other $C_1$-$C_5$alkylene, which is unsubstituted or substituted by methyl or ethyl, or $C_2$-$C_5$alkenylene, which is unsubstituted or substituted by methyl or ethyl, and G is hydrogen, an alkali metal, alkaline earth metal, sulfonium, ammonium or a latentiating group;

and wherein, when G is the latentiating group, then G is selected from the groups $C_1$-$C_8$ alkyl, $C_2$-$C_8$ haloalkyl, phenyl$C_1$-$C_8$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl$C_1$-$C_8$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_8$ alkenyl, $C_3$-$C_8$ haloalkenyl, $C_3$-$C_8$ alkynyl, $C(X^a)$—$R^a$, $C(X^b)$—$X^c$—$R^b$, $C(X^d)$—N($R^c$)—$R^d$, —SO$_2$—$R^e$, —P($X^e$)($R^f$)—$R^g$ and CH$_2$—$X^f$—$R^h$;

wherein $X^a$, $X^b$, $X^c$, $X^d$, $X^e$ and $X^f$ are independently of each other oxygen or sulfur;

and wherein $R^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$ cyanoalkyl, $C_1$-$C_{10}$nitroalkyl, $C_1$-$C_{10}$ aminoalkyl, $C_1$-$C_5$alkylamino $C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, amino carbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N-$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$ haloalkyl, $C_1$-$C_3$ alkoxy, $C_1$-$C_3$haloalkoxy, $C_1$-$C_3$ alkylthio, $C_1$-$C_3$alkylsulfinyl, $C_1$-$C_3$ alkylsulfonyl, halogen, cyano, or by nitro), $C_2$-$C_5$ haloalkenyl, $C_3$-$C_8$ cycloalkyl; phenyl or phenyl substituted by $C_1$-$C_3$ alkyl, $C_1$-$C_3$haloalkyl, $C_1$-$C_3$alkoxy, $C_1$-$C_3$haloalkoxy, halogen, cyano or nitro; or heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro;

$R^b$ is $C_1$-$C_{18}$ alkyl, $C_3$-$C_{18}$alkenyl, $C_3$-$C_{18}$ alkynyl, $C_2$-$C_{10}$haloalkyl, $C_1$-$C_{10}$ cyanoalkyl, $C_1$-$C_{10}$nitroalkyl, $C_2$-$C_{10}$aminoalkyl, $C_1$-$C_5$ alkylamino$C_1$-$C_5$ alkyl, $C_2$-$C_8$ dialkylamino$C_1$-$C_5$ alkyl, $C_3$-$C_7$ cycloalkyl$C_1$-$C_5$ alkyl, $C_1$-$C_5$ alkoxy$C_1$-$C_5$ alkyl, $C_3$-$C_5$ alkenyloxy$C_1$-$C_5$ alkyl, $C_3$-$C_5$ alkynyloxy$C_1$-$C_5$ alkyl, $C_1$-$C_5$ alkylthio $C_1$-$C_5$ alkyl, $C_1$-$C_5$ alkylsulfinyl$C_1$-$C_5$ alkyl, $C_1$-$C_5$ alkylsulfonyl$C_1$-$C_5$ alkyl, $C_2$-$C_8$ alkylideneaminoxy$C_1$-$C_5$ alkyl, $C_1$-$C_5$ alkyl carbonyl$C_1$-$C_5$ alkyl, $C_1$-$C_5$ alkoxycarbonyl$C_1$-$C_5$ alkyl, aminocarbonyl$C_1$-$C_5$ alkyl, $C_1$-$C_5$ alkylaminocarbonyl$C_1$-$C_5$ alkyl, $C_2$-$C_8$ dialkylaminocarbonyl$C_1$-$C_5$ alkyl, $C_1$-$C_5$ alkylcarbonylamino$C_1$-$C_5$ alkyl, N—$C_1$-$C_5$ alkylcarbonyl-N-$C_1$-$C_5$ alkylamino $C_1$-$C_5$ alkyl, $C_3$-$C_6$trialkylsilyl$C_1$-$C_5$ alkyl, phenyl$C_1$-$C_5$ alkyl (wherein the phenyl is optionally substituted by $C_1$-$C_3$alkyl, $C_1$-$C_3$haloalkyl, $C_1$-$C_3$alkoxy, $C_1$-$C_3$ haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$ haloalkyl, $C_1$-$C_3$alkoxy, $C_1$-$C_3$haloalkoxy, $C_1$-$C_3$alkylthio, $C_1$-$C_3$ alkylsulfinyl, $C_1$-$C_3$alkylsulfonyl, halogen, cyano, or by nitro), $C_3$-$C_5$haloalkenyl, $C_3$-$C_8$cycloalkyl; phenyl or phenyl substituted by $C_1$-$C_3$ alkyl, $C_1$-$C_3$haloalkyl, $C_1$-$C_3$alkoxy, $C_1$-$C_3$haloalkoxy, halogen, cyano or nitro; or heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro; and $R^c$ and $R^d$ are each independently of each other hydrogen, $C_1$-$C_{10}$alkyl, $C_3$-$C_{10}$alkenyl, $C_3$-$C_{10}$ alkynyl, $C_2$-$C_{10}$haloalkyl, $C_1$-$C_{10}$ cyanoalkyl, $C_1$-$C_{10}$nitroalkyl, $C_1$-$C_{10}$ aminoalkyl, $C_1$-$C_5$ alkylamino$C_1$-$C_5$ alkyl, $C_2$-$C_8$ dialkylamino$C_1$-$C_5$ alkyl, $C_3$-$C_7$ cycloalkyl$C_1$-$C_5$ alkyl, $C_1$-$C_5$ alkoxy$C_1$-$C_5$ alkyl, $C_3$-$C_5$alkenyloxy$C_1$-$C_5$ alkyl, $C_3$-$C_5$ alkynyloxy$C_1$-$C_5$alkyl, $C_1$-$C_5$ alkylthio$C_1$-$C_5$ alkyl, $C_1$-$C_5$ alkylsulfinyl$C_1$-$C_5$ alkyl, $C_1$-$C_5$ alkylsulfonyl$C_1$-$C_5$ alkyl, $C_2$-$C_8$ alkylideneaminoxy$C_1$-$C_5$ alkyl, $C_1$-$C_5$ alkylcarbonyl$C_1$-$C_5$ alkyl, $C_1$-$C_5$ alkoxycarbonyl$C_1$-$C_5$ alkyl, aminocarbonyl$C_1$-$C_5$ alkyl, $C_1$-$C_5$ alkylaminocarbonyl$C_1$-$C_5$ alkyl, $C_2$-$C_8$ dialkylaminocarbonyl$C_1$-$C_5$ alkyl, $C_1$-$C_5$ alkylcarbonylamino$C_1$-$C_5$ alkyl, N—$C_1$-$C_5$ alkylcarbonyl-N—$C_2$-$C_5$alkylaminoalkyl, $C_3$-$C_6$trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_1$ alkyl, $C_1$-$C_3$haloalkyl, $C_1$-$C_3$alkoxy, $C_1$-$C_3$haloalkoxy, halogen, cyano or nitro; heteroarylamino or heteroarylamino substituted by $C_1$-$C_1$ alkyl, $C_1$-$C_3$haloalkyl, $C_1$-$C_3$alkoxy, $C_1$-$C_3$haloalkoxy, halogen, cyano or nitro; diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; or $C_3$-$C_7$cycloalkylamino, di-$C_3$-$C_7$cycloalkylamino or $C_3$-$C_7$cycloalkoxy;

or $R^c$ and $R^d$ may join together to form a 3-7 membered ring, optionally containing one heteroatom selected from O or S; and $R^e$ is $C_1$-$C_{10}$ alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$ alkynyloxy$C_1$-$C_5$alkyl, $C_1$-$C_5$alkylthio $C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$ alkyl, $C_1$-$C_5$alkylcarbonyl$C_1$-$C_5$ alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$ alkyl, $C_2$-$C_8$dialkylaminocarbonyl$C_1$-$C_5$ alkyl, $C_1$-$C_5$ alkylcarbonylamino$C_1$-$C_5$alkyl, N—$C_1$-$C_5$ alkylcarbonyl-N—$C_1$-$C_5$ alkylamino $C_1$-$C_5$ alkyl, $C_3$-$C_6$trialkylsilyl$C_1$-$C_5$ alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$ alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_1$ alkyl, $C_1$-$C_3$haloalkyl, $C_1$-$C_3$alkoxy, $C_1$-$C_3$haloalkoxy, halogen, cyano or by nitro; heteroarylamino or heteroarylamino substituted by $C_1$-$C_1$ alkyl, $C_1$-$C_3$haloalkyl, $C_1$-$C_3$alkoxy, $C_1$-$C_3$ haloalkoxy, halogen, cyano or by nitro;

diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$ haloalkyl, $C_1$-$C_3$alkoxy, $C_1$-$C_3$haloalkoxy, halogen, cyano or nitro;

diphenylamino or diphenylamino substituted by $C_1$-$C_3$alkyl, $C_1$-$C_3$ haloalkyl, $C_1$-$C_3$alkoxy, $C_1$-$C_3$haloalkoxy, halogen, cyano or nitro; or $C_3$-$C_7$cycloalkylamino, di$C_3$-$C_7$cycloalkylamino, $C_3$-$C_7$ cycloalkoxy, $C_1$-$C_{10}$alkoxy, $C_1$-$C_{10}$haloalkoxy, $C_1$-$C_5$ alkylamino or $C_2$-$C_8$ dialkylamino;

$R^f$ and $R^g$ are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$ alkylamino$C_1$-$C_5$ alkyl, $C_2$-$C_8$ dialkylamino$C_1$-$C_5$ alkyl, $C_3$-$C_7$ cycloalkyl$C_1$-$C_5$ alkyl, $C_1$-$C_5$ alkoxy$C_1$-$C_5$ alkyl, $C_3$-$C_5$alkenyloxy$C_1$-$C_5$ alkyl, $C_3$-$C_5$ alkynyloxy$C_1$-$C_5$ alkyl, $C_1$-$C_5$ alkylthio$C_1$-$C_5$ alkyl, $C_1$-$C_5$ alkylsulfinyl$C_1$-$C_5$ alkyl, $C_1$-$C_5$ alkylsulfonyl$C_1$-$C_5$ alkyl, $C_2$-$C_8$ alkylideneaminoxy$C_1$-$C_5$ alkyl, $C_1$-$C_5$ alkylcarbonyl$C_1$-$C_5$ alkyl, $C_1$-$C_5$ alkoxycarbonyl$C_1$-$C_5$ alkyl, aminocarbonyl$C_1$-$C_5$ alkyl, $C_1$-$C_5$ alkylaminocarbonyl$C_1$-$C_5$ alkyl, $C_2$-$C_8$ dialkylaminocarbonyl$C_1$-$C_5$ alkyl, $C_1$-$C_5$ alkvicarbonylamino$C_1$-$C_5$ alkyl, N—$C_1$-$C_5$ alkylcarbonyl-N—$C_2$-$C_5$ alkylaminoalkyl, $C_3$-$C_6$trialkylsilyl$C_1$-$C_5$ alkyl, phenyl$C_1$-$C_5$ alkyl (wherein the phenyl is optionally substituted by $C_1$-$C_3$alkyl, $C_1$-$C_3$haloalkyl, $C_1$-$C_3$ alkoxy, $C_1$-$C_3$haloalkoxy, $C_1$-$C_3$ alkylthio, $C_1$-$C_3$alkylsulfinyl, $C_1$-$C_3$ alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$ alkoxy, $C_1$-$C_3$haloalkoxy, $C_1$-$C_3$alkvithio, $C_1$-$C_3$ alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_1$ alkyl, $C_1$-$C_3$haloalkyl, $C_1$-$C_3$alkoxy, $C_1$-$C_3$ haloalkoxy, halogen, cyano or by nitro; heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro; diheteroarylamino or diheteroarylamino substituted by $C_1$-$C_3$ alkyl, $C_1$-$C_3$haloalkyl, $C_1$-$C_3$ alkoxy, $C_1$-$C_3$ haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; diphenylamino or diphenylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; or $C_3$-$C_7$cycloalkylamino, di$C_3$-$C_7$cycloalkylamino, $C_3$-$C_7$cycloalkoxy, $C_1$-$C_{10}$haloalkoxy, $C_1$-$C_5$alkylamino or $C_2$-$C_8$dialkylamino; or benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro; and $R^h$ is $C_1$-$C_{10}$ alkyl, $C_3$-$C_{10}$alkenyl, $C_3$-$C_{10}$ alkynyl, $C_1$-$C_{10}$haloalkyl, $C_1$-$C_{10}$ cyanoalkyl, $C_1$-$C_{10}$nitroalkyl, $C_2$-$C_{10}$aminoalkyl, $C_1$-$C_5$ alkylamino$C_1$-$C_5$alkyl, $C_2$-$C_8$dialkylamino$C_1$-$C_5$alkyl, $C_3$-$C_7$cycloalkyl$C_1$-$C_5$ alkyl, $C_1$-$C_5$alkoxy$C_1$-$C_5$alkyl, $C_3$-$C_5$alkenyloxy$C_1$-$C_5$alkyl, $C_3$-$C_5$ alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$ alkylsulfonyl$C_1$-$C_5$alkyl, $C_2$-$C_g$alkylideneaminoxy$C_1$-$C_5$ alkyl, $C_1$-$C_5$alkyl carbonyl$C_1$-$C_5$ alkyl, $C_1$-$C_5$alkoxycarbonyl$C_1$-$C_5$ alkyl, aminocarbonyl$C_1$-$C_5$ alkyl, $C_1$-$C_5$ alkylaminocarbonyl$C_1$-$C_5$ alkyl, $C_2$-$C_g$dialkylaminocarbonyl$C_1$-$C_5$ alkyl, $C_1$-$C_5$ alkylcarbonylamino$C_1$-$C_5$alkyl, N—$C_1$-$C_5$ alkylcarbonyl-N—$C_1$-$C_5$ alkylamino$C_1$-$C_5$ alkyl, $C_3$-$C_6$trialkylsilyl$C_1$-$C_5$ alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_1$ alkylsulfonyl, halogen, cyano or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$ alkylsulfinyl, $C_1$-$C_3$alkylsulfonyl, halogen, cyano or by nitro), phenoxy$C_1$-$C_5$alkyl (wherein the phenyl is optionally substituted by $C_1$-$C_3$ alkyl, $C_1$-$C_3$haloalkyl, $C_1$-$C_3$alkoxy, $C_1$-$C_3$haloalkoxy, $C_1$-$C_3$alkylthio, $C_1$-$C_3$ alkylsulfinyl, $C_1$-$C_3$alkylsulfonyl, halogen, cyano or by nitro), heteroaryloxy$C_1$-$C_5$ alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_1$ alkylsulfonyl, halogen, cyano or by nitro), $C_3$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro; or heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro;

and wherein "heteroaryl" means a thienyl, furyl, pyrrolyl, oxazolyl, thiazolyl, pyrazolyl, imidazolyl, triazolyl, tetrazolyl, pyridyl, pyrimidinyl, pyrazinyl, or triazinyl group, or a salt thereof.

2. A compound according to claim 1, wherein $R^1$ is methyl, ethyl, methoxy or halogen.

3. A compound according to claim 2, wherein $R^1$ is methyl or ethyl.

4. A compound according to claim 1, wherein $R^2$ is hydrogen, halogen, methyl, ethyl, phenyl or phenyl substituted by $C_1$-$C_3$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl.

5. A compound according to claim 4, wherein $R^2$ is hydrogen or methyl.

6. A compound according to claim 1, wherein $R^3$ is hydrogen, halogen, methyl, ethyl, phenyl or phenyl substituted by $C_1$-$C_3$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl.

7. A compound according to claim 6, wherein $R^3$ is hydrogen or phenyl substituted by halogen.

8. A compound according to claim 1, wherein $R^4$ is hydrogen, methyl or ethyl.

9. A compound according to claim 1, wherein $R^1$, $R^2$ and $R^4$ are independently of each other methyl or ethyl and $R^3$ is hydrogen.

10. A compound according to claim 1, wherein $R^1$ is methyl or ethyl, $R^2$ is hydrogen, $R^3$ is phenyl or phenyl substituted by $C_1$-$C_4$alkyl, $C_1$-$C_3$haloalkyl, $C_1$-$C_3$alkoxy, $C_1$-$C_3$haloalkoxy, cyano, nitro or halogen, or heteroaryl or heteroaryl substituted by $C_1$-$C_4$alkyl, $C_1$-$C_3$haloalkyl, $C_1$-$C_3$alkoxy, $C_1$-$C_3$ haloalkoxy, cyano, nitro or halogen.

11. A compound according to claim 1, wherein $R^1$ is methyl or ethyl, $R^2$ is phenyl or phenyl substituted by $C_1$-$C_4$alkyl, $C_1$-$C_3$haloalkyl, $C_1$-$C_3$alkoxy, $C_1$-$C_3$haloalkoxy, cyano, nitro or halogen, or heteroaryl or heteroaryl substituted by $C_1$-$C_4$alkyl, $C_1$-$C_3$haloalkyl, $C_1$-$C_3$alkoxy, $C_1$-$C_3$haloalkoxy, cyano, nitro or halogen, $R^3$ is hydrogen and $R^4$ is hydrogen, methyl or ethyl.

12. A compound according to claim 1, wherein $R^5$ is hydrogen.

13. A compound according to claim 1, wherein $R^6$ is hydrogen.

14. A compound according to claim 1, wherein $R^7$ and $R^8$ are independently of each other methylene, ethylene, propylene, ethenylene or propenylene.

15. A compound according to claim 14, wherein $R^7$ and $R^8$ are ethylene.

16. A compound according to claim 1, wherein the latentiating group G is $C(X^a)$—$R^a$ or $C(X^b)$—$X^c$—$R^b$.

17. A compound according to claim 1, wherein G is hydrogen, an alkali metal or alkaline earth metal.

18. A compound according to claim 15, wherein G is hydrogen.

19. A compounds according to claim 1, wherein X is O or S.

20. A compounds according to claim 1, wherein X is S(O) or S(O)$_2$.

21. A process for the preparation of a compound of Formula (I) according to claim 1, wherein G is hydrogen, which comprises reacting a compound of the Formula (Z)

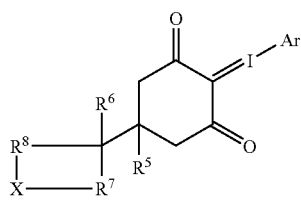

Formula (Z)

wherein $R^6$, $R^7$, $R^8$ and X have the meanings assigned to them in claim 1, and Ar is an optionally substituted phenyl group with an aryl boronic acid of the Formula (AA)

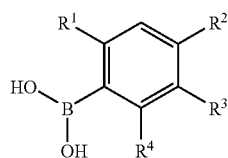

Formula (AA)

wherein $R^1$, $R^2$, $R^3$ and $R^4$ have the meanings assigned to them in claim 1, in the presence of a palladium catalyst and a base.

22. A process for the preparation of a compound of Formula (I) according to claim 1, wherein G is hydrogen, which comprises cyclisation of the compound of the Formula (B)

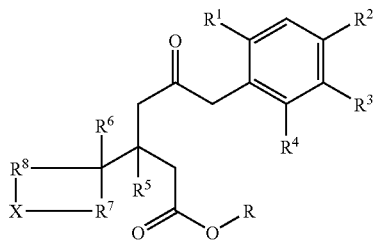

Formula (B)

wherein $R^1$, $R^2$, $R^3$, $R^4$, $R^5$, $R^6$, $R^7$, $R^8$ and X have the meanings assigned to them in claim 1 and R is alkyl, under acidic or basic conditions.

23. A process for the preparation of a compound of Formula (I) according to claim 1, wherein G is an alkyl, acyl, phosphoryl or sulfonyl group, which comprises treating the compound of the formula (A)

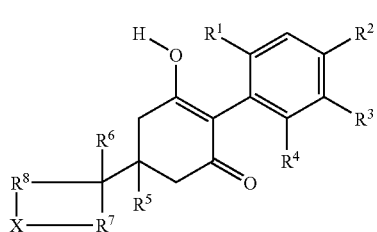

Formula (A)

wherein $R^1$, $R^2$, $R^3$, $R^4$, $R^5$, $R^8$, $R^7$, $R^8$ and X have the meanings assigned to them in claim 1 with a compound of the formula G=Y, wherein G represents the alkyl, acyl, phosphoryl or sulfonyl group to be incorporated and Y is a suitable nucleofuge, in the presence of at least one equivalent of a base.

24. A process for the preparation of a compound of Formula (I) according to claim 1, wherein G is hydrogen, which comprises cyclisation of the compound of the Formula (B)

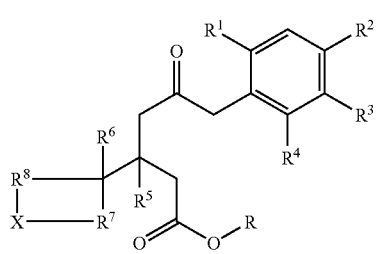

Formula (B)

wherein $R^1$, $R^2$, $R^3$, $R^4$, $R^5$, $R^6$, $R^7$, $R^8$ and X have the meanings assigned to them in claim 1 and R is hydrogen, under acidic conditions.

25. A process for the preparation of a compound of Formula (I) according to claim 1, wherein G is $C_1$-$C_4$ alkyl and $R^5$, $R^6$, $R^7$ and $R^8$ have the meanings assigned to them in claim 1, which comprises treating a compound of Formula (KK)

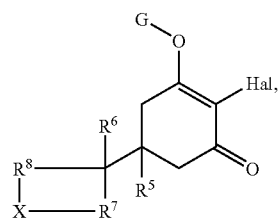

Formula (KK)

wherein G is $C_1$-$C_4$ alkyl, Hal is chlorine, bromine or iodine with an aryl boronic acid of Formula (AA)

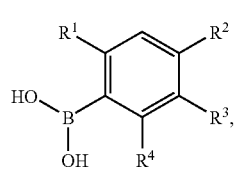

Formula (AA)

wherein $R^1$, $R^2$, $R^3$ and $R^4$ have the meanings assigned to them in claim 1, in the presence of a base, a solvent and a palladium catalyst.

26. A process for the preparation of a compound of Formula (I), wherein G is H, which comprises the hydrolysis of a compound of Formula (I) wherein G is $C_1$-$C_4$ alkyl under acidic conditions.

27. A method of controlling grasses and weeds in crops of useful plants, which comprises applying a herbicidally effective amount of a compound of Formula (I) according to claim 1, or of a composition comprising such a compound, to the plants or to the locus thereof.

28. A herbicidal composition, which, in addition to comprising formulation adjuvants, comprises a herbicidally effective amount of a compound of Formula (I) according to claim 1.

29. A composition according to claim 28, which, in addition to comprising the compound of Formula (I), comprises a further herbicide as mixing partner.

30. A composition according to claim 28, which, in addition to comprising the compound of Formula (I), comprises a safener.

31. A composition according to claim 28, which, in addition to comprising the compound of formula (I), comprises a further herbicide as mixing partner and a safener.

* * * * *